US008530463B2

(12) United States Patent
Cartt et al.

(10) Patent No.: US 8,530,463 B2
(45) **Date of Patent: *Sep. 10, 2013**

(54) MULTIMODAL PARTICULATE FORMULATIONS

(75) Inventors: Steve Cartt, Union City, CA (US); David Medeiros, South San Francisco, CA (US); Edward T. Maggio, San Diego, CA (US)

(73) Assignees: Hale Biopharma Ventures LLC, Encinitas, CA (US); Aegis Therapeutics, LLC, San Diego, CA (US)

(*) Notice: Subject to any disclaimer, the term of this patent is extended or adjusted under 35 U.S.C. 154(b) by 770 days.

This patent is subject to a terminal disclaimer.

(21) Appl. No.: 12/266,529

(22) Filed: Nov. 6, 2008

(65) Prior Publication Data

US 2009/0130216 A1 May 21, 2009

Related U.S. Application Data

(63) Continuation-in-part of application No. 12/116,842, filed on May 7, 2008.

(60) Provisional application No. 60/916,550, filed on May 7, 2007.

(51) Int. Cl.

| | |
|---|---|
| ***A61K 9/14*** | (2006.01) |
| ***A61K 31/00*** | (2006.01) |
| ***A61K 31/55*** | (2006.01) |
| ***A61K 31/551*** | (2006.01) |
| ***A61K 31/5513*** | (2006.01) |
| ***A61K 31/5517*** | (2006.01) |

(52) U.S. Cl.

USPC ... 514/211.08; 424/46; 424/489; 514/211.01; 514/211.1; 514/211.12; 514/211.13; 514/211.14

(58) Field of Classification Search

USPC ................. 424/46, 489; 514/211.01, 211.08, 514/211.1, 211.12, 211.13, 211.14, 218, 514/220

See application file for complete search history.

(56) References Cited

U.S. PATENT DOCUMENTS

| | | | | |
|---|---|---|---|---|
| 3,102,116 | A | 8/1963 | Chase et al. | |
| 3,109,843 | A | 11/1963 | Reeder et al. | |
| 3,136,815 | A | 6/1964 | Reeder et al. | |
| 3,243,427 | A | 3/1966 | Reeder et al. | |
| 3,296,249 | A | 1/1967 | Bell | |
| 3,299,053 | A | 1/1967 | Archer et al. | |
| 3,340,253 | A | 9/1967 | Reeder et al. | |
| 3,371,085 | A | 2/1968 | Reeder et al. | |
| 3,374,225 | A | 3/1968 | Reeder et al. | |
| 3,567,710 | A | 3/1971 | Fryer et al. | |
| 3,609,145 | A | 9/1971 | Moffett | |
| 3,722,371 | A | 3/1973 | Boyle | |
| 3,987,052 | A | 10/1976 | Hester, Jr. | |
| 4,280,957 | A | 7/1981 | Walser et al. | |
| 4,608,278 | A | 8/1986 | Frank et al. | |
| 4,826,689 | A | 5/1989 | Violanto et al. | |
| 4,973,465 | A | 11/1990 | Baurain et al. | |
| 4,997,454 | A | 3/1991 | Violanto et al. | |
| 5,091,188 | A | 2/1992 | Haynes | |
| 5,100,591 | A | 3/1992 | Leclef et al. | |
| 5,118,528 | A | 6/1992 | Fessi et al. | |
| 5,145,684 | A | 9/1992 | Liversidge et al. | |
| 5,188,837 | A | 2/1993 | Domb | |
| 5,457,100 | A | 10/1995 | Daniel | |
| 5,560,932 | A | 10/1996 | Bagchi et al. | |
| 5,661,130 | A | 8/1997 | Meezan et al. | |
| 5,662,883 | A | 9/1997 | Bagchi et al. | |
| 5,665,331 | A | 9/1997 | Bagchi et al. | |
| 5,716,642 | A | 2/1998 | Bagchi et al. | |
| 5,780,062 | A | 7/1998 | Frank et al. | |
| 5,831,089 | A | 11/1998 | Huber | |
| 5,861,510 | A | 1/1999 | Piscopio et al. | |
| 5,863,949 | A | 1/1999 | Robinson et al. | |
| 5,981,719 | A | 11/1999 | Woiszwillo et al. | |
| 6,090,925 | A | 7/2000 | Woiszwillo et al. | |
| 6,143,211 | A | 11/2000 | Mathiowitz et al. | |
| 6,193,985 | B1 | 2/2001 | Sonne | |
| 6,235,224 | B1 | 5/2001 | Mathiowitz et al. | |
| 6,268,053 | B1 | 7/2001 | Woiszwillo et al. | |
| 6,375,986 | B1 | 4/2002 | Ryde et al. | |
| 6,428,814 | B1 | 8/2002 | Bosch et al. | |
| 6,458,387 | B1 | 10/2002 | Scott et al. | |
| 6,607,784 | B2 | 8/2003 | Kipp et al. | |
| 6,610,271 | B2 | 8/2003 | Wermeling | |
| 6,616,914 | B2 * | 9/2003 | Ward et al. | 424/45 |
| 6,627,211 | B1 | 9/2003 | Choi et al. | |

(Continued)

FOREIGN PATENT DOCUMENTS

| | | |
|---|---|---|
| EP | 606046 | 7/1994 |
| EP | 00780386 | 6/1997 |

(Continued)

OTHER PUBLICATIONS

PCT/US09/38696 Search Report dated Sep. 28, 2009.

(Continued)

*Primary Examiner* — James H. Alstrum-Acevedo

(74) *Attorney, Agent, or Firm* — Wilson, Sonsini, Goodrich & Rosati

(57) ABSTRACT

Multimodal particulate formulations of medicaments and methods for their use, e.g. by nasal or pulmonary administration for the treatment of various medical conditions, are provided.

24 Claims, No Drawings

(56) References Cited

U.S. PATENT DOCUMENTS

| | | | |
|---|---|---|---|
| 6,869,617 | B2 | 3/2005 | Kipp |
| 6,884,436 | B2 | 4/2005 | Kipp |
| 6,908,626 | B2 | 6/2005 | Cooper et al. |
| 7,037,528 | B2 | 5/2006 | Kipp |
| 7,132,112 | B2 | 11/2006 | Choi et al. |
| 7,434,579 | B2 | 10/2008 | Young et al. |
| 2001/0042932 | A1 | 11/2001 | Mathiowitz et al. |
| 2002/0127278 | A1 | 9/2002 | Kipp |
| 2002/0168402 | A1 | 11/2002 | Kipp |
| 2003/0031719 | A1 | 2/2003 | Kipp |
| 2003/0181411 | A1 | 9/2003 | Bosch et al. |
| 2006/0046962 | A1 | 3/2006 | Meezan et al. |
| 2006/0198896 | A1 | 9/2006 | Liversidge et al. |
| 2008/0248123 | A1 | 1/2008 | Swanson et al. |
| 2008/0200418 | A1 | 8/2008 | Maggio |
| 2008/0279784 | A1 | 11/2008 | Cartt |
| 2008/0299079 | A1 | 12/2008 | Meezan et al. |
| 2009/0047347 | A1 | 2/2009 | Maggio |
| 2009/0163447 | A1 | 6/2009 | Maggio |
| 2009/0258865 | A1 | 10/2009 | Cartt |
| 2009/0297619 | A1 | 12/2009 | Swanson et al. |
| 2009/0304801 | A1 | 12/2009 | Liversidge et al. |
| 2010/0068209 | A1 | 3/2010 | Maggio |
| 2011/0172211 | A1 | 7/2011 | Back et al. |
| 2011/0257096 | A1 | 10/2011 | Maggio |
| 2012/0196941 | A1 | 8/2012 | Maggio |
| 2013/0065886 | A1 | 3/2013 | Cartt |

FOREIGN PATENT DOCUMENTS

| | | | |
|---|---|---|---|
| EP | 0818442 | | 1/1998 |
| EP | 931788 | | 7/1999 |
| EP | 0945485 | | 9/1999 |
| EP | 1004578 | | 5/2000 |
| JP | 2003-505403 | | 2/2003 |
| JP | 2005-508939 | | 4/2005 |
| JP | 2007-510722 | | 4/2007 |
| WO | WO-90-05719 | | 5/1990 |
| WO | WO-96-27583 | | 9/1996 |
| WO | WO-96-33172 | | 10/1996 |
| WO | WO-97-14407 | A1 | 4/1997 |
| WO | WO-98-03516 | | 1/1998 |
| WO | WO-98-07697 | | 2/1998 |
| WO | WO-98-30566 | | 7/1998 |
| WO | WO-98-33768 | | 8/1998 |
| WO | WO-98-34915 | | 8/1998 |
| WO | WO-98-34918 | | 8/1998 |
| WO | WO-99-07675 | | 2/1999 |
| WO | WO-99-29667 | | 6/1999 |
| WO | WO-99-52889 | | 10/1999 |
| WO | WO-99-52910 | | 10/1999 |
| WO | WO-00-74681 | | 12/2000 |
| WO | WO-2005-044234 | A2 | 5/2005 |
| WO | WO-2005-089768 | | 9/2005 |
| WO | WO-2005-117830 | A1 | 12/2005 |
| WO | WO-2006-055603 | | 5/2006 |
| WO | WO-2006-075123 | A1 | 7/2006 |
| WO | WO-2006-088894 | | 8/2006 |
| WO | WO-2007-043057 | A2 | 4/2007 |
| WO | WO-2007-144081 | A1 | 12/2007 |

OTHER PUBLICATIONS

US 5,849,884, Dec. 1998, Woiszwillo et al. (withdrawn).

PCT/US08/62961 Search Report dated Jul. 25, 2008.

Wermeling et al., "Pharmacokinetics and pharmacodynamics of a new intranasal midazolam formulation in healthy volunteers," Anesthesia & Analgesia 103(2):344-349 (2006).

EP08747813 Supplementary Search Report dated Jun. 2, 2010.

U.S. Appl. No. 60/148,464, filed Aug. 12, 1999, Noe.

PCT/US2012/042311 Search Report dated Aug. 31, 2012.

* cited by examiner

MULTIMODAL PARTICULATE FORMULATIONS

This application is a continuation-in-part of U.S. patent application Ser. No. 12/116,842, filed May 7, 2008, which claims benefit of priority of provisional application U.S. Ser. No. 60/916,550, filed on May 7, 2007; the entire contents of each of these applications are incorporated herein by reference.

FIELD OF THE INVENTION

This application relates to nanoparticulate drug compositions and to aerosol administration of nanoparticulate drugs.

BACKGROUND OF THE INVENTION

Various drugs have been administered orally or parenterally, e.g. by intravenous (IV), intramuscular (IM) or subcutaneous (subcu) injection. Injection of a drug can be effective, but is often characterized by patient discomfort and inconvenience, and thus poor patient compliance. As a result, it is often considered desirable to provide a medicament in an oral formulation, as an alternative to, or substitute for, injection. However, oral formulations are often characterized by poor absorption, rapid first-pass metabolism in the liver, slow attainment of effective blood plasma levels and other problems.

Intranasal formulations have been used for delivery of some medicaments. Nasal preparations are generally administered in metered sprays having volumes of less than 25 μl, preferably less than 150 μl, and ideally from 25 to 100 μl, since administration of larger volumes usually exceeds the capacity of the nasal sinuses and results in volumes in excess of about 250 μl bypassing the sinuses and flowing down the back of the throat where it is swallowed. As smaller dose volumes are preferred for nasal administration, poor water solubility of many compounds limits the dose that may be administered to a patient at any given time. This in turn limits the clinical effectiveness of nasally-administered medicaments.

There is a need for formulations that are capable of providing to the nasal mucosa sufficient quantity of active pharmaceutical agents in a small enough volume to provide therapeutically effective blood plasma concentration of active pharmaceutical agent within a short period after administration of the formulation to the nasal mucosa. These and other objects and advantages are provided by the invention described herein.

SUMMARY OF THE INVENTION

The foregoing and further needs are met by embodiments of the present invention, which provide a composition for aerosol administration of a medicament, comprising a first population of particles having a first effective mean particle diameter and a second population of particles having a second effective mean particle diameter, wherein the first effective mean particle diameter is at least 1.5 times, at least 1.6 times, at least 1.7 times, at least 1.8 times, at least 1.9 times, at least 2 times, at least 2.5 times or at least 3 times that of the second effective mean particle diameter. In some embodiments, the aerosol is adapted for nasal administration. In some embodiments, the aerosol is adapted for pulmonary administration. In some embodiments, the aerosol is a dry powder. In some embodiments, the aerosol is a particle suspension in a liquid suitable for administration with a metered dose inhaler. In some embodiments, the aerosol is an aqueous suspension suitable for administration with a nebulizer.

The foregoing and further needs are met by embodiments of the present invention, which provide a composition for aerosol administration of a medicament, comprising a first population of particles having a first effective mean particle diameter and a second population of particles having a second effective mean particle diameter, wherein the first effective mean particle diameter is at least twice that of the second effective mean particle diameter. In some embodiments, the aerosol is administered to the nasal mucosa. In some embodiments, the aerosol is administered by pulmonary inhalation. In some embodiments, the aerosol is a dry powder and is administered with a dry powder inhaler. In some embodiments, the aerosol is a particle suspension in a liquid and is administered with a metered dose inhaler. In some embodiments, the aerosol is an aqueous suspension administered with a nebulizer.

The foregoing and further needs are met by embodiments of the present invention, which provide a method of using a composition for aerosol administration of a medicament, comprising a first population of particles having a first effective mean particle diameter and a second population of particles having a second effective mean particle diameter, wherein the first effective mean particle diameter is at least 1.5 times, at least 1.6 times, at least 1.7 times, at least 1.8 times, at least 1.9 times, at least 2 times, at least 2.5 times or at least 3 times that of the second effective mean particle diameter. In some embodiments, the aerosol is administered to the nasal mucosa. In some embodiments, the method comprises administering an effective amount of the composition to the nose by administering a therapeutically effective amount of the composition to at least one nostril. In some embodiments, the aerosol is administered by pulmonary inhalation. In some embodiments, the aerosol is a dry powder and is administered with a dry powder inhaler. In some embodiments, the aerosol is a particle suspension in a liquid and is administered with a metered dose inhaler. In some embodiments, the aerosol is an aqueous suspension administered with a nebulizer.

The foregoing and further needs are met by embodiments of the present invention, which provide a method of using a composition for aerosol administration of a medicament, comprising a first population of particles having a first effective mean particle diameter and a second population of particles having a second effective mean particle diameter, wherein the first effective mean particle diameter is at least twice that of the second effective mean particle diameter. In some embodiments, the aerosol is administered to the nasal mucosa. In some embodiments, the method comprises administering an effective amount of the composition to the nose by administering a therapeutically effective amount of the composition to at least one nostril. In some embodiments, the aerosol is administered by pulmonary inhalation. In some embodiments, the aerosol is a dry powder and is administered with a dry powder inhaler. In some embodiments, the aerosol is a particle suspension in a liquid and is administered with a metered dose inhaler. In some embodiments, the aerosol is an aqueous suspension administered with a nebulizer.

The foregoing and further needs are met by embodiments of the present invention, which provide a pharmaceutical particulate composition for aerosol delivery of a medicament comprising particulates having a multimodal particle size distribution. In some embodiments, the aerosol is adapted for nasal administration. In some embodiments, the aerosol is adapted for pulmonary administration. In some embodiments, the aerosol is a dry powder. In some embodiments, the aerosol is a particle suspension in a liquid suitable for administration with a metered dose inhaler. In some embodiments, the aerosol is an aqueous suspension suitable for administration with a nebulizer.

The foregoing and further needs are met by embodiments of the present invention, which provide a method of using a pharmaceutical particulate composition for nasal delivery of a medicament comprising particulates having a multimodal particle size distribution, comprising administering an effective amount of the composition to the nose by administering a therapeutically effective amount of the composition to at least one nostril.

The foregoing and further needs are met by embodiments of the invention, which provide a method of using a pharmaceutical particulate composition for pulmonary delivery of a medicament comprising particulates having a multimodal particle size distribution, comprising administering an effective amount of the composition from a suitable pulmonary delivery device. In some embodiments, the suitable delivery device is a dry powder inhalation device. In some embodiments, the suitable delivery device is a metered dose inhaler. In some embodiments, the suitable delivery device is a nebulizer.

The foregoing and further needs are further met by embodiments of the present invention, which provide an aerosol composition of an aqueous suspension or dispersion of nanoparticulate medicament particles having a multimodal particle size distribution, wherein: the droplets of the aerosol have a mass median aerodynamic diameter (MMAD) less than or equal to about 1000 μm and the nanoparticulate medicament particles have an effective average particle size of less than about 5000 nm. In some embodiments, the aerosol composition is adapted for nasal administration. In some embodiments, the aerosol composition is adapted for pulmonary administration. In some embodiments, the droplets have an MMAD of less than or equal to about 5 μm. In some embodiments, at least one population of particles comprises medicament particles having an effective average particle size of less than about 5 μm. In some embodiments, at least one population of particles comprises medicament particles having an effective average particle size of about 0.5 μm to about 5.0 μm. In some embodiments, at least one population of particles has an effective average particle size of about 0.5 μm to about 2.0 μm or about 2.0 μm to about 5.0 μm. In some embodiments, at least one population of particles has an effective average particle size of greater than about 5.0 μm. In some embodiments, at least one population of particles has an effective average particle size of less than about 5.0 μm and at least one population of particles has an effective average particle size of greater than about 5.0 μm. In some embodiments, at least one population of particles is adapted for administration to the pulmonary mucosa. In some embodiments, at least one population of particles is adapted for administration to the nasal, oropharyngeal and/or gastrointestinal mucosa. In some embodiments, one population of particles is adapted for penetration into the deep lung and another population of particles is adapted for penetration into the upper lung.

The foregoing and further needs are further met by embodiments of the present invention, which provide a method of using an aerosol composition of an aqueous suspension or dispersion of nanoparticulate medicament particles, wherein: the droplets of the aerosol have a mass median aerodynamic diameter (MMAD) less than or equal to about 1000 μm and the nanoparticulate medicament particles have an effective average particle size of less than about 5000 nm, the method comprising administering an effective amount of the composition to a patient by nasal or pulmonary administration. In some embodiments, the aerosol composition is adapted for nasal administration. In some embodiments, the aerosol composition is administered to the nose by spraying a therapeutically effective amount of the composition into at least one nostril. In some embodiments, the aerosol composition is adapted for pulmonary administration.

The foregoing and further needs are met by embodiments of the present invention, which provide a method of administering a medicament drug to a patient, comprising administering to the nose, nasal cavity or lungs of a patient an effective amount of an aerosol composition of an aqueous suspension or dispersion of nanoparticulate medicament particles, wherein: the droplets of the aerosol have a mass median aerodynamic diameter (MMAD) less than or equal to about 1000 μm and the nanoparticulate medicament particles have an effective average particle size of less than about 5000 nm, the method comprising administering an effective amount of the composition to a patient by nasal or pulmonary administration. In some embodiments, the droplets have an MMAD of less than or equal to about 5 μm. In some embodiments, at least one population of particles comprises medicament particles having an effective average particle size of less than about 5 μm. In some embodiments, at least one population of particles comprises medicament particles having an effective average particle size of about 0.5 μm to about 5.0 μm. In some embodiments, at least one population of particles has an effective average particle size of about 0.5 μm to about 2.0 μm or about 2.0 μm to about 5.0 μm. In some embodiments, at least one population of particles has an effective average particle size of greater than about 5.0 μm. In some embodiments, at least one population of particles has an effective average particle size of less than about 5.0 μm and at least one population of particles has an effective average particle size of greater than about 5.0 μm. In some embodiments, at least one population of particles is adapted for administration to the pulmonary mucosa. In some embodiments, at least one population of particles is adapted for administration to the nasal, oropharyngeal and/or gastrointestinal mucosa. In some embodiments, one population of particles is adapted for penetration into the deep lung and another population of particles is adapted for penetration into the upper lung.

The foregoing and further needs are met by embodiments of the present invention, which provide a method of administering a medicament drug to a patient, comprising administering to the lungs and/or oropharyngeal mucosa an effective amount of an aerosol composition of an aqueous suspension or dispersion of nanoparticulate medicament particles, wherein: the droplets of the aerosol have a mass median aerodynamic diameter (MMAD) less than or equal to about 1000 μm and the nanoparticulate medicament particles have an effective average particle size of less than about 5000 nm. In some embodiments, the droplets have an MMAD of less than or equal to about 5 μm. In some embodiments, at least one population of particles comprises medicament particles having an effective average particle size of less than about 5 μm. In some embodiments, at least one population of particles comprises medicament particles having an effective average particle size of about 0.5 μm to about 5.0 μm. In some embodiments, at least one population of particles has an effective average particle size of about 0.5 μm to about 2.0 μm or about 2.0 μm to about 5.0 μm. In some embodiments, at least one population of particles has an effective average particle size of greater than about 5.0 μm. In some embodiments, at least one population of particles has an effective average particle size of less than about 5.0 μm and at least one population of particles has an effective average particle size of greater than about 5.0 μm. In some embodiments, at least one population of particles is adapted for administration to the pulmonary mucosa. In some embodiments, at least one population of particles is adapted for administration to the nasal, oropharyngeal and/or gastrointestinal mucosa. In some embodiments, one population of particles is adapted for penetration into the deep lung and another population of particles is adapted for penetration into the upper lung.

The foregoing and further needs are additionally met by embodiments of the present invention, which provide a pharmaceutical composition for nasal administration of medicament comprising medicament particles and one or more non-cationic surface active agents adsorbed to a surface thereof.

The foregoing and further needs are additionally met by embodiments of the present invention, which provide a pharmaceutical composition for pulmonary administration of medicament comprising medicament particles and one or more non-cationic surface active agents adsorbed to a surface thereof.

The foregoing and further needs are further met by embodiments of the invention, which provides a method of administering a pharmaceutical composition for nasal administration of medicament comprising medicament particles and one or more non-cationic surface active agents adsorbed to a surface thereof, the method comprising administering an effective amount of the composition to the nose by administering a therapeutically effective amount of the composition to at least one nostril.

The foregoing and further needs are further met by embodiments of the invention, which provides a method of administering a pharmaceutical composition for pulmonary administration of medicament comprising medicament particles and one or more non-cationic surface active agents adsorbed to a surface thereof, the method comprising administering an effective amount of the composition to the lungs a therapeutically effective amount of the composition.

The foregoing and further needs are met by embodiments of the present invention, which provide a method of administering a medicament drug to a patient, comprising administering to the patient's nose or nasal cavity a pharmaceutical composition comprising particles of a medicament drug having a surface active agent adsorbed to a surface thereof.

The foregoing and further needs are met by embodiments of the present invention, which provide a method of administering a medicament drug to a patient, comprising administering to the patient's lungs and/or oropharyngeal mucosa a pharmaceutical composition comprising particles of a medicament drug having a surface active agent adsorbed to a surface thereof.

The foregoing and further needs are met by embodiments of the present invention, which provide a non-aqueous dispersion or suspension of nanoparticulate medicament particles. In some embodiments, the nanoparticulate medicament has a multimodal particle size distribution. In some embodiments, the nanoparticulate medicament has a bimodal particle size distribution. In some embodiments, the nanoparticulate medicament has a trimodal particle size distribution. In some embodiments, the nanoparticulate medicament is adapted for nasal administration, e.g. with a metered dose nasal insufflator. In some embodiments, the nanoparticulate medicament is adapted for pulmonary administration, e.g. with a metered dose inhaler. In some embodiments, at least one population of particles has a mean particle size of less than about 5 μm. In some embodiments, at least one population of particles has a mean particle size of about 0.5 μm to about 5 μm. In some embodiments, at least one population of particles has a mean particle size of about 0.5 μm to about 2.0 μm. In some embodiments, at least one population of particles has a mean particle size of about 2.0 μm to about 5.0 μm. In some embodiments, at least one population of particles has a mean particle size of about 0.5 μm to about 5 μm and at least one population of particles has a mean particle size of greater than about 5 μm.

The foregoing and additional needs are further met by embodiments of the present invention, which provide a method of administering a non-aqueous dispersion or suspension of nanoparticulate medicament particles, the method comprising administering an effective amount of the dispersion or suspension to the nose by administering a therapeutically effective amount of the composition to at least one nostril.

The foregoing and further needs are additionally met by embodiments of the present invention, which provide, a method of administering a medicament drug to a patient, comprising administering to the patient's nose or nasal cavity a pharmaceutical composition comprising a non-aqueous dispersion or suspension of nanoparticulate medicament particles.

The foregoing and additional needs are further met by embodiments of the invention, which provide a nanoparticulate composition comprising: (a) a benzodiazepine having an effective average particle size of less than about 2000 nm, wherein the benzodiazepine is selected from the group consisting of alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, midazepam, lorazepam, prazepam, quazepam, triazolam, temazepam, loprazolam, pharmaceutically acceptable salts and esters thereof, and mixtures thereof, and (b) at least one surface stabilizer. In some embodiments, the surface stabilizer is selected from the group consisting of a nonionic surfactant, an ionic surfactant, a cationic surfactant, an anionic surfactant, and a zwitterionic surfactant. In some embodiments, the nanoparticulate benzodiazepine has a multimodal particle size distribution. In some embodiments, the nanoparticulate benzodiazepine has a bimodal particle size distribution. In some embodiments, the nanoparticulate benzodiazepine has a trimodal particle size distribution. In some embodiments, the nanoparticulate benzodiazepine is adapted for nasal administration, e.g. with a metered dose nasal insufflator. In some embodiments, the nanoparticulate benzodiazepine is adapted for pulmonary administration, e.g. with a metered dose inhaler. In some embodiments, at least one population of particles has a mean particle size of less than about 5 μm. In some embodiments, at least one population of particles has a mean particle size of about 0.5 μm to about 5 μm. In some embodiments, at least one population of particles has a mean particle size of about 0.5 μm to about 2.0 μm. In some embodiments, at least one population of particles has a mean particle size of about 2.0 μm to about 5.0 μm. In some embodiments, at least one population of particles has a mean particle size of about 0.5 μm to about 5 μm and at least one population of particles has a mean particle size of greater than about 5 μm.

The foregoing and additional needs are further met by a method of treating a subject in need comprising administering to the subject a nanoparticulate benzodiazepine composition comprising: (a) a benzodiazepine having an effective average particle size of less than about 2000 nm, wherein the benzodiazepine is selected from the group consisting of alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, midazepam, lorazepam, prazepam, quazepam, triazolam, temazepam, loprazolam, pharmaceutically acceptable salts and esters thereof, and mixtures thereof, and (b) at least one surface stabilizer. In some embodiments, the surface stabilizer is selected from the group consisting of a nonionic surfactant, an ionic surfactant, a cationic surfactant, an anionic surfactant, and a zwitterionic surfactant. In some embodiments, the nanoparticulate benzodiazepine has a multimodal particle size distribution. In some embodiments, the nanoparticulate benzodiazepine has a bimodal particle size distribution. In some embodiments, the nanoparticulate benzodiazepine has a trimodal particle size distribution. In some embodiments, the nanoparticulate benzodiazepine is adapted for nasal administration, e.g. with a metered dose nasal insufflator. In some embodiments, the nanoparticulate benzodiazepine is adapted for pulmonary administration, e.g. with a metered dose inhaler. In some embodiments, at least one population of particles has a mean particle size of less than about 5 μm. In some embodiments, at least one population of particles has a mean particle size of about 0.5 μm to about 5 μm. In some embodiments, at least one population of particles has a mean particle size of about 0.5 μm to about 2.0 μm. In some embodiments, at least one population of particles has a mean particle size of about 2.0 μm to about 5.0 μm. In some embodiments, at least one population of particles has a mean particle size of about 0.5 μm to about 5 μm and at least one population of particles has a mean particle size of greater than about 5 μm.

These and further advantages and characteristics of the present invention will become apparent to the person skilled in the art upon consideration of the description and claims.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

The present invention provides aerosol (e.g. nasal and pulmonary) formulations for administering various drugs. In some embodiments, there are provided compositions comprising nanoparticulates characterized by multimodal (e.g. bimodal or trimodal) particle size distribution. In particular embodiments, the compositions are characterized by containing two or more populations of nanoparticles, each having a particle size distribution possessing a distinct node. The aerosol compositions can be used to deliver e.g. benzodiazepine drugs, other anticonvulsants (such as aromatic allylic alcohols, barbiturates, bromides, carbamates, carboxamides, fatty acids, topiramate, Gaba analogs, hydantoins, oxazolidinediones, propionates, pyrimidinediones, pyrrolidines, succinimides, sulfonamides, triazines, ureas, valproylamides, etc.), insulin, calcitonins, enkephalins, LHRH and analogs, GHRH (growth hormone releasing hormone), nifedipin, THF (thymic humoral factor), CGRP (calcitonin gene related peptide), atrial natriuretic peptide, antibiotics, metoclopramide, ergotamine, Pizotizin, nasal vaccines (particularly HIV vaccines, measles, rhinovirus Type 13 and respiratory syncitial virus), pentamidine, CCK (Cholecystikinine), DDVAP, Interferons, growth hormone, secretin, bradykinin antagonists, GRF (Growth releasing factor), THF, TRH (Thyrotropin releasing hormone), ACTH analogues, IGF (Insulin like growth factors), CGRP (Calcitorin gene related peptide), Atrial Natriuretic peptide, Vasopressin and analogs (DDAVP, Lypressin), Metoclopramide, Migraine treatment (e.g. Dihydroergotamine, Ergometrine, Ergotamine, Pizotizin), Nasal Vaccines (Particularly AIDS vaccines), FACTOR VIII, Colony Stimulating factors, G-CSF (granulocyte-colony stimulating factor), EPO (Erythropoitin) PTH (Parathyroid hormone), antibiotics and antimicrobial agents (such as tetracyline hydrochloride, leucomycin, penicillin, penicillin derivatives, erythromycin, gentamicin, sulphathiazole and nitro furazone), local anaesthetics, vasoconstrictors, tetrahydrozoline hydrochloride, naphazoline nitrate, oxymetazoline hydrochloride and tramazoline hydrochloride, cardiotonics, vasodilators, antiseptics, enzymes, vitamin D, active vitamin D, vitamin C, sex hormones, hypotensives, sedatives, antitumor agents, steroidal anti-inflammatory agents, non-steroidal anti-inflammatory agents, enzymatic anti-inflammatory agents, anti-allergic agents, antitussive-expectorant agents, antasthmatic agents, or pharmaceutically acceptable salts or combinations thereof.

As used herein, the terms “average” and “mean” are synonymous, unless otherwise stated. As used herein, the terms “particle size” and “particle diameter” are synonymous, unless otherwise stated. As used herein, the pharase “effective mean particle diameter” is intended to by synonymous with “effective average particle size” as used in United States pre-grant publication number US 2006/0198896, which is incorporated herein by reference in its entirety. Effective mean particle diameter (effective average particle size) may be measured by an art-recognized method, such as by light-scattering methods, microscopy, or other appropriate methods. Redispersibility can be tested e.g. as set forth in the examples of U.S. Pat. No. 6,375,986, which is incorporated herein by reference.

As used herein, “pulmonary” refers to the lungs and “pulmonary delivery” refers to delivery of a composition, e.g. a medicament comprising a benzodiazepine drug, to the lungs. The person of skill in the art will recognize that not all of a dose of medicament for administration to the lungs will actually be deposited in the lungs. Different modes of administration to the lungs are characterized by different degrees of tendency to deposit the medicament in the lungs. The portion of drug that is not deposited in the lungs is generally divided between that which is exhaled, that which is deposited in the oropharyngeal cavity and that which escapes inhalation altogether, e.g. through leakage around a nebulization mask, etc. The portion of the drug that is deposited in the oropharyngeal cavity may be absorbed directly through the oropharyngeal mucosa and/or may be swallowed and, if stable in the gastrointestinal tract, absorbed through the gastrointestinal mucoa. The person of skill in the art will recognize that, no mode of pulmonary delivery is 100% efficient in delivering drug to the lungs, and that though some (potentially large) fraction of the drug is deposited in some other organ or tissue than the lung, delivery of a medicament to the lungs, e.g. using a nebulizer, a dry powder inhaler or a metered dose inhaler, is “pulmonary delivery” for purposes of the invention described in various embodiments herein.

In some embodiments, the invention provides for administration aerosol (e.g. nasal and pulmonary) formulations for administering one or more benzodiazepine drugs, such as diazepam, lorazepam or midazolam, to a patient in need of therapeutic treatment with a benzodiazepine drug. In some embodiments, the invention further provides methods of administering a benzodiazepine to a patient, comprising nasally administering an effective amount of the benzodiazepine to the patient, wherein the effective amount of the composition is effective to treat seizure, protect against seizure, reduce or ameliorate the intensity of seizure, reduce or ameliorate the frequency of seizure, and/or prevent occurrence or re-occurrence of seizure. In some embodiments, the invention further provides methods of administering a benzodiazepine to a patient, comprising nasally administering an effective amount of the benzodiazepine to the patient, wherein the effective amount of the composition is effective to provide a therapeutic effect selected from an anxiolytic effect, an anticonvulsant effect, a sedative effect, a skeletal muscle relaxant effect, an amnesic effect or combinations thereof.

In some embodiments, the invention provides a composition for aerosol (e.g. nasal or pulmonary) administration of a medicament comprising a first population of particles having a first effective mean particle diameter and a second population of particles having a second effective mean particle diameter, wherein the first effective mean particle diameter is at least 1.5 times, at least 1.6 times, at least 1.7 times, at least 1.8 times, at least 1.9 times, at least 2 times, at least 2.5 times or at least 3 times that of the second effective mean particle diameter. In some embodiments, the invention provides a composition for aerosol (e.g. nasal or pulmonary) administration of a medicament comprising a first population of particles having a first effective mean particle diameter and a second population of particles having a second effective mean particle diameter, wherein the first effective mean particle diameter is at least twice that of the second effective mean particle diameter. In some embodiments, the first population of particles comprises a first active ingredient. In some embodiments, the first population of particles and the second population of particles both comprise the first active ingredient. In some embodiments, the second population of particles comprises a second active ingredient. In some embodiments, the first population of particles, the second population of particles or both the first and second populations of particles comprise a first active ingredient and a second active ingredient. In some embodiments, the medicament comprises a benzodiazepine. In some embodiments, the medicament comprises other anticonvulsants (such as aromatic allylic alcohols, barbiturates, bromides, carbamates, carboxamides, fatty acids, topiramate, Gaba analogs, hydantoins, oxazolidinediones, propionates, pyrimidinediones, pyrrolidines, succinimides, sulfonamides, triazines, ureas, valproylamides, etc.), insulin, calcitonins, enkephalins, LHRH and analogs, GHRH (growth hormone releasing hormone), nifedipin, THF (thymic humoral factor), CGRP (calcitonin gene related peptide), atrial natriuretic peptide, antibiotics, metoclopramide, ergotamine, Pizotizin, nasal vaccines (particularly HIV vaccines, measles, rhinovirus Type 13 and respiratory syncitial virus), pentamidine, CCK (Cholecystikinine), DDVAP, Interferons, growth hormone, secretin, bradykinin antagonists, GRF (Growth releasing factor), THF, TRH (Thyrotropin releasing hormone), ACTH analogues, IGF (Insulin like growth factors), CGRP (Calcitorin gene related peptide), Atrial Natriuretic peptide, Vasopressin and analogs (DDAVP, Lypressin), Metoclopramide, Migraine treatment (e.g. Dihydroergotamine, Ergometrine, Ergotamine, Pizotizin), Nasal Vaccines (Particularly AIDS vaccines), FACTOR VIII, Colony Stimulating factors, G-CSF (granulocyte-colony stimulating factor), EPO (Erythropoitin) PTH (Parathyroid hormone), antibiotics and antimicrobial agents (such as tetracyline hydrochloride, leucomycin, penicillin, penicillin derivatives, erythromycin, gentamicin, sulphathiazole and nitrofurazone), local anaesthetics, vasoconstrictors, tetrahydrozoline hydrochloride, naphazoline nitrate, oxymetazoline hydrochloride and tramazoline hydrochloride, cardiotonics, vasodilators, antiseptics, enzymes, vitamin D, active vitamin D, vitamin C, sex hormones, hypotensives, sedatives, antitumor agents, steroidal anti-inflammatory agents, non-steroidal anti-inflammatory agents, enzymatic anti-inflammatory agents, anti-allergic agents, antitussive-expectorant agents, antasthmatic agents, or pharmaceutically acceptable salts or combinations thereof. In some embodiments, the medicament comprises a benzodiazepine selected from the group consisting of: alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, medazepam, lorazepam, prazepam, quazepam, triazolam, temazepam, loprazolam, and pharmaceutically acceptable salts and combinations thereof. In some embodiments, the benzodiazepine comprises at least one member of the group consisting of alprazolam, diazepam, flurazepam, lorazepam, medazepam, mexazolam, midazolam, temazepam and pharmaceutically acceptable salts and combinations thereof. In some embodiments, the benzodiazepine comprises one or more members of the group consisting of: diazepam, lorazepam, midazolam and pharmaceutically acceptable salts thereof. In some embodiments, the particles in the medicament have a mean diameter of greater than about 500 nm, greater than about 1000 nm, greater than about 2000 nm, greater than about 4000 nm or greater than about 5000 nm. In some embodiments, the second population of particles or both are coated with at least one surface acting agent. In some embodiments, at least one surface acting agent is a cationic surfactant, a non-ionic surfactant, an anionic surfactant, a surface active biological modifier or a zwitterionic surfactant. In some embodiments, at least one surface acting agent is a cationic surfactant selected from the group consisting of natural phospholipids, synthetic phospholipids, quaternary ammonium compounds, benzalkonium chloride, cetyltrimethylammonium bromide, chitosans, lauryldimethylbenzylammonium chloride, acyl camitine hydrochlorides, dimethyldioctadecylammomium bromide (DDAB), dioleyoltrimethylammonium propane (DOTAP), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, and long-chain alkyl amines such as, for example, n-octylamine and oleylamine. In some embodiments, at least one surface acting agent is an anionic surface active agent selected from the group consisting of natural anionic phospholipids, synthetic anionic phospholipids and anionic polymers. In some embodiments, the natural anionic phospholipids, synthetic anionic phospholipids and anionic polymers are selected from the group consisting of polyacrylic acid, carrageenan k type II, carbopol 980, carbopol 974 P, carbopol 971 P, polycarbophil, sodium carboxymethylcellulose, sodium hyaluronate or combinations thereof. In some embodiments, at least one surface acting agent is selected from the group consisting of thiolated polymers. In some embodiments, the thiolated polymer is selected from the group consisting of cysteine conjugates of polyacrylic acid, polycarbophil (thiomer polycarbophil-cysteine), thiolated sodium carboxymethylcellulose, chitosan modified with 2-iminothiolate (e.g. chitosan-4-thiobutylamidine conjugates, chitosan-thioglycolic acid conjugates, chitosan-cysteine conjugates). In some embodiments, at least one surface acting agent is selected from the group consisting of polymeric mucilaginous polysaccharides. In some embodiments, the polymeric mucilaginous polysaccharide is from the aloe vera plant. In some embodiments, at least one surface acting agent is methylcellulose, ethylcellulose, hydroxypropylmethylcellulose (HPMC) or a mixture of two or more thereof. In some embodiments, the composition comprises a third population of benzodiazepine particles having a third mean particle size distribution different from the first and second populations of particles. In some embodiments, the composition further comprises one or more additional ingredient selected from active pharmaceutical ingredients and enhancers. In some embodiments, the first population of particles has a mean diameter in the range of about 25 to about 4000 nm and the second population of particles has a mean diameter in the range of about 500 to about 10,000 nm. In some embodiments, the first population of particles has a mean diameter in the range of about 50 to about 2000 nm and the second population of particles has a mean diameter in the range of about 1000 nm to about 10,000 nm. In some embodiments, the first population of particles has a mean diameter in the range of about 50 to about 1000 nm and the second population of particles has a mean diameter in the range of about 1000 nm to about 10,000 nm. In some embodiments, the mean particle diameter of the first population of particles is smaller than the mean particle diameter of the second population of particles. In some embodiments, the first population of particles has a mean diameter in the range of about 50 to about 500 nm and the second population of particles has a mean diameter in the range of about 2000 to about 10,000 nm. In some embodiments, the difference between the mean particle size of the first and second populations is greater than about 100 nm, greater than about 200 nm, greater than about 500 nm, greater than about 1000 nm, greater than about 2000 nm, greater than about 3000 nm, greater than about 4000 nm, greater than about 5000 nm, greater than about 6000 nm, greater than about 7000 nm, greater than about 8000 nm, greater than about 9000 nm or greater than about 10,000 nm. In some embodiments, the difference between the mean particle size of the first and second particle populations is greater than about 10%, greater than about 20% or greater than about 30% of the mean particle diameter of the second population of particles. In some embodiments, the benzodiazepine particles do not contain solvent residues resulting from solvent extraction or solvent precipitation.

In some embodiments, the invention provides a method of using a composition for aerosol (e.g. nasal or pulmonary) administration of a medicament, the composition comprising a first population of particles having a first effective mean particle diameter and a second population of particles having a second effective mean particle diameter. In some embodiments, the first effective mean particle diameter is at least 1.5 times, at least 1.6 times, at least 1.7 times, at least 1.8 times, at least 1.9 times, at least 2 times, at least 2.5 times or at least 3 times that of the second effective mean particle diameter, comprising administering an effective amount of the composition to the nose by administering a therapeutically effective amount of the composition to at least one nostril. In some embodiments, the first effective mean particle diameter is at least twice that of the second effective mean particle diameter, comprising administering an effective amount of the composition to the nose by administering a therapeutically effective amount of the composition to at least one nostril. In some embodiments, at least a portion of the therapeutically effective amount of the composition to each nostril. In some embodiments, the method comprises administering a first quantity of the composition to a first nostril, administering a second quantity of the composition to a second nostril, and optionally after a pre-selected time delay, administering a third quantity of the composition to the first nostril. In some embodiments, the method further comprises optionally after a pre-selected time delay, administering at least a fourth quantity of the composition to the second nostril. In some embodiments, the effective amount of the composition is effective to treat seizure, protect against seizure, reduce or ameliorate the intensity of seizure, reduce or ameliorate the frequency of seizure, and/or prevent occurrence or re-occurrence of seizure. In some embodiments, the effective amount of the composition is effective to provide a therapeutic effect selected from an anxiolytic effect, an anticonvulsant effect, a sedative effect, a skeletal muscle relaxant effect, an amnesic effect or combinations thereof. In some embodiments, a therapeutically effective plasma level of benzodiazepine drug is obtained within about 1 hours of administration to the patient. In some embodiments, the therapeutically effective plasma level of the benzodiazepine drug is obtained within about 30 minutes of administration of the composition to the patient. In some embodiments, the therapeutically effective plasma level of the benzodiazepine is obtained within about 15 minutes of administration of the composition to the patient. In some embodiments, the therapeutically effective plasma level of benzodiazepine drug is obtained within about 10 minutes of administration of the composition to the patient. In some embodiments, the therapeutically effective plasma level of benzodiazepine drug is obtained within about 5 minutes of administration of the composition to the patient. In some embodiments, a maximum (peak) plasma concentration ($C_{max}$) is obtained for the benzodiazepine drug at a time ($T_{max}$) less than about 1 hour after administration of the composition to a patient. In some embodiments, $T_{max}$ is less than about 30 minutes after administration of the composition to the patient. In some embodiments, $T_{max}$ is less than about 15 minutes after administration of the composition to the patient. In some embodiments, $T_{max}$ is less than about 12 minutes after administration of the composition to the patient. In some embodiments, a benzodiazepine plasma concentration curve having a first benzodiazepine plasma concentration maximum (Cmax1) and a second benzodiazepine plasma concentration maximum (Cmax2) is obtained. In some embodiments, the first benzodiazepine plasma concentration maximum (Cmax1) is obtained from 1 to 30 minutes after administration of the composition and the second benzodiazepine plasma concentration maximum (Cmax2) is obtained from 5 to 360 minutes after administration of the composition. In some embodiments, Cmax1 is obtained from 5 to 20 minutes after administration of the composition and Cmax2 is obtained from 10 to 60 minutes after administration. In some embodiments, Cmax1 and Cmax2 are obtained at times Tmax1 and Tmax2 that are at least about 5 minutes, at least about 10 minutes, at least about 20 minutes or at least about 30 minutes apart. In some embodiments, Cmax1 is obtained at time Tmax1 and Cmax2 is obtained at time Tmax2, wherein a difference between Tmax1 and Tmax2 is from 5 to 360, from 10 to 240, from 15 to 120 or from 20 to 60 minutes. In some embodiments, a benzodiazepine plasma concentration curve having a plasma benzodiazepine concentration maximum ($C_{max}$) and a shoulder ($C_{shoulder}$) is obtained. In some embodiments, the shoulder occurs within about 1 minute, within about 5 minutes, within about 10 minutes, within about 15 minutes or within about 30 minutes of time ($T_{max}$) when the concentration maximum ($C_{max}$) occurs. In some embodiments, a benzodiazepine plasma concentration curve having a single plasma benzodiazepine concentration maximum ($C_{max}$) is obtained. In some embodiments, Cmax is obtained within about 5 minutes, within about 10 minutes, within about 20 minutes, within about 30 minutes or within about 60 minutes of administering the medicament to the patient. in some embodiments, the plasma benzodiazepine concentration is in the range of 5 to 95% of $C_{max}$ from 30 to 720 minutes after the time ($T_{max}$) when $C_{max}$ is obtained. In some embodiments, the plasma benzodiazepine concentration is in the range of 5 to 95% of $C_{max}$ from 30 to 360 minutes after the time ($T_{max}$) when $C_{max}$ is obtained. In some embodiments, the plasma benzodiazepine concentration is in the range of 10 to 90 of $C_{max}$ from 30 to 720 minutes after the time ($T_{max}$) when $C_{max}$ is obtained. In some embodiments, the plasma benzodiazepine concentration is in the range of 10 to 90 of Cmax from 60 to 360 minutes after the time ($T_{max}$) when $C_{max}$ is obtained. In some embodiments, the plasma benzodiazepine concentration is in the range of 15 to 60% of $C_{max}$ from 30 to 720 minutes after the time ($T_{max}$) when $C_{max}$ is obtained. In some embodiments, the plasma benzodiazepine concentration is in the range of 15 to 60% of Cmax from 60 to 360 minutes after the time ($T_{max}$) when $C_{max}$ is obtained. In some embodiments, the plasma benzodiazepine concentration is in the range of 20 to 55% of $C_{max}$ from 30 to 720 minutes after the time ($T_{max}$) when $C_{max}$ is obtained. In some embodiments, the plasma benzodiazepine concentration is in the range of 20 to 55% of Cmax from 60 to 360 minutes after the time ($T_{max}$) when $C_{max}$ is obtained.

In some embodiments, the invention provides a pharmaceutical particulate composition for nasal delivery of a medicament comprising particulates having a multimodal particle size distribution. In some embodiments, the particulates have a bimodal particle size distribution. In some embodiments, the particulates have a trimodal or higher order modal particle size distribution. In some embodiments, the medicament comprises at least one benzodiazepine. In some embodiments, the medicament comprises at least one benzodiazepine selected from the group consisting of alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, medazepam, lorazepam, prazepam, quazepam, triazolam, temazepam, loprazolam, and pharmaceutically acceptable salts and combinations thereof. In some embodiments, at least one benzodiazepine drug comprises at least one member of the group consisting of alprazolam, diazepam, flurazepam, lorazepam, medazepam, mexazolam, midazolam, temazepam and pharmaceutically acceptable salts and combinations thereof. In some embodiments, at least one benzodiazepine drug comprises one or more members of the group consisting of diazepam, lorazepam, midazolam and pharmaceutically acceptable salts thereof. In some embodiments, the particles have an effective mean diameter greater than about 500 nm, 1000 nm, greater than about 2000 nm, greater than about 4000 nm or greater than 5000 nm. In some embodiments, the first population of particles, the second population of particles or both are coated with surface acting agent. In some embodiments, the surface acting agent is a cationic surfactant, a non-ionic surfactant, an anionic surfactant, a surface active biological modifier or a zwitterionic surfactant. In some embodiments, the second population of particles or both are coated with at least one surface acting agent. In some embodiments, at least one surface acting agent is a cationic surfactant, a non-ionic surfactant, an anionic surfactant, a surface active biological modifier or a zwitterionic surfactant. In some embodiments, at least one surface acting agent is a cationic surfactant selected from the group consisting of natural phospholipids, synthetic phospholipids, quaternary ammonium compounds, benzalkonium chloride, cetyltrimethylammonium bromide, chitosans, lauryldimethylbenzylammonium chloride, acyl carnitine hydrochlorides, dimethyldioctadecylammomium bromide (DDAB), dioleyoltrimethylammonium propane (DOTAP), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, and long-chain alkyl amines such as, for example, n-octylamine and oleylamine. In some embodiments, at least one surface acting agent is an anionic surface active agent selected from the group consisting of natural anionic phospholipids, synthetic anionic phospholipids and anionic polymers. In some embodiments, the natural anionic phospholipids, synthetic anionic phospholipids and anionic polymers are selected from the group consisting of polyacrylic acid, carrageenan k type II, carbopol 980, carbopol 974 P, carbopol 971 P, polycarbophil, sodium carboxymethylcellulose, sodium hyaluronate or combinations thereof. In some embodiments, at least one surface acting agent is selected from the group consisting of thiolated polymers. In some embodiments, the thiolated polymer is selected from the group consisting of cysteine conjugates of polyacrylic acid, polycarbophil (thiomer polycarbophil-cysteine), thiolated sodium carboxymethylcellulose, chitosan modified with 2-iminothiolate (e.g. chitosan-4-thiobutylamidine conjugates, chitosan-thioglycolic acid conjugates, chitosan-cysteine conjugates). In some embodiments, at least one surface acting agent is selected from the group consisting of polymeric mucilaginous polysaccharides. In some embodiments, the polymeric mucilaginous polysaccharide is from the aloe vera plant. In some embodiments, at least one surface agent is methylcellulose, ethylcellulose, hydroxypropylmethylcellulose (HPMC) or a mixture of two or more thereof. In some embodiments, the composition further comprises one or more additional ingredient selected from active pharmaceutical ingredients and enhancers. In some embodiments, the multimodal particle size distribution has a has first mode in the range of about 25 to about 4000 nm and a second mode in the range of about 500 to about 10,000 nm. In some embodiments, the multimodal particle size distribution has a first mode in the range of about 50 to about 2000 nm and a second mode in the range or about 1000 to about 10000 nm. In some embodiments, the first mode is greater than the second mode. In some embodiments, the first mode is in the range of about 50 to about 1000 nm and the second mode is in the range of about 1000 to about 10,000 nm. In some embodiments, the difference between the first and second modes is greater than about 100 nm, greater than about 200 nm, greater than about 500 nm, greater than about 1000 nm, greater than about 2000 nm, greater than about 3000 nm, greater than about 4000 nm, greater than about 5000 nm, greater than about 6000 nm, greater than about 7000 nm, greater than about 8000 nm, greater than about 9000 nm or greater than about 10,000 nm. In some embodiments, the difference between the mean particle size of the first and second particle populations is greater than about 10%, greater than about 20% or greater than about 30% of the mean particle diameter of the second population of particles. In some embodiments, the benzodiazepine particles do not contain solvent residues resulting from solvent extraction or solvent precipitation.

In some embodiments, the invention provides a method of using a pharmaceutical particulate composition for nasal delivery of a medicament comprising particulates having a multimodal particle size distribution, comprising administering an effective amount of the composition to the nose by administering a therapeutically effective amount of the composition to at least one nostril. In some embodiments, at least a portion of the therapeutically effective amount of the composition to each nostril. In some embodiments, the method comprises administering a first quantity of the composition to a first nostril, administering a second quantity of the composition to a second nostril, and optionally after a pre-selected time delay, administering a third quantity of the composition to the first nostril. In some embodiments, the method further comprises, optionally after a pre-selected time delay, administering at least a fourth quantity of the composition to the second nostril. In some embodiments, the effective amount of the composition is effective to treat seizure, protect against seizure, reduce or ameliorate the intensity of seizure, reduce or ameliorate the frequency of seizure, and/or prevent occurrence or re-occurrence of seizure. In some embodiments, the effective amount of the composition is effective to provide a therapeutic effect selected from an anxiolytic effect, an anti-convulsant effect, a sedative effect, a skeletal muscle relaxant effect, an amnesic effect or combinations thereof. In some embodiments, a therapeutically effective plasma level of benzodiazepine drug is obtained within about 1 hour of administration of the composition to a patient. In some embodiments, a therapeutically effective plasma level of the benzodiazepine drug is obtained within about 30 minutes of administration of the composition to the patient. In some embodiments, the therapeutically effective plasma level of the benzodiazepine is obtained within about 15 minutes of administration of the composition to the patient. In some embodiments, the therapeutically effective plasma level of benzodiazepine drug is obtained within about 10 minutes of administration of the composition to the patient. In some embodiments, the therapeutically effective plasma level of benzodiazepine drug is obtained within about 5 minutes of administration of the composition to the patient. In some embodiments, a peak plasma concentration ($C_{max}$) is achieved for the benzodiazepine drug at a time ($T_{max}$) less than about 1 hour after administration of the composition to a patient. In some embodiments, $T_{max}$ is less than about 30 minutes after administration of the composition to the patient. In some embodiments, $T_{max}$ is less than about 15 minutes after administration of the composition to the patient. In some embodiments, $T_{max}$ is less than about 12 minutes after administration of the composition to the patient. In some embodiments, the effective amount of the composition is effective to treat seizure, protect against seizure, reduce or ameliorate the intensity of seizure, reduce or ameliorate the frequency of seizure, and/or prevent occurrence or re-occurrence of seizure. In some embodiments, the effective amount of the composition is effective to provide a therapeutic effect selected from an anxiolytic effect, an anticonvulsant effect, a sedative effect, a skeletal muscle relaxant effect, an amnesic effect or combinations thereof. In some embodiments, a first benzodiazepine plasma concentration maximum (Cmax1) is obtained from 1 to 30 minutes after administration of the composition and a second benzodiazepine plasma concentration maximum (Cmax2) is obtained from 5 to 360 minutes after administration of the composition. In some embodiments, Cmax1 is obtained from 5 to 20 minutes after administration of the composition and Cmax2 is obtained from 10 to 60 minutes after administration. In some embodiments, Cmax1 and Cmax2 are obtained at times Tmax1 and Tmax2 that are at least about 5 minutes, at least about 10 minutes, at least about 20 minutes or at least about 30 minutes apart. In some embodiments, Cmax1 is obtained at time Tmax1 and Cmax2 is obtained at time Tmax2; and wherein Tmax1 and Tmax2 are from 5 to 360, from 10 to 240, from 15 to 120 or from 20 to 60 minutes apart. In some embodiments, a benzodiazepine plasma concentration curve having a concentration maximum ($C_{max}$) and a shoulder ($C_{shoulder}$) is obtained. In some embodiments, the shoulder occurs within about 1 minute, within about 5 minutes, within about 10 minutes, within about 15 minutes or within about 30 minutes of time ($T_{max}$) when the concentration maximum ($C_{max}$) occurs. In some embodiments, a benzodiazepine plasma concentration curve having a single plasma benzodiazepine concentration maximum ($C_{max}$) is obtained. In some embodiments, $C_{max}$ is obtained within about 5 minutes, within about 10 minutes, within about 20 minutes, within about 30 minutes or within about 60 minutes of administering the medicament to the patient. In some embodiments, the plasma benzodiazepine concentration is in the range of 5 to 95% of Cmax from 30 to 720 minutes after the time ($T_{max}$) when $C_{max}$ is obtained. In some embodiments, the plasma benzodiazepine concentration is in the range of 5 to 95% of $C_{max}$ from 30 to 360 minutes after the time ($T_{max}$) when $C_{max}$ is obtained. In some embodiments, the plasma benzodiazepine concentration is in the range of 10 to 90 of $C_{max}$ from 30 to 720 minutes after the time ($T_{max}$) when $C_{max}$ is obtained. In some embodiments, the plasma benzodiazepine concentration is in the range of 10 to 90 of $C_{max}$ from 60 to 360 minutes after the time ($T_{max}$) when $C_{max}$ is obtained. In some embodiments, the plasma benzodiazepine concentration is in the range of 15 to 60% of $C_{max}$ from 30 to 720 minutes after the time ($T_{max}$) when $C_{max}$ is obtained. In some embodiments, the plasma benzodiazepine concentration is in the range of 15 to 60% of $C_{max}$ from 60 to 360 minutes after the time ($T_{max}$) when $C_{max}$ is obtained. In some embodiments, the plasma benzodiazepine concentration is in the range of 20 to 55% of $C_{max}$ from 30 to 720 minutes after the time ($T_{max}$) when $C_{max}$ is obtained. In some embodiments, the plasma benzodiazepine concentration is in the range of 20 to 55% of $C_{max}$ from 60 to 360 minutes after the time ($T_{max}$) when $C_{max}$ is obtained.

In some embodiments, the invention provides an aerosol composition of an aqueous suspension or dispersion of nanoparticulate benzodiazepine particles, wherein: the droplets of the aerosol have a mass median aerodynamic diameter (MMAD) less than or equal to about 1000 μm and the nanoparticulate benzodiazepine particles have an effective average particle size of less than about 5000 nm. In some embodiments, the nanoparticulate benzodiazepine particles comprise at least one member of the group consisting of alprazolam, brotizolam, chlordiazep oxide, clobazam, clonazepam, clorazepam, demoxazepam, flumazenil, flurazepam, halazepam, midazolam, nordazepam, medazepam, diazepam, nitrazepam, oxazepam, medazepam, lorazepam, prazepam, quazepam, triazolam, temazepam, loprazolam, and pharmaceutically acceptable salts and combinations thereof. In some embodiments, the nanoparticulate benzodiazepine particles comprise at least one member of the group consisting of alprazolam, diazepam, flurazepam, lorazepam, medazepam, mexazolam, midazolam, temazepam and pharmaceutically acceptable salts and combinations thereof. In some embodiments, the nanoparticulate benzodiazepine particles comprise at least one benzodiazepine selected from the group consisting of diazepam, lorazepam, midazolam and pharmaceutically acceptable salts thereof. In some embodiments, the aerosol composition can be administered in a drug dosage in less than about 60 seconds. In some embodiments, the aerosol composition can be administered in a drug dosage in less than about 15 seconds. In some embodiments, the nanoparticulate benzodiazepine particles have an effective average particle size of about 50 nm to about 5000 nm. In some embodiments, the nanoparticulate diazepam benzodiazepine have an effective average particle size of about 50 nm to about 400 nm. In some embodiments, the nanoparticulate benzodiazepine particles have an effective average particle size of about 400 nm to about 5000 nm. In some embodiments, the droplets of the aerosol have a mass median aerodynamic diameter (MMAD) of less than or equal to about 1000 μm. In some embodiments, the benzodiazepine or pharmaceutically acceptable salt thereof is present in a concentration of from about 0.05 mg/mL up to about 600 mg/mL. In some embodiments, essentially each droplet of the aerosol comprises at least one nanoparticle. In some embodiments, the nanoparticulate benzodiazepine drug particles have an effective average particle size of less than about 400 nm. In some embodiments, the nanoparticulate benzodiazepine drug particles have an effective average particle size of less than about 300 nm, less than about 200 nm, less than about 100 nm or less than about 50 nm. In some embodiments, the nanoparticulate benzodiazepine drug particles further comprises at least one additional ingredient selected from active pharmaceutical ingredients and enhancers. In some embodiments, the nanoparticulate benzodiazepine drug particles further comprise at least one additional active pharmaceutical ingredient. In some embodiments, the nanoparticulate benzodiazepine drug particles further comprise at least one enhancer. In some embodiments, the droplets of the aerosol have a mass median aerodynamic diameter of from about 2 μm to about 10 μm. In some embodiments, the first population of particles, the second population of particles or both are coated with at least one surface acting agent. In some embodiments, at least one surface acting agent is a cationic surfactant, a non-ionic surfactant, an anionic surfactant, a surface active biological modifier or a zwitterionic surfactant. In some embodiments, at least one surface acting agent is a cationic surfactant selected from the group consisting of natural phospholipids, synthetic phospholipids, quaternary ammonium compounds, benzalkonium chloride, cetyltrimethylammonium bromide, chitosans, lauryldimethylbenzylammonium chloride, acyl carnitine hydrochlorides, dimethyldioctadecylammomium bromide (DDAB), dioleyoltrimethylammonium propane (DOTAP), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, and long-chain alkyl amines such as, for example, n-octylamine and oleylamine. In some embodiments, at least one surface acting agent is an anionic surface active agent selected from the group consisting of natural anionic phospholipids, synthetic anionic phospholipids and anionic polymers. In some embodiments, the natural anionic phospholipids, synthetic anionic phospholipids and anionic polymers are selected from the group consisting of polyacrylic acid, carrageenan k type II, carbopol 980, carbopol 974 P, carbopol 971 P, polycarbophil, sodium carboxymethylcellulose, sodium hyaluronate or combinations thereof. In some embodiments, at least one surface acting agent is selected from the group consisting of thiolated polymers. In some embodiments, the thiolated polymer is selected from the group consisting of cysteine conjugates of polyacrylic acid, polycarbophil (thiomer polycarbophil-cysteine), thiolated sodium carboxymethylcellulose, chitosan modified with 2-iminothiolate (e.g. chitosan-4-thiobutylamidine conjugates, chitosan-thioglycolic acid conjugates, chitosan-cysteine conjugates). In some embodiments, at least one surface acting agent is selected from the group consisting of polymeric mucilaginous polysaccharides. In some embodiments, the polymeric mucilaginous polysaccharide is from the aloe vera plant. In some embodiments, at least one surface acting agent is methylcellulose, ethylcellulose, hydroxypropylmethylcellulose (HPMC) or a mixture of two or more thereof.

In some embodiments, the invention provides a method using an aerosol composition of an aqueous suspension or dispersion of nanoparticulate benzodiazepine particles, wherein: the droplets of the aerosol have a mass median aerodynamic diameter (MMAD) less than or equal to about 1000 μm and the nanoparticulate benzodiazepine particles have an effective average particle size of less than about 5000 nm, the method comprising administering an effective amount of the composition to the nose by spraying a therapeutically effective amount of the composition into at least one nostril. In some embodiments, the method comprises spraying at least a portion of the therapeutically effective amount of the composition into each nostril. In some embodiments, the method comprises spraying a first quantity of the composition into the first nostril, spraying a second quantity of the composition into a second nostril, and optionally after a pre-selected time delay, spraying a third quantity of the composition into the first nostril. In some embodiments, the method further comprises, optionally after a pre-selected time delay, administering at least a fourth quantity of the composition to the second nostril. In some embodiments, the effective amount of the composition is effective to treat seizure, protect against seizure, reduce or ameliorate the intensity of seizure, reduce or ameliorate the frequency of seizure, and/or prevent occurrence or re-occurrence of seizure. In some embodiments, the effective amount of the composition is effective to provide a therapeutic effect selected from an anxiolytic effect, an anticonvulsant effect, a sedative effect, a skeletal muscle relaxant effect, an amnesic effect or combinations thereof. In some embodiments, a therapeutically effective plasma level of benzodiazepine drug is obtained within about 1 hour of administration of the composition to a patient. In some embodiments, the therapeutically effective plasma level of the benzodiazepine drug is obtained within about 30 minutes of administration of the composition to the patient. In some embodiments, the therapeutically effective plasma level of the benzodiazepine is obtained within about 15 minutes of administration of the composition to the patient. In some embodiments, the therapeutically effective plasma level of benzodiazepine drug is obtained within about 10 minutes of administration of the composition to the patient. In some embodiments, the therapeutically effective plasma level of benzodiazepine drug is obtained within about 5 minutes of administration of the composition to the patient. In some embodiments, peak plasma concentration ($C_{max}$) is achieved for the benzodiazepine drug at a time ($T_{max}$) less than about 1 hour after administration of the composition to a patient. In some embodiments, $T_{max}$ is less than about 30 minutes after administration of the composition to the patient. In some embodiments, $T_{max}$ is less than about 15 minutes after administration of the composition to the patient. In some embodiments, $T_{max}$ is less than about 12 minutes after administration of the composition to the patient.

In some embodiments, the invention provides a method of administering a benzodiazepine drug to a patient, comprising administering to the nose or nasal cavity an effective amount of an aerosol composition of an aqueous suspension or dispersion of nanoparticulate benzodiazepine particles, wherein: the droplets of the aerosol have a mass median aerodynamic diameter (MMAD) less than or equal to about 1000 μm and the nanoparticulate benzodiazepine particles have an effective average particle size of less than about 5000 nm. In some embodiments, the nanoparticulate benzodiazepine particles comprise at least on member of the group consisting of alprazolam, brotizolam, chlordiazep oxide, clobazam, clonazepam, clorazepam, demoxazepam, flumazenil, flurazepam, halazepam, midazolam, nordazepam, medazepam, diazepam, nitrazepam, oxazepam, medazepam, lorazepam, prazepam, quazepam, triazolam, temazepam, loprazolam, and pharmaceutically acceptable salts and combinations thereof. In some embodiments, the nanoparticulate benzodiazepine particles comprise at least one member of the group consisting of alprazolam, diazepam, flurazepam, lorazepam, medazepam, mexazolam, midazolam, temazepam and pharmaceutically acceptable salts and combinations thereof. In some embodiments, the nanoparticulate benzodiazepine particles comprise at least one benzodiazepine selected from the group consisting of diazepam, lorazepam, midazolam and pharmaceutically acceptable salts thereof. In some embodiments, the aerosol composition is administered in a drug dosage in less than about 60 seconds. In some embodiments, the aerosol composition is administered in a drug dosage in less than about 15 seconds. In some embodiments, the nanoparticulate benzodiazepine particles have an effective average particle size of less than about 5000 nm. In some embodiments, the nanoparticulate benzodiazepine particles have an effective average particle size of less than about 1000 nm. In some embodiments, the droplets of the aerosol have a mass median aerodynamic diameter (MMAD) of less than or equal to about 100 μm. In some embodiments, the benzodiazepine is present in a concentration of from about 0.05 mg/mL up to about 600 mg/mL. In some embodiments, essentially each droplet of the aerosol comprises at least one nanoparticle.

In some embodiments, the nanoparticulate benzodiazepine drug particles have an effective average particle size of less than about 400 nm, less than about 300 nm, less than about 200 nm, less than about 100 nm or less than about 50 nm. In some embodiments, the droplets of the aerosol have a mass median aerodynamic diameter of from about 2 to about 10 μm. In some embodiments, the effective amount of the composition is effective to treat seizure, protect against seizure, reduce or ameliorate the intensity of seizure, reduce or ameliorate the frequency of seizure, and/or prevent occurrence or re-occurrence of seizure. In some embodiments, the effective amount of the composition is effective to provide a therapeutic effect selected from an anxiolytic effect, an anticonvulsant effect, a sedative effect, a skeletal muscle relaxant effect, an amnesic effect or combinations thereof. In some embodiments, a therapeutically effective plasma level of benzodiazepine drug is obtained within about 1 hour of administration of the composition to a patient. In some embodiments, the therapeutically effective plasma level of the benzodiazepine drug is obtained within about 30 minutes of administration of the composition to the patient. In some embodiments, the therapeutically effective plasma level of the benzodiazepine is obtained within about 15 minutes, within about 10 minutes or within about 5 minutes of administration of the composition to the patient. In some embodiments, peak plasma concentration ($C_{max}$) is achieved for the benzodiazepine drug at a time ($T_{max}$) less than about 1 hour after administration of the composition to a patient. In some embodiments, $T_{max}$ is less than about 30 minutes after administration of the composition to the patient. In some embodiments, $T_{max}$ is less than about 15 minutes after administration of the composition to the patient. In some embodiments, $T_{max}$ is less than about 12 minutes after administration of the composition to the patient.

In some embodiments, the invention provides a pharmaceutical composition for aerosol (e.g. nasal or pulmonary) administration of benzodiazepine comprising benzodiazepine particles and one or more non-cationic surface active agents adsorbed to a surface thereof. In some embodiments, the nanoparticulate benzodiazepine particles comprise at least one member of the group consisting of alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, medazepam, lorazepam, prazepam, quazepam, triazolam, temazepam, loprazolam, and pharmaceutically acceptable salts and combinations thereof. In some embodiments, the benzodiazepine particles comprise at least one member of the group consisting of alprazolam, diazepam, flurazepam, lorazepam, medazepam, mexazolam, midazolam, temazepam and pharmaceutically acceptable salts and combinations thereof. In some embodiments, the nanoparticulate comprise at least one benzodiazepine selected from the group consisting of diazepam, lorazepam, midazolam and pharmaceutically acceptable salts thereof. In some embodiments, the pharmaceutical composition is in the form of an aqueous suspension or dispersion. In some embodiments, the pharmaceutical composition is in the form of a spray powder. in some embodiments, the benzodiazepine particles contain crystalline benzodiazepine, amorphous benzodiazepine, semi-crystalline benzodiazepine, a mixture of amorphous and crystalline benzodiazepine, a mixture of amorphous and semi-crystalline benzodiazepine, a mixture of crystalline and semi-crystalline benzodiazepine or a mixture of amorphous, crystalline and semi-crystalline diazepine. In some embodiments, the benzodiazepine particles contain crystalline diazepam, amorphous diazepam, semi-crystalline diazepam, a mixture of amorphous and crystalline diazepam, a mixture of amorphous and semi-crystalline diazepam, a mixture of crystalline and semi-crystalline diazepam, a mixture of amorphous, crystalline and semi-crystalline diazepam, crystalline lorazepam, amorphous lorazepam, semi-crystalline lorazepam, a mixture of amorphous and crystalline lorazepam, a mixture of amorphous and semi-crystalline lorazepam, a mixture of crystalline and semi-crystalline lorazepam, a mixture of amorphous, crystalline and semi-crystalline lorazepam, crystalline medazepam, amorphous medazepam, semi-crystalline medazepam, a mixture of amorphous and crystalline medazepam, a mixture of amorphous and semi-crystalline medazepam, a mixture of crystalline and semi-crystalline medazepam and a mixture of amorphous, crystalline and semi-crystalline medazepam. In some embodiments, the benzodiazepine particles have a mean particle size of less than about 5000 nm. In some embodiments, the benzodiazepine particles have a mean particle size of approximately 1000 nm. In some embodiments, the benzodiazepine particles have adsorbed to a surface thereof one or more surface active agents selected from the group consisting of cationic surfactants, anionic surfactants, zwitterionic surfactants, surface active biological modifiers and nonionic surfactants. In some embodiments, the benzodiazepine particles adsorb to a biological surface. In some embodiments, at least one surface acting agent is a cationic surfactant selected from the group consisting of natural phospholipids, synthetic phospholipids, quaternary ammonium compounds, benzalkonium chloride, cetyltrimethylammonium bromide, chitosans, lauryldimethylbenzylammonium chloride, acyl carnitine hydrochlorides, dimethyldioctadecylammomium bromide (DDAB), dioleyoltrimethylammonium propane (DOTAP), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, and long-chain alkyl amines such as, for example, n-octylamine and oleylamine. In some embodiments, at least one surface active agent is an anionic surfactant selected from the group consisting of natural anionic phospholipids, synthetic anionic phospholipids and anionic polymers. In some embodiments, the natural anionic phospholipids, synthetic anionic phospholipids and anionic polymers are selected from the group consisting of polyacrylic acid, carrageenan k type II, carbopol 980, carbopol 974 P, carbopol 971 P, polycarbophil, sodium carboxymethylcellulose, sodium hyaluronate or combinations thereof. In some embodiments, at least one surface active agents is selected from the group consisting of thiolated polymers. In some embodiments, the thiolated polymer is selected from the group consisting of cysteine conjugates of polyacrylic acid, polycarbophil (thiomer polycarbophil-cysteine), thiolated sodium carboxymethylcellulose, chitosan modified with 2-iminothiolate (e.g. chitosan-4-thiobutylamidine conjugates, chitosan-thioglycolic acid conjugates, chitosan-cysteine conjugates). In some embodiments, at least one surface active agents is selected from the group consisting of polymeric mucilaginous polysaccharides. In some embodiments, the polymeric mucilaginous polysaccharide is from the aloe vera plant. In some embodiments, at least one surface active agents is methylcellulose, ethylcellulose, hydroxypropylmethyl-cellulose (HPMC) or a mixture of two or more thereof. In some embodiments, the benzodiazepine particles do not contain solvent residues resulting from solvent extraction or solvent precipitation. In some embodiments, the composition further comprises one or more additional ingredient selected from active pharmaceutical ingredients and enhancers.

In some embodiments, the invention provides a method of administering a pharmaceutical composition for aerosol (e.g. nasal or pulmonary) administration of benzodiazepine comprising benzodiazepine particles and one or more non-cationic surface active agents adsorbed to a surface thereof, the method comprising administering an effective amount of the composition to a patient via a suitable administration route (e.g. nasal or pulmonary). In some embodiments, the method comprises administering the composition to the nose by administering a therapeutically effective amount of the composition to at least one nostril. In some embodiments, at least a portion of the therapeutically effective amount of the composition to each nostril. In some embodiments, the method comprises administering a first quantity of the composition to a first nostril, administering a second quantity of the composition to a second nostril, and optionally after a pre-selected time delay, administering a third quantity of the composition to the first nostril. In some embodiments, the invention further comprises, optionally after a pre-selected time delay, administering at least a fourth quantity of the composition to the second nostril. In some embodiments, the method comprises administering the composition by a pulmonary route, e.g. with a nebulizer, a dry powder inhaler (DPI) or a metered dose inhaler (MDI). In some embodiments, the effective amount of the composition is effective to treat seizure, protect against seizure, reduce or ameliorate the intensity of seizure, reduce or ameliorate the frequency of seizure, and/or prevent occurrence or reoccurrence of seizure. In some embodiments, the effective amount of the composition is effective to provide a therapeutic effect selected from an anxiolytic effect, an anticonvulsant effect, a sedative effect, a skeletal muscle relaxant effect, an amnesic effect or combinations thereof. In some embodiments, a therapeutically effective plasma level of benzodiazepine drug is obtained within about 1 hour of administration of the composition to a patient. In some embodiments, the therapeutically effective plasma level of the benzodiazepine drug is obtained within about 30 minutes of administration of the composition to the patient. In some embodiments, the therapeutically effective plasma level of the benzodiazepine is obtained within about 15 minutes of administration of the composition to the patient. In some embodiments, the therapeutically effective plasma level of benzodiazepine drug is obtained within about 10 minutes of administration of the composition to the patient. In some embodiments, the therapeutically effective plasma level of benzodiazepine drug is obtained within about 5 minutes of administration of the composition to the patient. In some embodiments, peak plasma concentration ($C_{max}$) is achieved for the benzodiazepine drug at a time ($T_{max}$) less than about 1 hour after administration of the composition to a patient. In some embodiments, $T_{max}$ is less than about 30 minutes after administration of the composition to the patient. In some embodiments, $T_{max}$ is less than about 15 minutes after administration of the composition to the patient. In some embodiments, $T_{max}$ is less than about 12 minutes after administration of the composition to the patient.

The invention further provides a method of administering a benzodiazepine drug to a patient, comprising administering to the patient's nose or nasal cavity a pharmaceutical composition comprising particles of a benzodiazepine drug having a surface active agent adsorbed to a surface thereof. In some embodiments, at least one surface active agent is a cationic surfactant or a non-cationic surfactant. In some embodiments, at least one surface active agent is a cationic surfactant selected from the group consisting of natural phospholipids, synthetic phospholipids, quaternary ammonium compounds, benzalkonium chloride, cetyltrimethylammonium bromide, chitosans, lauryldimethylbenzylammonium chloride, acyl carnitine hydrochlorides, dimethyldioctadecylammomium bromide (DDAB), dioleyoltrimethylammonium propane (DOTAP), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, and long-chain alkyl amines such as, for example, n-octylamine and oleylamine. In some embodiments, at least one surface active agent is a non-cationic surfactant selected from the group consisting of anionic surfactants, non-ionic surfactants, surface active biological modifiers and zwitterionic surfactants. In some embodiments, at least one non-cationic surfactant is anionic surfactant selected from the group consisting of natural anionic phospholipids, synthetic anionic phospholipids and anionic polymers. In some embodiments, the natural anionic phospholipids, synthetic anionic phospholipids and anionic polymers are selected from the group consisting of polyacrylic acid, carrageenan k type II, carbopol 980, carbopol 974 P, carbopol 971 P, polycarbophil, sodium carboxymethylcellulose, sodium hyaluronate or combinations thereof. In some embodiments, at least one surface active agents is selected from the group consisting of thiolated polymers. In some embodiments, the thiolated polymer is selected from the group consisting of cysteine conjugates of polyacrylic acid, polycarbophil (thiomer polycarbophil-cysteine), thiolated sodium carboxymethylcellulose, chitosan modified with 2-iminothiolate (e.g. chitosan-4-thiobutylamidine conjugates, chitosan-thioglycolic acid conjugates, chitosan-cysteine conjugates). In some embodiments, at least one surface active agents is selected from the group consisting of polymeric mucilaginous polysaccharides. In some embodiments, the polymeric mucilaginous polysaccharide is from the aloe vera plant. In some embodiments, at least one surface active agents is methylcellulose, ethylcellulose, hydroxypropylmethylcellulose (HPMC) or a mixture of two or more thereof. In some embodiments, the nanoparticulate benzodiazepine particles comprise at least one member of the group consisting of alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, medazepam, lorazepam, prazepam, quazepam, triazolam, temazepam, loprazolam, and pharmaceutically acceptable salts and combinations thereof. In some embodiments, the benzodiazepine drug comprises at least one member of the group consisting of alprazolam, diazepam, flurazepam, lorazepam, medazepam, mexazolam, midazolam, temazepam and pharmaceutically acceptable salts and combinations thereof. In some embodiments, the benzodiazepine drug comprises one or more members of the group consisting of diazepam, lorazepam, midazolam and pharmaceutically acceptable salts thereof. In some embodiments, the benzodiazepine drug is in the form of an aqueous suspension or dispersion. In some embodiments, the benzodiazepine drug is in the form of a spray powder. In some embodiments, the benzodiazepine particles contain crystalline benzodiazepine, amorphous benzodiazepine, semi-crystalline benzodiazepine, a mixture of amorphous and crystalline benzodiazepine, a mixture of amorphous and semi-crystalline benzodiazepine, a mixture of crystalline and semi-crystalline benzodiazepine and a mixture of amorphous, crystalline and semi-crystalline benzodiazepine. In some embodiments, the benzodiazepine particles contain crystalline diazepam, amorphous diazepam, semi-crystalline diazepam, a mixture of amorphous and crystalline diazepam, a mixture of amorphous and semi-crystalline diazepam, a mixture of crystalline and semi-crystalline diazepam, a mixture of amorphous, crystalline and semi-crystalline diazepam, crystalline lorazepam, amorphous lorazepam, semi-crystalline lorazepam, a mixture of amorphous and crystalline lorazepam, a mixture of amorphous and semi-crystalline lorazepam, a mixture of crystalline and semi-crystalline lorazepam, a mixture of amorphous, crystalline and semi-crystalline lorazepam, crystalline medazepam, amorphous medazepam, semi-crystalline medazepam, a mixture of amorphous and crystalline medazepam, a mixture of amorphous and semi-crystalline medazepam, a mixture of crystalline and semi-crystalline medazepam and a mixture of amorphous, crystalline and semi-crystalline medazepam. In some embodiments, the benzodiazepine particles have a mean particle size of less than about 5000 nm. In some embodiments, the benzodiazepine particles have a mean particle size of less than about 4000 nm. In some embodiments, the benzodiazepine particles have a mean particle size in the range of about 50 to 5000 nm, about 100 to about 2500 nm, about 250 to about 1000 nm or approximately 500 nm. In some embodiments, the benzodiazepine particles do not contain solvent residues resulting from solvent extraction or solvent precipitation. In some embodiments, the benzodiazepine particles further comprise at least one additional ingredient selected from active pharmaceutical ingredients and enhancers. In some embodiments, the effective amount of the composition is effective to treat seizure, protect against seizure, reduce or ameliorate the intensity of seizure, reduce or ameliorate the frequency of seizure, and/or prevent occurrence or re-occurrence of seizure. In some embodiments, the effective amount of the composition is effective to provide a therapeutic effect selected from an anxiolytic effect, an anticonvulsant effect, a sedative effect, a skeletal muscle relaxant effect, an amnesic effect or combinations thereof. In some embodiments, a therapeutically effective plasma level of benzodiazepine drug is obtained within about 1 hour of administration of the composition to a patient. In some embodiments, the therapeutically effective plasma level of the benzodiazepine drug is obtained within about 30 minutes of administration of the composition to the patient. In some embodiments, the therapeutically effective plasma level of the benzodiazepine is obtained within about 15 minutes of administration of the composition to the patient. In some embodiments, the therapeutically effective plasma level of benzodiazepine drug is obtained within about 10 minutes of administration of the composition to the patient. In some embodiments, the therapeutically effective plasma level of benzodiazepine drug is obtained within about 5 minutes of administration of the composition to the patient. In some embodiments, peak plasma concentration ($C_{max}$) is achieved for the benzodiazepine drug at a time ($T_{max}$) less than about 1 hour after administration of the composition to a patient. In some embodiments, $T_{max}$ is less than about 30 minutes after administration of the composition to the patient. In some embodiments, $T_{max}$ is less than about 15 minutes after administration of the composition to the patient. In some embodiments, $T_{max}$ is less than about 12 minutes after administration of the composition to the patient.

The invention further provides a method of administering a benzodiazepine drug to a patient, comprising administering to the patient's lungs a pharmaceutical composition comprising particles of a benzodiazepine drug having a surface active agent adsorbed to a surface thereof. In some embodiments, at least one surface active agent is a cationic surfactant or a non-cationic surfactant. In some embodiments, at least one surface active agent is a cationic surfactant selected from the group consisting of natural phospholipids, synthetic phospholipids, quaternary ammonium compounds, benzalkonium chloride, cetyltrimethylammonium bromide, chitosans, lauryldimethylbenzylammonium chloride, acyl carnitine hydrochlorides, dimethyldioctadecylammomium bromide (DDAB), dioleyoltrimethylammonium propane (DOTAP), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, and long-chain alkyl amines such as, for example, n-octylamine and oleylamine. In some embodiments, at least one surface active agent is a non-cationic surfactant selected from the group consisting of anionic surfactants, non-ionic surfactants, surface active biological modifiers and zwitterionic surfactants. In some embodiments, at least one non-cationic surfactant is anionic surfactant selected from the group consisting of natural anionic phospholipids, synthetic anionic phospholipids and anionic polymers. In some embodiments, the natural anionic phospholipids, synthetic anionic phospholipids and anionic polymers are selected from the group consisting of polyacrylic acid, carrageenan k type II, carbopol 980, carbopol 974 P, carbopol 971 P, polycarbophil, sodium carboxymethylcellulose, sodium hyaluronate or combinations thereof. In some embodiments, at least one surface active agents is selected from the group consisting of thiolated polymers. In some embodiments, the thiolated polymer is selected from the group consisting of cysteine conjugates of polyacrylic acid, polycarbophil (thiomer polycarbophil-cysteine), thiolated sodium carboxymethylcellulose, chitosan modified with 2-iminothiolate (e.g. chitosan-4-thiobutylamidine conjugates, chitosan-thioglycolic acid conjugates, chitosan-cysteine conjugates). In some embodiments, at least one surface active agents is selected from the group consisting of polymeric mucilaginous polysaccharides. In some embodiments, the polymeric mucilaginous polysaccharide is from the aloe vera plant. In some embodiments, at least one surface active agents is methylcellulose, ethylcellulose, hydroxypropylmethylcellulose (HPMC) or a mixture of two or more thereof. In some embodiments, the nanoparticulate benzodiazepine particles comprise at least one member of the group consisting of alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, medazepam, lorazepam, prazepam, quazepam, triazolam, temazepam, loprazolam, and pharmaceutically acceptable salts and combinations thereof. In some embodiments, the benzodiazepine drug comprises at least one member of the group consisting of alprazolam, diazepam, flurazepam, lorazepam, medazepam, mexazolam, midazolam, temazepam and pharmaceutically acceptable salts and combinations thereof. In some embodiments, the benzodiazepine drug comprises one or more members of the group consisting of diazepam, lorazepam, midazolam and pharmaceutically acceptable salts thereof. In some embodiments, the benzodiazepine drug is in the form of an aqueous suspension or dispersion. In some embodiments, the benzodiazepine drug is in the form of a spray powder. In some embodiments, the benzodiazepine particles contain crystalline benzodiazepine, amorphous benzodiazepine, semi-crystalline benzodiazepine, a mixture of amorphous and crystalline benzodiazepine, a mixture of amorphous and semi-crystalline benzodiazepine, a mixture of crystalline and semi-crystalline benzodiazepine and a mixture of amorphous, crystalline and semi-crystalline benzodiazepine. In some embodiments, the benzodiazepine particles contain crystalline diazepam, amorphous diazepam, semi-crystalline diazepam, a mixture of amorphous and crystalline diazepam, a mixture of amorphous and semi-crystalline diazepam, a mixture of crystalline and semi-crystalline diazepam, a mixture of amorphous, crystalline and semi-crystalline diazepam, crystalline lorazepam, amorphous lorazepam, semi-crystalline lorazepam, a mixture of amorphous and crystalline lorazepam, a mixture of amorphous and semi-crystalline lorazepam, a mixture of crystalline and semi-crystalline lorazepam, a mixture of amorphous, crystalline and semi-crystalline lorazepam, crystalline medazepam, amorphous medazepam, semi-crystalline medazepam, a mixture of amorphous and crystalline medazepam, a mixture of amorphous and semi-crystalline medazepam, a mixture of crystalline and semi-crystalline medazepam and a mixture of amorphous, crystalline and semi-crystalline medazepam. In some embodiments, the benzodiazepine particles have a mean particle size of less than about 5000 nm. In some embodiments, the benzodiazepine particles have a mean particle size of less than about 4000 nm. In some embodiments, the benzodiazepine particles have a mean particle size in the range of about 50 to 5000 nm, about 100 to about 2500 nm, about 250 to about 1000 nm or approximately 500 nm. In some embodiments, the benzodiazepine particles do not contain solvent residues resulting from solvent extraction or solvent precipitation. In some embodiments, the benzodiazepine particles further comprise at least one additional ingredient selected from active pharmaceutical ingredients and enhancers. In some embodiments, the effective amount of the composition is effective to treat seizure, protect against seizure, reduce or ameliorate the intensity of seizure, reduce or ameliorate the frequency of seizure, and/or prevent occurrence or re-occurrence of seizure. In some embodiments, the effective amount of the composition is effective to provide a therapeutic effect selected from an anxiolytic effect, an anticonvulsant effect, a sedative effect, a skeletal muscle relaxant effect, an amnesic effect or combinations thereof. In some embodiments, a therapeutically effective plasma level of benzodiazepine drug is obtained within about 1 hour of administration of the composition to a patient. In some embodiments, the therapeutically effective plasma level of the benzodiazepine drug is obtained within about 30 minutes of administration of the composition to the patient. In some embodiments, the therapeutically effective plasma level of the benzodiazepine is obtained within about 15 minutes of administration of the composition to the patient. In some embodiments, the therapeutically effective plasma level of benzodiazepine drug is obtained within about 10 minutes of administration of the composition to the patient. In some embodiments, the therapeutically effective plasma level of benzodiazepine drug is obtained within about 5 minutes of administration of the composition to the patient. In some embodiments, peak plasma concentration ($C_{max}$) is achieved for the benzodiazepine drug at a time ($T_{max}$) less than about 1 hour after administration of the composition to a patient. In some embodiments, $T_{max}$ is less than about 30 minutes after administration of the composition to the patient. In some embodiments, $T_{max}$ is less than about 15 minutes after administration of the composition to the patient. In some embodiments, $T_{max}$ is less than about 12 minutes after administration of the composition to the patient.

In some embodiments, the invention provides a non-aqueous dispersion or suspension of nanoparticulate benzodiazepine particles. In some embodiments, the nanoparticulate benzodiazepine particles comprise at least one member of the group consisting of alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, medazepam, lorazepam, prazepam, quazepam, triazolam, temazepam, loprazolam, and pharmaceutically acceptable salts and combinations thereof. In some embodiments, the nanoparticulate benzodiazepine particles comprise at least one member of the group consisting of alprazolam, diazepam, flurazepam, lorazepam, medazepam, mexazolam, midazolam, temazepam and pharmaceutically acceptable salts and combinations thereof. In some embodiments, the nanoparticulate benzodiazepine particles comprise at least one benzodiazepine selected from the group consisting of diazepam, lorazepam, midazolam and pharmaceutically acceptable salts thereof. In some embodiments, the droplets have a mass median aerodynamic diameter (MMAD) less than or equal to about 1000 μm and the nanoparticulate benzodiazepine particles have an effective average particle size of less than about 5000 nm. In some embodiments, the nanoparticulate benzodiazepine particles have an effective average particle size of less than about 1000 nm, less than about 500 nm, less than about 400 nm, less than about 250 nm, less than about 100 nm or less than about 50 nm. In some embodiments, the nanoparticulate benzodiazepine particles have an effective average particle size in the range of about 25 to about 10000 nm. In some embodiments, the nanoparticulate benzodiazepine particles have an effective average particle size of about 50 to about 5000 nm. In some embodiments, the nanoparticulate benzodiazepine particles have an effective average particle size of about 500 nm to about 5000 nm. In some embodiments, the non-aqueous dispersion or suspension is adapted for nasal administration. In some embodiments, the non-aqueous dispersion or suspension is adapted for pulmonary delivery. In some embodiments, the dispersion or suspension further comprises at least one additional ingredient selected from the group consisting of active pharmaceutical ingredients and enhancers. In some embodiments, the composition further comprises a non-aqueous carrier or propellant. In some embodiments, the non-aqueous carrier or propellant comprises a hydrocarbon, a hydrofluorocarbon or a chlorofluorocarbon. In some embodiments, at least a portion of the particles is coated with at least one surface acting agent. In some embodiments, at least one surface acting agent is a cationic surfactant, a non-ionic surfactant, an anionic surfactant, a surface active biological modifier or a zwitterionic surfactant. In some embodiments, at least one surface acting agent is a cationic surfactant selected from the group consisting of natural phospholipids, synthetic phospholipids, quaternary ammonium compounds, benzalkonium chloride, cetyltrimethylammonium bromide, chitosans, lauryldimethylbenzyl-ammonium chloride, acyl carnitine hydrochlorides, dimethyldioctadecylammomium bromide (DDAB), dioleyoltrimethylammonium propane (DOTAP), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, and long-chain alkyl amines such as, for example, n-octylamine and oleylamine. In some embodiments, at least one surface acting agent is an anionic surface active agent selected from the group consisting of natural anionic phospholipids, synthetic anionic phospholipids and anionic polymers. In some embodiments, the natural anionic phospholipids, synthetic anionic phospholipids and anionic polymers are selected from the group consisting of polyacrylic acid, carrageenan k type II, carbopol 980, carbopol 974 P, carbopol 971 P, polycarbophil, sodium carboxymethylcellulose, sodium hyaluronate or combinations thereof. In some embodiments, at least one surface acting agent is selected from the group consisting of thiolated polymers. In some embodiments, the thiolated polymer is selected from the group consisting of cysteine conjugates of polyacrylic acid, polycarbophil (thiomer polycarbophil-cysteine), thiolated sodium carboxymethylcellulose, chitosan modified with 2-iminothiolate (e.g. chitosan-4-thiobutylamidine conjugates, chitosan-thioglycolic acid conjugates, chitosan-cysteine conjugates). In some embodiments, at least one surface acting agent is selected from the group consisting of polymeric mucilaginous polysaccharides. In some embodiments, the polymeric mucilaginous polysaccharide is from the aloe vera plant. In some embodiments, at least one surface acting agent is methylcellulose, ethylcellulose, hydroxypropylmethylcellulose (HPMC) or a mixture of two or more thereof. In some embodiments, the nanoparticulate benzodiazepine has a multimodal particle size distribution. In some embodiments, the nanoparticulate benzodiazepine has a bimodal particle size distribution. In some embodiments, the nanoparticulate benzodiazepine has a trimodal or higher order modal particle size distribution.

In some embodiments, the invention provides a method of using a non-aqueous dispersion or suspension of nanoparticulate benzodiazepine, comprising administering an effective amount of the dispersion or suspension to a patient. In some embodiments, the method comprises administering a therapeutically effective amount of the composition to at least one nostril of the patient. In some embodiments, the method comprises administering at least a portion of the therapeutically effective amount of the composition to each nostril. In some embodiments, the method comprises administering a first quantity of the composition to a first nostril, administering a second quantity of the composition to a second nostril, and optionally after a pre-selected time delay, administering a third quantity of the composition to the first nostril. In some embodiments, the method further comprises, optionally after a pre-selected time delay, administering at least a fourth quantity of the composition to the second nostril. In some embodiments, the method comprises pulmonary administration of a therapeutically effective amount of the composition to a patient. In some embodiments, the effective amount of the composition is effective to treat seizure, protect against seizure, reduce or ameliorate the intensity of seizure, reduce or ameliorate the frequency of seizure, and/or prevent occurrence or re-occurrence of seizure. In some embodiments, the effective amount of the composition is effective to provide a therapeutic effect selected from an anxiolytic effect, an anticonvulsant effect, a sedative effect, a skeletal muscle relaxant effect, an amnesic effect or combinations thereof. In some embodiments, a therapeutically effective plasma level of benzodiazepine drug is obtained within about 1 hour of administration of the composition to a patient. In some embodiments, the therapeutically effective plasma level of the benzodiazepine drug is obtained within about 30 minutes of administration of the composition to the patient. In some embodiments, the therapeutically effective plasma level of the benzodiazepine is obtained within about 15 minutes of administration of the composition to the patient. In some embodiments, the therapeutically effective plasma level of benzodiazepine drug is obtained within about 10 minutes of administration of the composition to the patient. In some embodiments, the therapeutically effective plasma level of benzodiazepine drug is obtained within about 5 minutes of administration of the composition to the patient. In some embodiments, peak plasma concentration ($C_{max}$) is achieved for the benzodiazepine drug at a time ($T_{max}$) less than about 1 hour after administration of the composition to a patient. In some embodiments, $T_{max}$ is less than about 30 minutes after administration of the composition to the patient. In some embodiments, $T_{max}$ is less than about 15 minutes after administration of the composition to the patient. In some embodiments, $T_{max}$ is less than about 12 minutes after administration of the composition to the patient.

In some embodiments, the invention provides a method of administering a benzodiazepine drug to a patient, comprising administering to the patient a pharmaceutical composition comprising a non-aqueous dispersion or suspension of nanoparticulate benzodiazepine particles. In some embodiments, the composition is administered to the patient's nose or nasal cavity. In some embodiments, the composition is administered by pulmonary delivery. In some embodiments, the nanoparticulate benzodiazepine particles comprise at least one member of the group consisting of alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, medazepam, lorazepam, prazepam, quazepam, triazolam, temazepam, loprazolam, and pharmaceutically acceptable salts and combinations thereof. In some embodiments, the benzodiazepine drug comprises at least one member of the group consisting of alprazolam, diazepam, flurazepam, lorazepam, medazepam, mexazolam, midazolam, temazepam and pharmaceutically acceptable salts and combinations thereof. In some embodiments, the benzodiazepine drug comprises one or more members of the group consisting of diazepam, lorazepam, midazolam and pharmaceutically acceptable salts thereof. In some embodiments, the benzodiazepine particles contain crystalline benzodiazepine, amorphous benzodiazepine, semi-crystalline benzodiazepine, a mixture of amorphous and crystalline benzodiazepine, a mixture of amorphous and semi-crystalline benzodiazepine, a mixture of crystalline and semi-crystalline benzodiazepine and a mixture of amorphous, crystalline and semi-crystalline benzodiazepine. In some embodiments, the benzodiazepine particles contain crystalline diazepam, amorphous diazepam, semi-crystalline diazepam, a mixture of amorphous and crystalline diazepam, a mixture of amorphous and semi-crystalline diazepam, a mixture of crystalline and semi-crystalline diazepam, a mixture of amorphous, crystalline and semi-crystalline diazepam, crystalline lorazepam, amorphous lorazepam, semi-crystalline lorazepam, a mixture of amorphous and crystalline lorazepam, a mixture of amorphous and semi-crystalline lorazepam, a mixture of crystalline and semi-crystalline lorazepam, a mixture of amorphous, crystalline and semi-crystalline lorazepam, crystalline medazepam, amorphous medazepam, semi-crystalline medazepam, a mixture of amorphous and crystalline medazepam, a mixture of amorphous and semi-crystalline medazepam, a mixture of crystalline and semi-crystalline medazepam and a mixture of amorphous, crystalline and semi-crystalline medazepam. In some embodiments, the benzodiazepine particles have a mean particle size of less than about 5000 nm. In some embodiments, the benzodiazepine particles have a mean particle size of less than about 4000 nm. In some embodiments, the benzodiazepine particles have a mean particle size in the range of about 50 to 5000 nm, about 100 to about 2500 nm, about 250 to about 1000 nm or approximately 500 nm. In some embodiments, the benzodiazepine particles do not contain solvent residues resulting from solvent extraction or solvent precipitation. In some embodiments, the benzodiazepine particles further comprise at least one additional ingredient selected from active pharmaceutical ingredients and enhancers. In some embodiments, the effective amount of the composition is effective to treat seizure, protect against seizure, reduce or ameliorate the intensity of seizure, reduce or ameliorate the frequency of seizure, and/or prevent occurrence or re-occurrence of seizure. In some embodiments, the effective amount of the composition is effective to provide a therapeutic effect selected from an anxiolytic effect, an anticonvulsant effect, a sedative effect, a skeletal muscle relaxant effect, an amnesic effect or combinations thereof. In some embodiments, a therapeutically effective plasma level of benzodiazepine drug is obtained within about 1 hour of administration of the composition to a patient. In some embodiments, the therapeutically effective plasma level of the benzodiazepine drug is obtained within about 30 minutes of administration of the composition to the patient. In some embodiments, the therapeutically effective plasma level of the benzodiazepine is obtained within about 15 minutes of administration of the composition to the patient. In some embodiments, the therapeutically effective plasma level of benzodiazepine drug is obtained within about 10 minutes of administration of the composition to the patient. In some embodiments, the therapeutically effective plasma level of benzodiazepine drug is obtained within about 5 minutes of administration of the composition to the patient. In some embodiments, peak plasma concentration ($C_{max}$) is achieved for the benzodiazepine drug at a time ($T_{max}$) less than about 1 hour after administration of the composition to a patient. In some embodiments, $T_{max}$ is less than about 30 minutes after administration of the composition to the patient. In some embodiments, $T_{max}$ is less than about 15 minutes after administration of the composition to the patient. In some embodiments, $T_{max}$ is less than about 12 minutes after administration of the composition to the patient.

In some embodiments, the invention provides an aqueous dispersion or suspension of nanoparticulate benzodiazepine particles. In some embodiments, the nanoparticulate benzodiazepine particles comprise at least one member of the group consisting of alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, medazepam, lorazepam, prazepam, quazepam, triazolam, temazepam, loprazolam, and pharmaceutically acceptable salts and combinations thereof. In some embodiments, the nanoparticulate benzodiazepine particles comprise at least one member of the group consisting of alprazolam, diazepam, flurazepam, lorazepam, medazepam, mexazolam, midazolam, temazepam and pharmaceutically acceptable salts and combinations thereof. In some embodiments, the nanoparticulate benzodiazepine particles comprise at least one benzodiazepine selected from the group consisting of diazepam, lorazepam, midazolam and pharmaceutically acceptable salts thereof. In some embodiments, the droplets have a mass median aerodynamic diameter (MMAD) less than or equal to about 1000 μm and the nanoparticulate benzodiazepine particles have an effective average particle size of less than about 5000 nm. In some embodiments, the nanoparticulate benzodiazepine particles have an effective average particle size of less than about 1000 nm, less than about 500 nm, less than about 400 nm, less than about 250 nm, less than about 100 nm or less than about 50 nm. In some embodiments, the nanoparticulate benzodiazepine particles have an effective average particle size in the range of about 25 to about 10000 nm. In some embodiments, the nanoparticulate benzodiazepine particles have an effective average particle size of about 50 to about 5000 nm. In some embodiments, the aqueous dispersion or suspension is adapted for nasal administration. In some embodiments, the dispersion or suspension further comprises at least one additional ingredient selected from the group consisting of active pharmaceutical ingredients and enhancers. In some embodiments, the composition further comprises a non-aqueous carrier or propellant. In some embodiments, the non-aqueous carrier or propellant comprises a hydrocarbon, a hydrofluorocarbon or a chlorofluorocarbon. In some embodiments, at least a portion of the particles is coated with at least one surface acting agent. In some embodiments, at least one surface acting agent is a cationic surfactant, a non-ionic surfactant, an anionic surfactant, a surface active biological modifier or a zwitterionic surfactant. In some embodiments, at least one surface acting agent is a cationic surfactant selected from the group consisting of natural phospholipids, synthetic phospholipids, quaternaryammonium compounds, benzalkonium chloride, cetyltrimethylammonium bromide, chitosans, lauryldimethylbenzylammonium chloride, acyl carnitine hydrochlorides, dimethyldioctadecylammomium bromide (DDAB), dioleyoltrimethylammonium propane (DOTAP), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, and long-chain alkyl amines such as, for example, n-octylamine and oleylamine. In some embodiments, at least one surface acting agent is an anionic surface active agent selected from the group consisting of natural anionic phospholipids, synthetic anionic phospholipids and anionic polymers. In some embodiments, the natural anionic phospholipids, synthetic anionic phospholipids and anionic polymers are selected from the group consisting of polyacrylic acid, carrageenan k type II, carbopol 980, carbopol 974 P, carbopol 971 P, polycarbophil, sodium carboxymethylcellulose, sodium hyaluronate or combinations thereof. In some embodiments, at least one surface acting agent is selected from the group consisting of thiolated polymers. In some embodiments, the thiolated polymer is selected from the group consisting of cysteine conjugates of polyacrylic acid, polycarbophil (thiomer polycarbophil-cysteine), thiolated sodium carboxymethylcellulose, chitosan modified with 2-iminothiolate (e.g. chitosan-4-thiobutylamidine conjugates, chitosan-thioglycolic acid conjugates, chitosan-cysteine conjugates). In some embodiments, at least one surface acting agent is selected from the group consisting of polymeric mucilaginous polysaccharides. In some embodiments, the polymeric mucilaginous polysaccharide is from the aloe vera plant. In some embodiments, at least one surface acting agent is methylcellulose, ethylcellulose, hydroxypropylmethylcellulose (HPMC) or a mixture of two or more thereof. In some embodiments, the nanoparticulate benzodiazepine has a multimodal particle size distribution. In some embodiments, the nanoparticulate benzodiazepine has a bimodal particle size distribution. In some embodiments, the nanoparticulate benzodiazepine has a trimodal or higher order modal particle size distribution.

In some embodiments, the invention provides a method of using an aqueous dispersion or suspension of nanoparticulate benzodiazepine, comprising administering an effective amount of the dispersion or suspension to the nose by administering a therapeutically effective amount of the composition to at least one nostril. In some embodiments, the method comprises administering at least a portion of the therapeutically effective amount of the composition to each nostril. In some embodiments, the method comprises administering a first quantity of the composition to a first nostril, administering a second quantity of the composition to a second nostril, and optionally after a pre-selected time delay, administering a third quantity of the composition to the first nostril. In some embodiments, the method further comprises, optionally after a pre-selected time delay, administering at least a fourth quantity of the composition to the second nostril. In some embodiments, the effective amount of the composition is effective to treat seizure, protect against seizure, reduce or ameliorate the intensity of seizure, reduce or ameliorate the frequency of seizure, and/or prevent occurrence or re-occurrence of seizure. In some embodiments, the effective amount of the composition is effective to provide a therapeutic effect selected from an anxiolytic effect, an anticonvulsant effect, a sedative effect, a skeletal muscle relaxant effect, an amnesic effect or combinations thereof. In some embodiments, a therapeutically effective plasma level of benzodiazepine drug is obtained within about 1 hour of administration of the composition to a patient. In some embodiments, the therapeutically effective plasma level of the benzodiazepine drug is obtained within about 30 minutes of administration of the composition to the patient. In some embodiments, the therapeutically effective plasma level of the benzodiazepine is obtained within about 15 minutes of administration of the composition to the patient. In some embodiments, the therapeutically effective plasma level of benzodiazepine drug is obtained within about 10 minutes of administration of the composition to the patient. In some embodiments, the therapeutically effective plasma level of benzodiazepine drug is obtained within about 5 minutes of administration of the composition to the patient. In some embodiments, peak plasma concentration ($C_{max}$) is achieved for the benzodiazepine drug at a time ($T_{max}$) less than about 1 hour after administration of the composition to a patient. In some embodiments, $T_{max}$ is less than about 30 minutes after administration of the composition to the patient. In some embodiments, $T_{max}$ is less than about 15 minutes after administration of the composition to the patient. In some embodiments, $T_{max}$ is less than about 12 minutes after administration of the composition to the patient.

In some embodiments, the invention provides a method of administering a benzodiazepine drug to a patient, comprising administering to the patient's nose, nasal cavity or lungs a pharmaceutical composition comprising an aqueous dispersion or suspension of nanoparticulate benzodiazepine particles. In some embodiments, the nanoparticulate benzodiazepine particles comprise at least one member of the group consisting of alprazolam, brotizolam, chlordiazep oxide, clobazam, clonazepam, clorazepam, demoxazepam, flumazenil, flurazepam, halazepam, midazolam, nordazepam, medazepam, diazepam, nitrazepam, oxazepam, medazepam, lorazepam, prazepam, quazepam, triazolam, temazepam, loprazolam, and pharmaceutically acceptable salts and combinations thereof. In some embodiments, the benzodiazepine drug comprises at least one member of the group consisting of alprazolam, diazepam, flurazepam, lorazepam, medazepam, mexazolam, midazolam, temazepam and pharmaceutically acceptable salts and combinations thereof. In some embodiments, the benzodiazepine drug comprises one or more members of the group consisting of diazepam, lorazepam, midazolam and pharmaceutically acceptable salts thereof. In some embodiments, the benzodiazepine particles contain crystalline benzodiazepine, amorphous benzodiazepine, semi-crystalline benzodiazepine, a mixture of amorphous and crystalline benzodiazepine, a mixture of amorphous and semi-crystalline benzodiazepine, a mixture of crystalline and semi-crystalline benzodiazepine and a mixture of amorphous, crystalline and semi-crystalline benzodiazepine. In some embodiments, the benzodiazepine particles contain crystalline diazepam, amorphous diazepam, semi-crystalline diazepam, a mixture of amorphous and crystalline diazepam, a mixture of amorphous and semi-crystalline diazepam, a mixture of crystalline and semi-crystalline diazepam, a mixture of amorphous, crystalline and semi-crystalline diazepam, crystalline lorazepam, amorphous lorazepam, semi-crystalline lorazepam, a mixture of amorphous and crystalline lorazepam, a mixture of amorphous and semi-crystalline lorazepam, a mixture of crystalline and semi-crystalline lorazepam, a mixture of amorphous, crystalline and semi-crystalline lorazepam, crystalline medazepam, amorphous medazepam, semi-crystalline medazepam, a mixture of amorphous and crystalline medazepam, a mixture of amorphous and semi-crystalline medazepam, a mixture of crystalline and semi-crystalline medazepam and a mixture of amorphous, crystalline and semi-crystalline medazepam. In some embodiments, the benzodiazepine particles have a mean particle size of less than about 5000 nm. In some embodiments, the benzodiazepine particles have a mean particle size of less than about 4000 nm. In some embodiments, the benzodiazepine particles have a mean particle size in the range of about 50 to 5000 nm, about 100 to about 2500 nm, about 250 to about 1000 nm or approximately 500 nm. In some embodiments, the benzodiazepine particles do not contain solvent residues resulting from solvent extraction or solvent precipitation. In some embodiments, the benzodiazepine particles further comprise at least one additional ingredient selected from active pharmaceutical ingredients and enhancers. In some embodiments, the effective amount of the composition is effective to treat seizure, protect against seizure, reduce or ameliorate the intensity of seizure, reduce or ameliorate the frequency of seizure, and/or prevent occurrence or re-occurrence of seizure. In some embodiments, the effective amount of the composition is effective to provide a therapeutic effect selected from an anxiolytic effect, an anticonvulsant effect, a sedative effect, a skeletal muscle relaxant effect, an amnesic effect or combinations thereof. In some embodiments, a therapeutically effective plasma level of benzodiazepine drug is obtained within about 1 hour of administration of the composition to a patient. In some embodiments, the therapeutically effective plasma level of the benzodiazepine drug is obtained within about 30 minutes of administration of the composition to the patient. In some embodiments, the therapeutically effective plasma level of the benzodiazepine is obtained within about 15 minutes of administration of the composition to the patient. In some embodiments, the therapeutically effective plasma level of benzodiazepine drug is obtained within about 10 minutes of administration of the composition to the patient. In some embodiments, the therapeutically effective plasma level of benzodiazepine drug is obtained within about 5 minutes of administration of the composition to the patient. In some embodiments, peak plasma concentration ($C_{max}$) is achieved for the benzodiazepine drug at a time ($T_{max}$) less than about 1 hour after administration of the composition to a patient. In some embodiments, $T_{max}$ is less than about 30 minutes after administration of the composition to the patient. In some embodiments, $T_{max}$ is less than about 15 minutes after administration of the composition to the patient. In some embodiments, $T_{max}$ is less than about 12 minutes after administration of the composition to the patient.

In some embodiments, the invention provides a nanoparticulate composition comprising: (a) a benzodiazepine having an effective average particle size of less than about 2000 nm, wherein the benzodiazepine is selected from the group consisting of alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, midazepam, lorazepam, prazepam, quazepam, triazolam, temazepam, loprazolam, pharmaceutically acceptable salts and esters thereof, and mixtures thereof; and (b) at least one surface stabilizer. In some embodiments, the surface stabilizer is selected from the group consisting of a nonionic surfactant, an ionic surfactant, a cationic surfactant, an anionic surfactant, and a zwitterionic surfactant. In some embodiments, the surface stabilizer is selected from the group consisting of hypromellose, hydroxypropylcellulose, polyvinylpyrrolidone, sodium lauryl sulfate, dioctylsulfosuccinate, gelatin, casein, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, carboxymethylcellulose calcium, carboxymethylcellulose sodium, methylcellulose, hydroxyethylcellulose, hypromellose phthalate, noncrystalline cellulose, magnesium aluminum silicate, triethanolamine, polyvinyl alcohol, tyloxapol, poloxamers, poloxamines, Tetronic 1508®, an alkyl aryl polyether sulfonate, a mixture of sucrose stearate and sucrose distearate, p-isononylphenoxypoly-(glycidol), Crodestas SL-40® (Croda, Inc.); and SA9OHCO, decanoyl-N-methylglucamide; n-decyl (-D-glucopyranoside); n-decyl (-D-maltopyranoside); n-dodecyl (-D-glucopyranoside); n-dodecyl (-D-maltoside; heptanoyl-N-methylglucamide); n-heptyl-(-D-glucopyranoside); n-heptyl (-D-thioglucoside); n-hexyl (-D-glucopyranoside); nonanoyl-N-methylglucamide; n-noyl (-D-glucopyranoside); octanoyl-N-methylglucamide; n-octyl-(-D-glucopyranoside); octyl (-D-thioglucopyranoside); PEG-phospholipid, PEG-cholesterol, PEG-cholesterol derivative, PEG-vitamin A, PEG-vitamin E, lysozyme, random copolymers of vinyl pyrrolidone and vinyl acetate, cationic polymers, cationic biopolymers, cationic polysaccharides, cationic cellulosics, cationic alginates, cationic phospho lipids, cationic nonpolymeric compounds, poly-n-methylpyridinium, anthryul pyridinium chloride, cationic phospholipids, chitosan, polylysine, polyvinylimidazole, polybrene, polymethylmethacrylate trimethylammoniumbromide bromide, hexyldesyltrimethylammonium bromide, polyvinylpyrrolidone-2-dimethylamino ethyl methacrylate dimethyl sulfate, cationic lipids, sulfonium, phosphonium, quarternary ammonium compounds, stearyltrimethylammonium chloride, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium bromide, $C_{12-15}$-dimethyl hydroxyethyl ammonium chloride, $C_{12-15}$dimethyl hydroxyethyl ammonium bromide, coconut dimethyl hydroxyethyl ammonium chloride, coconut dimethyl hydroxyethyl ammonium bromide, myristyl trimethyl ammonium methyl sulfate, lauryl dimethyl benzyl ammonium chloride, lauryl dimethyl benzyl ammonium bromide, lauryl dimethyl $(ethenoxy)_4$ ammonium chloride, lauryl dimethyl $(ethenoxy)_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride, dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, POLYQUAT, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, MIRAPOL, ALKAQUAT, alkyl pyridinium salts, amines, alkylamines, dialkylamines, alkanolamines, polyethylenepolyamines, N,N-dialkylaminoalkyl acrylates, vinyl pyridine, amine salts, lauryl amine acetate, stearyl amine acetate, alkylpyridinium salt, alkylimidazolium salt, amine oxides, imide azolinium salts, protonated quaternary acrylamides, methylated quaternary polymers, and cationic guar. In some embodiments, the nanoparticulate benzodiazepine particles have an effective average particle size selected from the group consisting of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, less than about 75 nm, and less than about 50 mm. In some embodiments, the composition is formulated into an aerosol of an aqueous dispersion of the composition described above, wherein essentially each droplet of the aerosol comprises at least one nanoparticulate benzodiazepine particle, wherein: (a) the benzodiazepine has a solubility in the aqueous dispersion of less than about 10 mg/mL; and (b) the droplets of the aerosol have a mass median aerodynamic diameter (MMAD) less than or equal to about 100 microns. In some embodiments, the benzodiazepine is present in a concentration selected from the group consisting of from about 0.05 mg/mL up to about 600 mg/mL, about 10 mg/mL or more, about 100 mg/mL or more, about 200 mg/mL or more, about 400 mg/mL or more, and about 600 mg/mL. In some embodiments, the composition is suitable for administration of the benzodiazepine dosage in about 15 seconds or less. In some embodiments, the droplets of the aerosol have a mass median aerodynamic diameter (MMAD) selected from the group consisting of about 2 to about 10 microns, about 2 to about 6 microns, less than about 2 microns, about 5 to about 100 microns, and about 30 to about 60 microns. In some embodiments, the composition is formulated into an injectable composition. In some embodiments, the composition comprises povidones as a surface stabilizer. In some embodiments, the povidone polymer has a molecular weight of about 40,000 daltons or less. In some embodiments, the effective average particle size of the benzodiazepine particles is less than about 600 nm.

In some embodiments, the invention provides a method of treating a subject in need comprising administering to the subject a nanoparticulate benzodiazepine composition comprising: (a) a benzodiazepine having an effective average particle size of less than about 2000 nm, wherein the benzodiazepine is selected from the group consisting of alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, midazepam, lorazepam, prazepam, quazepam, triazolam, temazepam, loprazolam, pharmaceutically acceptable salts and esters thereof, and mixtures thereof; and (b) at least one surface stabilizer. In some embodiments, the surface stabilizer is selected from the group consisting of a nonionic surfactant, an ionic surfactant, a cationic surfactant, an anionic surfactant, and a zwitterionic surfactant. In some embodiments, the surface stabilizer is selected from the group consisting of hypromellose, hydroxypropylcellulose, polyvinylpyrrolidone, sodium lauryl sulfate, dioctylsulfosuccinate, gelatin, casein, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, carboxymethylcellulose calcium, carboxymethylcellulose sodium, methylcellulose, hydroxyethylcellulose, hypromellose phthalate, noncrystalline cellulose, magnesium aluminum silicate, triethanolamine, polyvinyl alcohol, tyloxapol, poloxamers, poloxamines, Tetronic 1508®, an alkyl aryl polyether sulfonate, a mixture of sucrose stearate and sucrose distearate, p-isononylphenoxypoly-(glycidol), Crodestas SL-40® (Croda, Inc.); and SA9OHCO, decanoyl-N-methylglucamide; n-decyl (–D-glucopyranoside; n-decyl (–D-maltopyranoside; n-dodecyl (–D-glucopyranoside; n-dodecyl (–D-maltoside; heptanoyl-N-methylglucamide; n-heptyl-(–D-glucopyranoside; n-heptyl (–D-thioglucoside; n-hexyl (–D-glucopyranoside; nonanoyl-N-methylglucamide; n-noyl (–D-glucopyranoside; octanoyl-N-methylglucamide; n-octyl-(–D-glucopyranoside; octyl (–D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, cationic polymers, cationic biopolymers, cationic polysaccharides, cationic cellulosics, cationic alginates, cationic phospholipids, cationic nonpolymeric compounds, poly-n-methylpyridinium, anthryul pyridinium chloride, cationic phospholipids, chitosan, polylysine, polyvinylimidazole, polybrene, polymethylmethacrylate trimethylammoniumbromide bromide, hexyldesyltrimethylammonium bromide, polyvinylpyrrolidone-2-dimethylaminoethyl methacrylate dimethyl sulfate, cationic lipids, sulfonium, phosphonium, quarternary ammonium compounds, stearyltrimethylammonium chloride, benzyl-di(2-chloroethyl) ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium bromide, $C_{12-15}$dimethyl hydroxyethyl ammonium chloride, $C_{12-15}$dimethyl hydroxyethyl ammonium bromide, coconut dimethyl hydroxyethyl ammonium chloride, coconut dimethyl hydroxyethyl ammonium bromide, myristyl trimethyl ammonium methyl sulfate, lauryl dimethyl benzyl ammonium chloride, lauryl dimethyl benzyl ammonium bromide, lauryl dimethyl $(ethenoxy)_4$ ammonium chloride, lauryl dimethyl $(ethenoxy)_4$ ammonium bromide, N-alkyl ($C_{12-18}$)dimethylbenzyl ammonium chloride, N-alkyl ($C_{14-18}$)dimethylbenzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride, dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, POLYQUAT, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, MIRAPOL, ALKAQUAT, alkyl pyridinium salts, amines, alkylamines, dialkylamines, alkanolamines, polyethylenepolyamines, N,N-dialkylaminoalkyl acrylates, vinyl pyridine, amine salts, lauryl amine acetate, stearyl amine acetate, alkylpyridinium salt, alkylimidazolium salt, amine oxides, imide azolinium salts, protonated quaternary acrylamides, methylated quaternary polymers, and cationic guar. In some embodiments, the nanoparticulate benzodiazepine particles have an effective average particle size selected from the group consisting of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, less than about 75 nm, and less than about 50 nm. In some embodiments, the composition is formulated into an aerosol of an aqueous dispersion of the composition described above, wherein essentially each droplet of the aerosol comprises at least one nanoparticulate benzodiazepine particle, wherein: (a) the benzodiazepine has a solubility in the aqueous dispersion of less than about 10 mg/mL; and (b) the droplets of the aerosol have a mass median aerodynamic diameter (MMAD) less than or equal to about 100 microns. In some embodiments, the benzodiazepine is present in a concentration selected from the group consisting of from about 0.05 mg/mL up to about 600 mg/mL, about 10 mg/mL or more, about 100 mg/mL or more, about 200 mg/mL or more, about 400 mg/mL or more, and about 600 mg/mL. In some embodiments, the composition is suitable for administration of the benzodiazepine dosage in about 15 seconds or less. In some embodiments, the droplets of the aerosol have a mass median aerodynamic diameter (MMAD) selected from the group consisting of about 2 to about 10 microns, about 2 to about 6 microns, less than about 2 microns, about 5 to about 100 microns, and about 30 to about 60 microns. In some embodiments, the composition is formulated into an injectable dosage form. In some embodiments, the composition comprises povidone as a surface stabilizer. In some embodiments, the povidone polymer has a molecular weight of about 40,000 daltons or less. In some embodiments, the effective average particle size of the benzodiazepine particles is less than about 600 nm.

As used herein the phrase "therapeutically effective amount" (or more simply "effective amount") means an amount sufficient to provide a specific therapeutic response for which the drug is administered to a patient in need of particular treatment. The skilled clinician will recognize that the therapeutically effective amount of drug will depend upon the patient, the indication and the particular drug administered.

As used herein the terms "Cmax," and "Tmax" have the ordinary meaning in the art with respect to pharmacokinetic (PK) curves. Where more than one Cmax occurs, meaning that there is a local maximum in the PK curve, each Cmax may be sequentially numbered in order of appearance, so that the first local maximum in the PK curve is numbered Cmax1, the second Cmax2, etc. The times at which Cmax1, Cmax2, etc. appear are correspondingly sequentially designated Tmax1, Tmax2, etc.

As used herein, the modifier "about" is intended to have its regularly recognized meaning of approximately. In some embodiments, the term may be more precisely interpreted as meaning within a particular percentage of the modified value, e.g. "about" may in some embodiments mean±20%, ±10% or ±5%.

Benzodiazepine Drugs

In the context of the present invention, the term "benzodiazepine drug" includes any therapeutically effective benzodiazepine compound, or pharmaceutically acceptable salt or combinations thereof. In some embodiments, the nanoparticulate benzodiazepine particles comprise at least one member of the group consisting of alprazolam, diazepam, flurazepam, lorazepam, medazepam, mexazolam, midazolam, temazepam and pharmaceutically acceptable salts and combinations thereof. In some embodiments, the nanoparticulate benzodiazepine particles comprise at least one benzodiazepine selected from the group consisting of diazepam, lorazepam, midazolam and pharmaceutically acceptable salts thereof. However, it should be recognized by those of skill in the art that additional benzodiazepine compounds that have heretofore been considered to have marginal or little therapeutic benefit, either because of low bioavailability, poor pharmacokinetic properties or poor pharmacodynamic properties, may find use in the present invention, which provides for improved bioavailability of benzodiazepine drugs, delivery of higher concentrations of benzodiazepine drugs via the nasal route, faster attainment of therapeutic levels of benzodiazepine in the blood plasma, avoidance of the liver portal vein and concomitant avoidance of first pass effects and/or faster presentation of benzodiazepine drug to the brain. In some embodiments, the invention provides as a preferred embodiment, diazepam or a therapeutically acceptable salt thereof.

Alprazolam (8-chloro-6-phenyl-1-methyl-4H-1,2,4-triazolo[4,3-a][1,4]benzodiazepine)

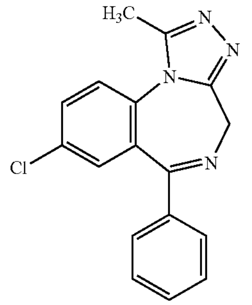 [SMILES: Cc1nnc2n1-c1ccc(Cl)cc1C(c1ccccc1)=NC2]

Alprazolam is a benzodiazepine drug having sedative, tranquilizing and muscle relaxing properties. It is classified as an anxiolytic. Alprazolam has also been shown to be useful in the treatment of panic disorder. The dosage of Alprazolam varies by indication, however it is expected that a therapeutic dose will be in the range of about 0.5 to about 4, preferably about 1 to about 2 mg per dose, from 1 to 8, preferably from 2 to 8, and in some preferred embodiments about 4 to about 6 times per day. Alprazolam may be manufactured using the process disclosed in U.S. Pat. No. 3,987,052, which is incorporated herein by reference in its entirety.

As a nasal formulation, alprazolam may be administered in 25 to 250 μl metered sprays. In some preferred embodiments, alprazolam is administered in 50 to 150 μL, especially about 100 μL, metered sprays. In some embodiments, a first metered spray is applied to a first nostril and if necessary a second metered spray is applied to a second nostril. In some optional embodiments, a third metered spray is applied to the first nostril. In some further embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Alprazolam may be combined with other pharmaceutically active ingredients, including other benzodiazepine compounds (such as diazepam) in a benzodiazepine drug formulation. In some embodiments, the ratio of alprazolam to the other pharmaceutically active ingredient is in one of the ranges from about 1:1000 to about 1000:1, about 1:100 to about 100:1 or about 1:10 to about 10:1. In some embodiments, the other pharmaceutically active ingredient is a benzodiazepine drug and the ratio of alprazolam to the other benzodiazepine drug is in one of the ranges from about 1:1000 to about 1000:1, about 1:100 to about 100:1 or about 1:10 to about 10:1. In some embodiments, the other pharmaceutically active ingredient is diazepam and the ratio of alprazolam to diazepam is about 1:1000 to about 1000:1, about 1:100 to about 100:1 or about 1:10 to about 10:1.

In some embodiments, Alprazolam is used alone or in combination with other drugs to provide an anxiolytic effect, an anticonvulsant effect, a sedative effect, a skeletal muscle relaxant effect, an amnesic effect or combinations of the foregoing effects.

In some embodiments, Alprazolam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Alprazolam may be administered by the patient or other person (such as a healthcare professional) while the patient is in a non-seizing state to protect against seizure. Even where protection against seizure is not absolute, administration of alprazolam may reduce or ameliorate the intensity of seizure and/or reduce or ameliorate the frequency of seizure. In some embodiments, administration of alprazolam may prevent occurrence of seizure. In some embodiments, especially where the patient is prone to experiencing serial seizures or status epilepticus, administration of alprazolam may aid in interrupting the seizure cycle and may thus prevent the re-occurrence of seizure. In addition to the benzodiazepines (such as diazepam), other anti-convulsant drugs may be combined with alprazolam to provide a synergistic anticonvulsant effect.

Alprazolam may also be administered by another person (e.g. an acquaintance or associate, a family member or a health care professional) to the patient while the patient is in a state of seizure. Thus, one of the advantages of the nasal formulations according to the present invention is the ability to administer them in an acute therapeutic environment to treat the seizure victim. Among the beneficial therapeutic effects that may be imparted by acute nasal dosing of benzodiazepine anticonvulsants are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus the nasal alprazolam formulations of the invention provide fast onset of therapeutic benefit—in some instances less than about 30 minutes, less than about 15 minutes, less than about 10 minutes, and in some cases less than about 5 minutes. The nasal alprazolam formulations of the invention also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or at least often, precedes a patient's experiencing a seizure. In some embodiments of the invention, the method includes prompt administration of a nasal preparation of a benzodiazepine drug according to the invention during the aura. In some embodiments, such intra-aural administration of benzodiazepine drug by the intra-nasal route will prevent or at least ameliorate the effects (intensity, duration or both) of the impending seizure. Thus, in the context of this invention, prevention of seizure refers to a temporary forestalling of the onset of seizure, either with or without the benefit of a warning aura.

Diazepam (7-chloro-1-methyl-5-phenyl-1,3-dihydro-2H-1,4-benzodiazepin-2-one)

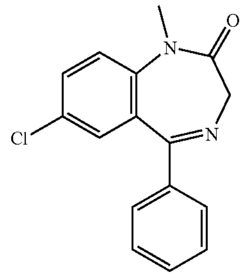 [SMILES: CN1C(=O)CN=C(c2ccccc2)c2cc(Cl)ccc21]

Diazepam is a benzodiazepine drug having sedative, tranquilizing and muscle relaxing properties. It is classified as an anxiolytic and skeletal muscle relaxant. It possesses anxiolytic, anticonvulsant, sedative, skeletal muscle relaxant and amnesic properties. The dosage of Diazepam may vary by indication, however it is expected that a therapeutic dose will be in the range of about 1 to about 20, preferably about 2 to about 10 mg per dose, from 1 to 8, preferably from 2 to 8, and in some preferred embodiments about 4 to about 6 times per day. Diazepam may be manufactured using the process disclosed in one of U.S. Pat. Nos. 3,371,085, 3,109,843, 3,136,815 or 3,102,116, each of which is incorporated herein by reference in its entirety.

As a nasal formulation, diazepam may be administered in 25 to 250 μl metered sprays. In some preferred embodiments, diazepam is administered in 50 to 150 μl, especially about 100 μl, metered sprays. In some embodiments, a first metered spray is applied to a first nostril and if necessary a second metered spray is applied to a second nostril. In some optional embodiments, a third metered spray is applied to the first nostril. In some further embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Diazepam may be combined with other pharmaceutically active ingredients, including other benzodiazepine compounds in a benzodiazepine drug formulation. In some embodiments, the ratio of diazepam to the other pharmaceutically active ingredient is in one of the range from about 1:1000 to about 1000:1, about 1:100 to about 100:1 or about 1:10 to about 10:1. In some embodiments, the other pharmaceutically active ingredient is a benzodiazepine drug and the ratio of diazepam to the other benzodiazepine drug is in one of the range from about 1:1000 to about 1000:1, about 1:100 to about 100:1 or about 1:10 to about 10:1. In some embodiments, the other pharmaceutically active ingredient is lorazepam. In some embodiments, the ratio of diazepam to lorazepam is in the range of about 1:1000 to about 1000:1, especially about 1:10 to about 10:1. In some embodiments, the other pharmaceutically active ingredient is medazepam. In some embodiments, the ratio of diazepam to medazepam is in the range of about 1:1000 to about 1000:1, especially about 1:10 to about 10:1.

In some embodiments, Diazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, Diazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Diazepam may be administered by the patient or other person (such as a healthcare professional) while the patient is in a non-seizing state to protect against seizure. Even where protection against seizure is not absolute, administration of diazepam may reduce or ameliorate the intensity of seizure and/or reduce or ameliorate the frequency of seizure. In some embodiments, administration of diazepam may prevent occurrence of seizure. In some embodiments, especially where the patient is prone to experiencing serial seizures or status epilepticus, administration of diazepam may aid in interrupting the seizure cycle and may thus prevent the re-occurrence of seizure. In addition to the benzodiazepines (such as diazepam), other anti-convulsant drugs may be combined with diazepam to provide a synergistic anticonvulsant effect.

Diazepam may also be administered by another person (e.g. an acquaintance or associate, a family member or a health care professional) to the patient while the patient is in a state of seizure. Thus, one of the advantages of the nasal formulations according to the present invention is the ability to administer them in an acute therapeutic environment to treat the seizure victim. Among the beneficial therapeutic effects that may be imparted by acute nasal dosing of benzodiazepine anticonvulsants are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus the nasal diazepam formulations of the invention provide fast onset of therapeutic benefit—in some instances less than about 30 minutes, less than about 15 minutes, less than about 10 minutes, and in some cases less than about 5 minutes. The nasal diazepam formulations of the invention also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or at least often, precedes a patient's experiencing a seizure. In some embodiments of the invention, the method includes prompt administration of a nasal preparation of a benzodiazepine drug according to the invention during the aura. In some embodiments, such intra-aural administration of diazepam drug by the intra-nasal route will prevent or at least ameliorate the effects (intensity, duration or both) of the impending seizure. Thus, in the context of this invention, prevention of seizure refers to a temporary forestalling of the onset of seizure, either with or without the benefit of a warning aura.

Flurazepam (7-chloro-5-(2-fluorophenyl)-2,3-dihydro-1-(2-(diethylamino)ethyl)-1H-1,4-benzodiazepin-2-one)

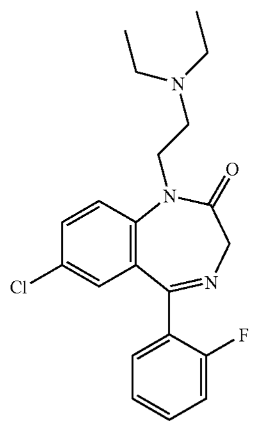 [SMILES: CCN(CC)CCN1C(=O)CN=C(c2ccccc2F)c2cc(Cl)ccc21]

Flurazepam is a benzodiazepine drug having sedative (especially soporific and hypnotic), anxiolytic, anticonvulsant and muscle relaxing properties. It is classified as an sedative, hypnotic. Flurazepam has been shown to be useful in the treatment of insomnia. The dosage of Flurazepam varies by indication, however it is expected that a therapeutic dose will be in the range of about 5 to 40, preferably about 20 to about 35 mg per dose, from 1 to 8, preferably from 2 to 8, and in some preferred embodiments about 4 to about 6 times per day. Flurazepam may be manufactured using the process disclosed in U.S. Pat. No. 3,567,710 or 3,299,053, each of which is incorporated herein by reference in its entirety.

As a nasal formulation, flurazepam may be administered in 25 to 250 μl metered sprays. In some preferred embodiments, flurazepam is administered in 50 to 150 μl, especially about 100 μl, metered sprays. In some embodiments, a first metered spray is applied to a first nostril and if necessary a second metered spray is applied to a second nostril. In some optional embodiments, a third metered spray is applied to the first nostril. In some further embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Flurazepam may be combined with other pharmaceutically active ingredients, including other benzodiazepine compounds (such as diazepam) in a benzodiazepine drug formulation. In some embodiments, the ratio of flurazepam to the other pharmaceutically active ingredient is in one of the ranges from about 1:1000 to about 1000:1, about 1:100 to about 100:1 or about 1:10 to about 10:1. In some embodiments, the other pharmaceutically active ingredient is a benzodiazepine drug and the ratio of flurazepam to the other benzodiazepine drug is in one of the ranges from about 1:1000 to about 1000:1, about 1:100 to about 100:1 or about 1:10 to about 10:1. In some embodiments, the other pharmaceutically active ingredient is diazepam and the ratio of flurazepam to diazepam is about 1:1000 to about 1000:1, about 1:100 to about 100:1 or about 1:10 to about 10:1.

In some embodiments, Flurazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, Flurazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Flurazepam may be administered by the patient or other person (such as a healthcare professional) while the patient is in a non-seizing state to protect against seizure. Even where protection against seizure is not absolute, administration of flurazepam may reduce or ameliorate the intensity of seizure and/or reduce or ameliorate the frequency of seizure. In some embodiments, administration of flurazepam may prevent occurrence of seizure. In some embodiments, especially where the patient is prone to experiencing serial seizures or status epilepticus, administration of flurazepam may aid in interrupting the seizure cycle and may thus prevent the re-occurrence of seizure. In addition to the benzodiazepines (such as diazepam), other anti-convulsant drugs may be combined with flurazepam to provide a synergistic anticonvulsant effect.

Flurazepam may also be administered by another person (e.g. an acquaintance or associate, a family member or a health care professional) to the patient while the patient is in a state of seizure. Thus, one of the advantages of the nasal formulations according to the present invention is the ability to administer them in an acute therapeutic environment to treat the seizure victim. Among the beneficial therapeutic effects that may be imparted by acute nasal dosing of benzodiazepine anticonvulsants are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus the nasal flurazepam formulations of the invention provide fast onset of therapeutic benefit—in some instances less than about 30 minutes, less than about 15 minutes, less than about 10 minutes, and in some cases less than about 5 minutes. The nasal flurazepam formulations of the invention also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or at least often, precedes a patient's experiencing a seizure. In some embodiments of the invention, the method includes prompt administration of a nasal preparation of a benzodiazepine drug according to the invention during the aura. In some embodiments, such intra-aural administration of benzodiazepine drug by the intra-nasal route will prevent or at least ameliorate the effects (intensity, duration or both) of the impending seizure. Thus, in the context of this invention, prevention of seizure refers to a temporary forestalling of the onset of seizure, either with or without the benefit of a warning aura.

Lorazepam (7-chloro-5-(2-chlorophenyl)-3-hydroxy-1,3-dihydro-2H-1,4-benzodiazepin-2-one)

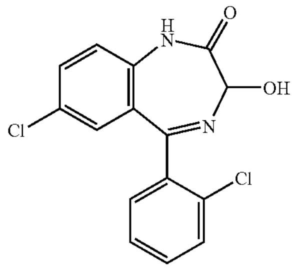 [SMILES: O=C1Nc2ccc(Cl)cc2C(c2ccccc2Cl)=NC1O]

Lorazepam is a benzodiazepine drug having sedative, tranquilizing, anticonvulsant, amnesic and muscle relaxing properties. It is classified as an anxiolytic. Lorazepam has also been shown to be useful in the treatment of nausea. The dosage of Lorazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Lorazepam may be manufactured using the process disclosed in U.S. Pat. No. 3,296,249, which is incorporated herein by reference in its entirety.

As a nasal formulation, lorazepam may be administered in 25 to 250 μl metered sprays. In some preferred embodiments, lorazepam is administered in 50 to 150 μl, especially about 100 μl, metered sprays. In some embodiments, a first metered spray is applied to a first nostril and if necessary a second metered spray is applied to a second nostril. In some optional embodiments, a third metered spray is applied to the first nostril. In some further embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Lorazepam may be combined with other pharmaceutically active ingredients, including other benzodiazepine compounds (such as diazepam) in a benzodiazepine drug formulation. In some embodiments, the ratio of lorazepam to the other pharmaceutically active ingredient is in one of the ranges from about 1:1000 to about 1000:1, about 1:100 to about 100:1 or about 1:10 to about 10:1. In some embodiments, the other pharmaceutically active ingredient is a benzodiazepine drug and the ratio of lorazepam to the other benzodiazepine drug is in one of the ranges from about 1:1000 to about 1000:1, about 1:100 to about 100:1 or about 1:10 to about 10:1. In some embodiments, the other pharmaceutically active ingredient is diazepam and the ratio of lorazepam to diazepam is about 1:1000 to about 1000:1, about 1:100 to about 100:1 or about 1:10 to about 10:1.

In some embodiments, Lorazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, Lorazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Lorazepam may be administered by the patient or other person (such as a healthcare professional) while the patient is in a non-seizing state to protect against seizure. Even where protection against seizure is not absolute, administration of lorazepam may reduce or ameliorate the intensity of seizure and/or reduce or ameliorate the frequency of seizure. In some embodiments, administration of lorazepam may prevent occurrence of seizure. In some embodiments, especially where the patient is prone to experiencing serial seizures or status epilepticus, administration of lorazepam may aid in interrupting the seizure cycle and may thus prevent the re-occurrence of seizure. In addition to the benzodiazepines (such as diazepam), other anti-convulsant drugs may be combined with lorazepam to provide a synergistic anticonvulsant effect.

Lorazepam may also be administered by another person (e.g. an acquaintance or associate, a family member or a health care professional) to the patient while the patient is in a state of seizure. Thus, one of the advantages of the nasal formulations according to the present invention is the ability to administer them in an acute therapeutic environment to treat the seizure victim. Among the beneficial therapeutic effects that may be imparted by acute nasal dosing of benzodiazepine anticonvulsants are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus the nasal lorazepam formulations of the invention provide fast onset of therapeutic benefit—in some instances less than about 30 minutes, less than about 15 minutes, less than about 10 minutes, and in some cases less than about 5 minutes. The nasal lorazepam formulations of the invention also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or at least often, precedes a patient's experiencing a seizure. In some embodiments of the invention, the method includes prompt administration of a nasal preparation of a benzodiazepine drug according to the invention during the aura. In some embodiments, such intra-aural administration of benzodiazepine drug by the intra-nasal route will prevent or at least ameliorate the effects (intensity, duration or both) of the impending seizure. Thus, in the context of this invention, prevention of seizure refers to a temporary forestalling of the onset of seizure, either with or without the benefit of a warning aura.

Medazepam ((7-chloro-1-methyl-5-phenyl-2,3-dihydro-1H-1,4-benzodiazepine)

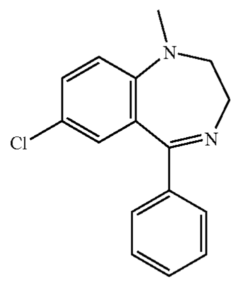 [SMILES: CN1CCN=C(c2ccccc2)c2cc(Cl)ccc21]

Medazepam is a benzodiazepine drug having sedative, tranquilizing, anticonvulsant, amnesic and muscle relaxing properties. It is classified as an anxiolytic. Medazepam has also been shown to be useful in the treatment of nausea. The dosage of Medazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Medazepam may be manufactured using the process disclosed in U.S. Pat. No. 3,243,427, which is incorporated herein by reference in its entirety.

As a nasal formulation, medazepam may be administered in 25 to 250 μl metered sprays. In some preferred embodiments, medazepam is administered in 50 to 150 μl, especially about 100 μl, metered sprays. In some embodiments, a first metered spray is applied to a first nostril and if necessary a second metered spray is applied to a second nostril. In some optional embodiments, a third metered spray is applied to the first nostril. In some further embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Medazepam may be combined with other pharmaceutically active ingredients, including other benzodiazepine compounds (such as diazepam) in a benzodiazepine drug formulation. In some embodiments, the ratio of medazepam to the other pharmaceutically active ingredient is in one of the ranges from about 1:1000 to about 1000:1, about 1:100 to about 100:1 or about 1:10 to about 10:1. In some embodiments, the other pharmaceutically active ingredient is a benzodiazepine drug and the ratio of medazepam to the other benzodiazepine drug is in one of the ranges from about 1:1000 to about 1000:1, about 1:100 to about 100:1 or about 1:10 to about 10:1. In some embodiments, the other pharmaceutically active ingredient is diazepam and the ratio of medazepam to diazepam is about 1:1000 to about 1000:1, about 1:100 to about 100:1 or about 1:10 to about 10:1.

In some embodiments, Medazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, Medazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Medazepam may be administered by the patient or other person (such as a healthcare professional) while the patient is in a non-seizing state to protect against seizure. Even where protection against seizure is not absolute, administration of medazepam may reduce or ameliorate the intensity of seizure and/or reduce or ameliorate the frequency of seizure. In some embodiments, administration of medazepam may prevent occurrence of seizure. In some embodiments, especially where the patient is prone to experiencing serial seizures or status epilepticus, administration of medazepam may aid in interrupting the seizure cycle and may thus prevent the re-occurrence of seizure. In addition to the benzodiazepines (such as diazepam), other anti-convulsant drugs may be combined with medazepam to provide a synergistic anticonvulsant effect.

Medazepam may also be administered by another person (e.g. an acquaintance or associate, a family member or a health care professional) to the patient while the patient is in a state of seizure. Thus, one of the advantages of the nasal formulations according to the present invention is the ability to administer them in an acute therapeutic environment to treat the seizure victim. Among the beneficial therapeutic effects that may be imparted by acute nasal dosing of benzodiazepine anticonvulsants are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus the nasal medazepam formulations of the invention provide fast onset of therapeutic benefit—in some instances less than about 30 minutes, less than about 15 minutes, less than about 10 minutes, and in some cases less than about 5 minutes. The nasal medazepam formulations of the invention also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or at least often, precedes a patient's experiencing a seizure. In some embodiments of the invention, the method includes prompt administration of a nasal preparation of a benzodiazepine drug according to the invention during the aura. In some embodiments, such intra-aural administration of benzodiazepine drug by the intra-nasal route will prevent or at least ameliorate the effects (intensity, duration or both) of the impending seizure. Thus, in the context of this invention, prevention of seizure refers to a temporary forestalling of the onset of seizure, either with or without the benefit of a warning aura.

Mexazolam (10-Chloro-11b-(2-chlorophenyl)-1,3,7,11b-tetrahydro-3-methyloxazolo[3,2-d][1,4]benzodiazepin-6(5H)-one)

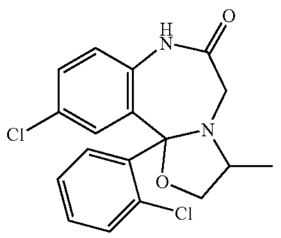 [SMILES: CC1COC2(c3ccccc3Cl)c3cc(Cl)ccc3NC(=O)CN12]

Mexazolam is a benzodiazepine drug having sedative, tranquilizing, anticonvulsant, amnesic and muscle relaxing properties. It is classified as an anxiolytic. Mexazolam has also been shown to be useful in the treatment of nausea. The dosage of Mexazolam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Mexazolam may be manufactured using the process disclosed in U.S. Pat. No. 3,722,371, which is incorporated herein by reference in its entirety.

As a nasal formulation, mexazolam may be administered in 25 to 250 μl metered sprays. In some preferred embodiments, mexazolam is administered in 50 to 150 μl, especially about 100 μl, metered sprays. In some embodiments, a first metered spray is applied to a first nostril and if necessary a second metered spray is applied to a second nostril. In some optional embodiments, a third metered spray is applied to the first nostril. In some further embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Mexazolam may be combined with other pharmaceutically active ingredients, including other benzodiazepine compounds (such as diazepam) in a benzodiazepine drug formulation. In some embodiments, the ratio of mexazolam to the other pharmaceutically active ingredient is in one of the ranges from about 1:1000 to about 1000:1, about 1:100 to about 100:1 or about 1:10 to about 10:1. In some embodiments, the other pharmaceutically active ingredient is a benzodiazepine drug and the ratio of mexazolam to the other benzodiazepine drug is in one of the ranges from about 1:1000 to about 1000:1, about 1:100 to about 100:1 or about 1:10 to about 10:1. In some embodiments, the other pharmaceutically active ingredient is diazepam and the ratio of mexazolam to diazepam is about 1:1000 to about 1000:1, about 1:100 to about 100:1 or about 1:10 to about 10:1.

In some embodiments, Mexazolam is used alone or in combination with other drugs to provide an anxiolytic effect, an anticonvulsant effect, a sedative effect, a skeletal muscle relaxant effect, an amnesic effect or combinations of the foregoing effects.

In some embodiments, Mexazolam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Mexazolam may be administered by the patient or other person (such as a healthcare professional) while the patient is in a non-seizing state to protect against seizure. Even where protection against seizure is not absolute, administration of mexazolam may reduce or ameliorate the intensity of seizure and/or reduce or ameliorate the frequency of seizure. In some embodiments, administration of mexazolam may prevent occurrence of seizure. In some embodiments, especially where the patient is prone to experiencing serial seizures or status epilepticus, administration of mexazolam may aid in interrupting the seizure cycle and may thus prevent the re-occurrence of seizure. In addition to the benzodiazepines (such as diazepam), other anti-convulsant drugs may be combined with mexazolam to provide a synergistic anticonvulsant effect.

Mexazolam may also be administered by another person (e.g. an acquaintance or associate, a family member or a health care professional) to the patient while the patient is in a state of seizure. Thus, one of the advantages of the nasal formulations according to the present invention is the ability to administer them in an acute therapeutic environment to treat the seizure victim. Among the beneficial therapeutic effects that may be imparted by acute nasal dosing of benzodiazepine anticonvulsants are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus the nasal mexazolam formulations of the invention provide fast onset of therapeutic benefit—in some instances less than about 30 minutes, less than about 15 minutes, less than about 10 minutes, and in some cases less than about 5 minutes. The nasal mexazolam formulations of the invention also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or at least often, precedes a patient's experiencing a seizure. In some embodiments of the invention, the method includes prompt administration of a nasal preparation of a benzodiazepine drug according to the invention during the aura. In some embodiments, such intra-aural administration of benzodiazepine drug by the intra-nasal route will prevent or at least ameliorate the effects (intensity, duration or both) of the impending seizure. Thus, in the context of this invention, prevention of seizure refers to a temporary forestalling of the onset of seizure, either with or without the benefit of a warning aura.

Midazolam (8-chloro-6-(2-fluorophenyl)-1-methyl-4H-imidazo[1,5-a]benzodiazepine)

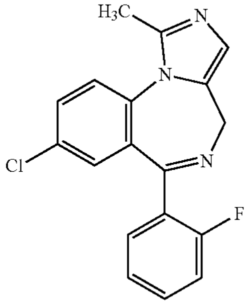 [SMILES: Cc1ncc2n1-c1ccc(Cl)cc1C(c1ccccc1F)=NC2]

Midazolam is a tricyclic benzodiazepine having anxiolytic, amnesic, hypnotic, anticonvulsant, skeletal muscle relaxant and sedative properties. Midazolam is considered soluble in water at a pH lower than about 4, but is relatively insoluble in most aqueous solutions at neutral pH (e.g. about 6 to 8). Accordingly, nanoparticulates of midazolam may be formulated at or near neutral pH. Thus it is desirable in some embodiments for aqueous nasal preparations of midazolam to have a pH above about 5.5, preferably above about 6.0, or above about 6.5. In some preferred embodiments, the pH is between about 6 and 9, between about 6 and 8. It is considered that nanoparticulate aqueous preparations of midazolam are particularly suitable for nasal administration as the lipid-soluble (at approximately neutral pH) midazolam particles are rapidly absorbed across nasal mucosa, leading to efficient uptake of midazolam. It is further considered that nanoparticulate midazolam may be formulated in a non-aqueous delivery vehicle, such as is known in the aerosol administration art, such as hydrofluorocarbon propellants, hydrocarbon propellants, etc.

The dosage of midazolam varies by indication, however it is expected that a therapeutic dose will be in the range of about 0.1 to about 20, preferably about 0.2 to about 10 mg per dose, from 1 to 8, preferably from 2 to 8, and in some preferred embodiments about 4 to about 6 times per day. Midazolam may be manufactured using the process disclosed in one of U.S. Pat. No. 4,280,957 or U.S. Pat. No. 5,831,089, each of which is incorporated herein by reference in its entirety.

As a nasal formulation, midazolam may be administered in 25 to 250 μl metered sprays. In some preferred embodiments, midazolam is administered in 50 to 150 μl, especially about 100 μl, metered sprays. In some embodiments, a first metered spray is applied to a first nostril and if necessary a second metered spray is applied to a second nostril. In some optional embodiments, a third metered spray is applied to the first nostril. In some further embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Midazolam may be combined with other pharmaceutically active ingredients, including other benzodiazepine compounds (such as diazepam) in a benzodiazepine drug formulation. In some embodiments, the ratio of midazolam to the other pharmaceutically active ingredient is in one of the ranges from about 1:1000 to about 1000:1, about 1:100 to about 100:1 or about 1:10 to about 10:1. In some embodiments, the other pharmaceutically active ingredient is a benzodiazepine drug and the ratio of midazolam to the other benzodiazepine drug is in one of the ranges from about 1:1000 to about 1000:1, about 1:100 to about 100:1 or about 1:10 to about 10:1. In some embodiments, the other pharmaceutically active ingredient is diazepam and the ratio of midazolam to diazepam is about 1:1000 to about 1000:1, about 1:100 to about 100:1 or about 1:10 to about 10:1.

In some embodiments, Midazolam is used alone or in combination with other drugs to provide an anxiolytic effect, an anticonvulsant effect, a sedative effect, a skeletal muscle relaxant effect, an amnesic effect or combinations of the foregoing effects.

In some embodiments, Midazolam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Midazolam may be administered by the patient or other person (such as a healthcare professional) while the patient is in a non-seizing state to protect against seizure. Even where protection against seizure is not absolute, administration of midazolam may reduce or ameliorate the intensity of seizure and/or reduce or ameliorate the frequency of seizure. In some embodiments, administration of midazolam may prevent occurrence of seizure. In some embodiments, especially where the patient is prone to experiencing serial seizures or status epilepticus, administration of midazolam may aid in interrupting the seizure cycle and may thus prevent the re-occurrence of seizure. In addition to the benzodiazepines (such as diazepam), other anti-convulsant drugs may be combined with midazolam to provide a synergistic anticonvulsant effect.

Midazolam may also be administered by another person (e.g. an acquaintance or associate, a family member or a health care professional) to the patient while the patient is in a state of seizure. Thus, one of the advantages of the nasal formulations according to the present invention is the ability to administer them in an acute therapeutic environment to treat the seizure victim. Among the beneficial therapeutic effects that may be imparted by acute nasal dosing of benzodiazepine anticonvulsants are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus the nasal midazolam formulations of the invention provide fast onset of therapeutic benefit—in some instances less than about 30 minutes, less than about 15 minutes, less than about 10 minutes, and in some cases less than about 5 minutes. The nasal midazolam formulations of the invention also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or at least often, precede a patient's experiencing a seizure. In some embodiments of the invention, the method includes prompt administration of a nasal preparation of a benzodiazepine drug according to the invention during the aura. In some embodiments, such intra-aural administration of benzodiazepine drug by the intra-nasal route will prevent or at least ameliorate the effects (intensity, duration or both) of the impending seizure. Thus, in the context of this invention, prevention of seizure refers to a temporary forestalling of the onset of seizure, either with or without the benefit of a warning aura.

Temazepam (7-chloro-1-methyl-5-phenyl-3-hydroxy-1,3-dihydro-2H-1,4-benzodiazepin-2-one)

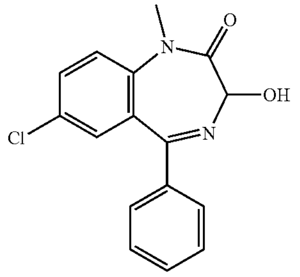 [SMILES: CN1C(=O)C(O)N=C(c2ccccc2)c2cc(Cl)ccc21]

Temazepam is a benzodiazepine drug having sedative, tranquilizing, anticonvulsant, amnesic and muscle relaxing properties. It is classified as an anxiolytic. Temazepam has also been shown to be useful in the treatment of nausea. The dosage of Temazepam varies by indication, however it is expected that a therapeutic dose will be in the range of about 1 to about 50, preferably about 5 to about 30 mg per dose, from 1 to 8, preferably from 2 to 8, and in some preferred embodiments about 4 to about 6 times per day. Temazepam may be manufactured using the process disclosed in U.S. Pat. No. 3,340,253 or U.S. Pat. No. 3,374,225, each of which is incorporated herein by reference in its entirety.

As a nasal formulation, temazepam may be administered in 25 to 250 μl metered sprays. In some preferred embodiments, temazepam is administered in 50 to 150 μl, especially about 100 μl, metered sprays. In some embodiments, a first metered spray is applied to a first nostril and if necessary a second metered spray is applied to a second nostril. In some optional embodiments, a third metered spray is applied to the first nostril. In some further embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Temazepam may be combined with other pharmaceutically active ingredients, including other benzodiazepine compounds (such as diazepam) in a benzodiazepine drug formulation. In some embodiments, the ratio of temazepam to the other pharmaceutically active ingredient is in one of the ranges from about 1:1000 to about 1000:1, about 1:100 to about 100:1 or about 1:10 to about 10:1. In some embodiments, the other pharmaceutically active ingredient is a benzodiazepine drug and the ratio of temazepam to the other benzodiazepine drug is in one of the ranges from about 1:1000 to about 1000:1, about 1:100 to about 100:1 or about 1:10 to about 10:1. In some embodiments, the other pharmaceutically active ingredient is diazepam and the ratio of temazepam to diazepam is about 1:1000 to about 1000:1, about 1:100 to about 100:1 or about 1:10 to about 10:1.

In some embodiments, Temazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, Temazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Temazepam may be administered by the patient or other person (such as a healthcare professional) while the patient is in a non-seizing state to protect against seizure. Even where protection against seizure is not absolute, administration of temazepam may reduce or ameliorate the intensity of seizure and/or reduce or ameliorate the frequency of seizure. In some embodiments, administration of temazepam may prevent occurrence of seizure. In some embodiments, especially where the patient is prone to experiencing serial seizures or status epilepticus, administration of temazepam may aid in interrupting the seizure cycle and may thus prevent the re-occurrence of seizure. In addition to the benzodiazepines (such as diazepam), other anti-convulsant drugs may be combined with temazepam to provide a synergistic anticonvulsant effect.

Temazepam may also be administered by another person (e.g. an acquaintance or associate, a family member or a health care professional) to the patient while the patient is in a state of seizure. Thus, one of the advantages of the nasal formulations according to the present invention is the ability to administer them in an acute therapeutic environment to treat the seizure victim. Among the beneficial therapeutic effects that may be imparted by acute nasal dosing of benzodiazepine anticonvulsants are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus the nasal temazepam formulations of the invention provide fast onset of therapeutic benefit—in some instances less than about 30 minutes, less than about 15 minutes, less than about 10 minutes, and in some cases less than about 5 minutes. The nasal temazepam formulations of the invention also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or at least often, precedes a patient's experiencing a seizure. In some embodiments of the invention, the method includes prompt administration of a nasal preparation of a benzodiazepine drug according to the invention during the aura. In some embodiments, such intra-aural administration of benzodiazepine drug by the intra-nasal route will prevent or at least ameliorate the effects (intensity, duration or both) of the impending seizure. Thus, in the context of this invention, prevention of seizure refers to a temporary forestalling of the onset of seizure, either with or without the benefit of a warning aura.

In some embodiments, other drugs may be included in the aerosol (nasal or pulmonary) formulations of the invention. For example in the multimodal particulate compositions (e.g. the bimodal particulate compositions), in addition to the herein recited benzodiazepines (e.g. diazepam) that may be used, either alone or in combination with one or more diazepines, include other anticonvulsants, such as: paraldehyde; aromatic allylic alcohols (such as stiripentol); barbiturates (e.g. phenobarbital, primidone, methylphenobarbital, metharbital and barbexaclone); bromides (such as potassium bromide); carbamates (such as felbamate); carboxamides (such as carbamazepine and oxcarbazepine); fatty acids (such as valproic acid, sodium valproate, and divalproex sodium, vigabatrin, progabide, tiagabine); fructose, topiramate, Gaba analogs (e.g. gabapentin and pregabalin); hydantoins (e.g. ethotoin, phenyloin, mephenyloin and fosphenyloin); oxazolidinediones (such as paramethadione, trimethadione, ethadione); propionates (e.g. beclamide), pyrimidinediones (e.g. primidone); pyrrolidines (e.g. brivaracetam, levetiracetam and seletracetam); succinimides (e.g. ethosuximide, phensuximide and mesuximide); sulfonamides (e.g. acetazolamide, sulthiame, methazolamide and zonisamide); triazines (such as lamotrigine); ureas (such as pheneturide, phenacemide); valproylamides (such as valpromide and valnoctamide); as well as other anticonvulsants or pharmaceutically acceptable salts or combinations thereof.

In some embodiments, other pharmaceutically active ingredients that can be administered intranasally or pulmonarily (especially as multimodal, e.g. bimodal particulate compositions) either alone or in combination with one or more benzodiazepines (such as diazepam) or other active pharmaceutical ingredient include: insulin, calcitonins (for example porcine, human, salmon, chicken, or eel) and synthetic modifications thereof, enkephalins, LHRH and analogues (Nafarelin, Buserelin, Zolidex), GHRH (growth hormone releasing hormone), nifedipin, THF (thymic humoral factor), CGRP (calcitonin gene related peptide), atrial natriuretic peptide, antibiotics, metoclopramide, ergotamine, Pizotizin, nasal vaccines (particularly HIV vaccines, measles, rhinovirus Type 13 and respiratory syncitial virus), pentamidine, CCK (Cholecystikinine), DDVAP, Interferons, growth hormone (solatotropir polypeptides or their derivatives (preferably with a molecular weight from 1000 to 300000), secretin, bradykinin antagonists, GRF (Growth releasing factor), THF, TRH (Thyrotropin releasing hormone), ACTH analogues, IGF (Insulin like growth factors), CGRP (Calcitorin gene related peptide) Atrial Natriuretic peptide, Vasopressin and analogues (DDAVP, Lypressin), Metoclopramide, Migraine treatment (Dihydroergotamine, Ergometrine, Ergotamine, Pizotizin), Nasal Vaccines (Particularly AIDS vaccines) FACTOR VIII, Colony Stimulating factors, G-CSF (granulocyte-colony stimulating factor), EPO (Erythropoitin) PTH (Parathyroid hormone) or pharmaceutically acceptable salts or combinations thereof.

In some embodiments, other pharmaceutically active ingredients that can be administered intranasally or pulmonarily (especially as multimodal, e.g. bimodal particulate compositions) either alone or in combination with one or more benzodiazepines (such as diazepam) or other active pharmaceutical ingredient include: antibiotics and antimicrobial agents such as tetracyline hydrochloride, leucomycin, penicillin, penicillin derivatives, erythromycin, gentamicin, sulphathiazole and nitrofurazone; local anaesthetics such as benzocaine; vasoconstrictors such as phenylephrine hydrochloride, tetrahydrozoline hydrochloride, naphazoline nitrate, oxymetazoline hydrochloride and tramazoline hydrochloride; cardiotonics such as digitalis and digoxin; vasodilators such as nitroglycerine and papaverine hydrochloride; antiseptics such as chlorhexidine hydrochloride, hexylresorcinol, dequaliniumchloride and ethacridine; enzymes such as lysozyme chloride, dextranase; bone metabolism controlling agents such as vitamin D, active vitamin D and vitamin C; sex hormones; hypotensives; sedatives; anti-tumor agents; steroidal anti-inflammatory agents such as hydrocortisone, prednisone, fluticasone, prednisolone, triamcinolone, triamcinolone acetonide, dexamethas one, betamethas one, beclomethas one, and beclomethasone dipropionate; non-steroidal anti-inflammatory agents such as acetaminophen, aspirin, aminopyrine, phenylbutazone, medanamic acid, ibuprofen, diclofenac sodium, indomethacine, colchicine, and probenocid; enzymatic anti-inflammatory agents such as chymotrypsin and bromelain seratiopeptidase; anti-histaminic agents such as diphenhydramine hydrochloride, chloropheniramine maleate and clemastine; anti-allergic agents and antitussive-expectorant antasthmatic agents such as sodium chromoglycate, codeine phosphate, and isoproterenol hydrochloride or pharmaceutically acceptable salts or combinations thereof.

In some embodiments, the molecular weight of the drug is preferably in the range 100 to 300,000, although drugs with other molecular weights may be employed in some embodiments.

In order to improve the properties, appearance or odor of the pharmaceutical composition, it may, in some embodiments, contain any of known additives such as coloring agents, preservatives, antiseptics, etc. Examples of coloring agents include β-carotene, Red No. 2 and Blue No. 1; examples of preservatives include stearic acid, ascorbyl stearate and ascorbic acid; examples of antiseptics include p-hydroxy-benzoate, phenol, chlorobutanol, benzylkonium chloride etc.; and examples of corrigents include menthol and citrus perfume.

In some embodiments, the drug delivery system of the invention may advantageously comprise an absorption enhancer. The term "enhancer", means any material which acts to increase absorption across the mucosa and/or increases bioavailability. In some embodiments, such materials include mucolytic agents, degradative enzyme inhibitors and compounds which increase permeability of the mucosal cell membranes. Whether a given compound is an "enhancer" can be determined by comparing two formulations comprising a non-associated, small polar molecule as the drug, with or without the enhancer, in an in vivo or good model test and determining whether the uptake of the drug is enhanced to a clinically significant degree. The enhancer should not produce any problems in terms of chronic toxicity because in vivo the enhancer should be non-irritant and/or rapidly metabolized to a normal cell constituent that does not have any significant irritant effect.

In some embodiments, preferred enhancing materials lysophospholipids, for example lysophosphatidylcholine obtainable from egg or soy lecithin. Other lysophosphatidylcholines that have different acyl groups as well as lyso compounds produced from phosphatidylethanolamines and phosphatidic acid which have similar membrane modifying properties may be used. Acyl camitines (e.g. palmitoyl-dl-camitine-chloride) is an alternative. In some embodiments, a suitable concentration is from 0.02 to 20% w/v.

In some embodiments, enhancing agents that are appropriate include chelating agents (EGTA, EDTA, alginates), surface active agents (especially non-ionic materials), acyl glycerols, fatty acids and salts, tyloxapol and biological detergents listed in the SIGMA Catalog, 1988, page 316-321 (which is incorporated herein by reference). Also agents that modify the membrane fluidity and permeability are appropriate such as enamines (e.g. phenylalanine enamine of ethylacetoacetate), malonates (e.g. diethyleneoxymethylene malonate), salicylates, bile salts and analogues and fusidates. Suitable concentrations are up to 20% w/v.

In some embodiments, the invention takes advantage of delivery of a drug incorporated into or onto a bioadhesive microsphere with an added pharmaceutical adjuvant applies to systems that contain active drug and mucolytic agent, peptidase inhibitors or non-drug polypeptide substrate singly or in combination. Suitably mucolytic agents are thiol-containing compounds such as N-acetylcysteine and derivatives thereof. Peptide inhibitors include actinonin, amastatin, bestatin, chloroacetyl-HOLeu-Ala-Gly-NH.sub.2, diprotin A and B, ebelactone A and B, E-64, leupeptin, pepstatin A, phisphoramidon, H-Thr-(tBu)-Phe-Pro-OH, aprotinin, kallikrein, chymostatin, benzamidine, chymotrypsin and trypsin. Suitable concentrations are from 0.01 to 10% w/v. The person skilled in the art will readily be able to determine whether an enhancer should be included.

Other Active Pharmaceutical Ingredients

Other active pharmaceutical ingredients that may be formulated as multimodal nanoparticulate formulations, surface active agent-coated nanoparticulate formulations and non-aqueous nanoparticulate suspension according to embodiments of the invention include those active pharmaceutical ingredients that penetrate the mucosa of the lungs, nasal cavity, oropharyngeal surfaces and/or the gastrointestinal tract. Especially suitable are those active pharmaceutical ingredients that are subject to rapid degradation in the liver, as absorption of active ingredient across the nasal and pulmonary mucosa permits the active ingredient to avoid the portal vein, thereby greatly reducing the first-pass effect. Suitable active pharmaceutical ingredients include: other anticonvulsants, such as: paraldehyde; aromatic allylic alcohols (such as stiripentol); barbiturates (e.g. phenobarbital, primidone, methylphenobarbital, metharbital and barbexaclone); bromides (such as potassium bromide); carbamates (such as felbamate); carboxamides (such as carbamazepine and oxcarbazepine); fatty acids (such as valproic acid, sodium valproate, and divalproex sodium, vigabatrin, progabide, tiagabine); topiramate, Gaba analogs (e.g. gabapentin and pregabalin); hydantoins (e.g. ethotoin, phenyloin, mephenyloin and fosphenyloin); oxazolidinediones (such as paramethadione, trimethadione, ethadione); propionates (e.g. beclamide), pyrimidinediones (e.g. primidone); pyrrolidines (e.g. brivaracetam, levetiracetam and seletracetam); succinimides (e.g. ethosuximide, phensuximide and mesuximide); sulfonamides (e.g. acetazolamide, sulthiame, methazolamide and zonisamide); triazines (such as lamotrigine); ureas (such as pheneturide, phenacemide); valproylamides (such as valpromide and valnoctamide); as well as other anticonvulsants or pharmaceutically acceptable salts or combinations thereof.

In some embodiments, other pharmaceutically active ingredients that can be administered intranasally or pulmonarily (especially as multimodal, e.g. bimodal particulate compositions) either alone or in combination with one or more benzodiazepines (such as diazepam) or other active pharmaceutical ingredient include: insulin, calcitonins (for example porcine, human, salmon, chicken, or eel) and synthetic modifications thereof, enkephalins, LHRH and analogues (Nafarelin, Buserelin, Zolidex), GHRH (growth hormone releasing hormone), nifedipin, THF (thymic humoral factor), CGRP (calcitonin gene related peptide), atrial natriuretic peptide, antibiotics, metoclopramide, ergotamine, Pizotizin, nasal vaccines (particularly HIV vaccines, measles, rhinovirus Type 13 and respiratory syncitial virus), pentamidine, CCK (Cholecystikinine), DDVAP, Interferons, growth hormone (solatotropir polypeptides or their derivatives (preferably with a molecular weight from 1000 to 300000), secretin, bradykinin antagonists, GRF (Growth releasing factor), THF, TRH (Thyrotropin releasing hormone), ACTH analogues, IGF (Insulin like growth factors), CGRP (Calcitorin gene related peptide) Atrial Natriuretic peptide, Vasopressin and analogues (DDAVP, Lypressin), Metoclopramide, Migraine treatment (Dihydroergotamine, Ergometrine, Ergotamine, Pizotizin), Nasal Vaccines (Particularly AIDS vaccines) FACTOR VIII, Colony Stimulating factors, G-CSF (granulocyte-colony stimulating factor), EPO (Erythropoitin) PTH (Parathyroid hormone) or pharmaceutically acceptable salts or combinations thereof.

In some embodiments, other pharmaceutically active ingredients that can be administered intranasally or pulmonarily (especially as multimodal, e.g. bimodal particulate compositions) either alone or in combination with one or more benzodiazepines (such as diazepam) or other active pharmaceutical ingredient include: pain medications, such as prochloroperazine, acetaminophen, fentanyl, hydrocodone, etodolac, oxycodone, naproxen sodium, butorphanol, ketoprofen, nalbuphine, pentazocine, ibuprofen, diclofenac, meperidine, oxymorphone, butalbital, propoxyphene, gabapentin, and/or indomethacine; barbiturates, such as mephobarbitol, and/or pentobarbital; antiinsomnia drugs, such as zolpidem, zaleplon, eszopiclone, doxepine; drugs for treating addiction, such as methadone, buprenorphine, naltrexone, naloxone; antibiotics and antimicrobial agents such as tetracyline hydrochloride, leucomycin, penicillin, penicillin derivatives, erythromycin, gentamicin, sulphathiazole and nitrofurazone; local anaesthetics such as benzocaine; vasoconstrictors such as phenylephrine hydrochloride, tetrahydrozoline hydrochloride, naphazoline nitrate, oxymetazoline hydrochloride and tramazoline hydrochloride; cardiotonics such as digitalis and digoxin; vasodilators such as nitroglycerine and papaverine hydrochloride; antiseptics such as chlorhexidine hydrochloride, hexylresorcinol, dequaliniumchloride and ethacridine; enzymes such as lysozyme chloride, dextranase; bone metabolism controlling agents such as vitamin D, active vitamin D and vitamin C; sex hormones; hypotensives; sedatives; anti-tumor agents; steroidal anti-inflammatory agents such as hydrocortisone, prednisone, fluticasone, prednisolone, triamcinolone, triamcinolone acetonide, dexamethas one, betamethas one, beclomethas one, and beclomethasone dipropionate; non-steroidal anti-inflammatory agents such as acetaminophen, aspirin, aminopyrine, phenylbutazone, medanamic acid, ibuprofen, diclofenac sodium, indomethacine, colchicine, and probenocid; enzymatic anti-inflammatory agents such as chymotrypsin and bromelain seratiopeptidase; anti-histaminic agents such as diphenhydramine hydrochloride, chloropheniramine maleate and clemastine; anti-allergic agents and antitussive-expectorant antasthmatic agents such as sodium chromoglycate, codeine phosphate, and isoproterenol hydrochloride; drugs for treating spasticity, such as baclofen, dantrolene, tizanidine, phenol, clonidine, gabapentin and/or acamprosate; antiemetics, such as dolasetron, granisetron, ondansetron, tropisetron, palonosetron, domperidone, droperidol, haloperidol, chlorpromazine, promethazine, prochlorperazine, metoclopramide, alizapride, cyclizine, diphenhydramine, dimenhydrinate, meclizine, promethazine, hydroxyzine, and/or one or more cannabinoids; antipsychotics, such as haloperidol, chlorpromazine, fluphenazine, perphenazine, prochlorperazine, thioridazine, trifluoperazine, mesoridazine, promazine, triflupromazine, levomepromazine, promethazine, chlorprothixene, flupenthixol, thiothixene, zuclopenthixol, clozapine, olanzapine, risperidone, quetiapine, ziprasidone, amisulpride, and/or asenapine; short-acting Beta$_2$-adrenergic agonists, such as salbutamol (albuterol), levosalbutamol, terbutaline, pirbuterol, procaterol, metaproerenol, fenoterol, and/or bitolterol mesylate, long-acting Beta$_2$-adrenergic agonists, such as salmeterol, formoterol, bambuterol, clenbuterol, and/or indacaterol; muscarinic antagonists, such as atropine, scopolamine, ipratropium, tropicamide, pirenzepine, diphenhydramine, dimenhydrinate, dicyclomine, flavoxate, tiotropium, cyclopentolate, atropine methonitrate, trihexylphenidyl, tolterodine, solifenacin, darifenacin, benatropine, and/or mebeverine; corticosteroids, such as beclomethasone, budesonide, flunisolide, fluticasone, mometasone, and/or triamcinolone; atypical antipsychotic medications, such as clozapine, risperidone, olanzapine, quetiapine, ziprasidone, aripiprazole, paliperidone, asenapine, iloperidone, sertindole, zotepine, amisulpride, bifenprunox, and/or melperone; selective serotonin reuptake inhibitors (SSRIs), such as citalopram, dapoxetine, escitalopram, fluoxetine, fluvoxamine, paroxetine, sertraline; tricyclic antidepressants, such as amitriptyline, amoxapine, clomipramine, desipramine, dosulepin hydrochloride, doxepin, imipramine, iprindole, lofepramine, nortriptyline, opipramol, protriptyline, and/or trimipramine; serotonin norepinephrine reuptake inhibitors (SNRIs), such as venlafaxine, desvenlafaxine, sibutramine, nefazodone, milnacipran, desipramine, duloxetine, and/or bicifadine; zimelidine; or pharmaceutically acceptable salts or combinations thereof.

In some embodiments, other pharmaceutically active ingredients that can be administered intranasally or pulmonarily (especially as multimodal, e.g. bimodal particulate compositions) either alone or in combination with one or more benzodiazepines (such as diazepam) or other active pharmaceutical ingredient include anticancer or antiproliferative chemotherapeutic agents such as: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

In some embodiments, other pharmaceutically active ingredients that can be administered intranasally or pulmonarily (especially as multimodal, e.g. bimodal particulate compositions) either alone or in combination with one or more benzodiazepines (such as diazepam) or other active pharmaceutical ingredient include: Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with the compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

In some embodiments, the molecular weight of the drug is preferably in the range 100 to 300,000, although drugs with other molecular weights may be employed in some embodiments.

Surface Active Agents (Surface Stabilizers; Surface Modifiers; Surfactants)

In some embodiments, surface active agents, which can also be referred to as surface stabilizers, surface modifiers or surfactants, can preferably be selected from known organic and inorganic pharmaceutical excipients. Such excipients may include polymers, low molecular weight oligomers, natural products, and surfactants. In some embodiments, surface active agents include nonionic or ionic surfactants.

In some embodiments, surface active agents include gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., TWEEN 20® and TWEEN 80® (ICI Specialty Chemicals)); polyethylene glycols (e.g., Carbowaxes 3550® and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)); Duponol P®, which is a sodium lauryl sulfate (DuPont); Tritons X-200, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-lOG® or Surfactant 10-G® (Olin Chemicals, Stamford, Conn.); Crodestas SL-40® (Croda, Inc.); and SA9OHCO, which is $C_{18}H_{37}CH_2(CON(CH_3)—CH_2(CHOH)_4(CH_{20}H)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-.beta.-D-glucopyranoside; octyl β-D-thioglucopyranoside; etc.

In some embodiments, surface active agents include one or more of: hypromellose, hydroxypropylcellulose, polyvinylpyrrolidone, sodium lauryl sulfate, dioctylsulfosuccinate, gelatin, casein, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, carboxymethylcellulose calcium, carboxymethylcellulose sodium, methylcellulose, hydroxyethylcellulose, hypromellose phthalate, noncrystalline cellulose, magnesium aluminum silicate, triethanolamine, polyvinyl alcohol, tyloxapol, poloxamers, poloxamines, Tetronic 1508®, an alkyl aryl polyether sulfonate, a mixture of sucrose stearate and sucrose distearate, p-isononylphenoxypoly-(glycidol), Crodestas SL-40® (Croda, Inc.); and SA9OHCO, decanoyl-N-methylglucamide; n-decyl (–D-glucopyranoside; n-decyl (–D-maltopyranoside; n-dodecyl (–D-glucopyranoside; n-dodecyl (–D-maltoside; heptanoyl-N-methylglucamide; n-heptyl-(–D-glucopyranoside; n-heptyl (–D-thioglucoside; n-hexyl (–D-glucopyranoside; nonanoyl-N-methylglucamide; n-noyl (–D-glucopyranoside; octanoyl-N-methylglucamide; n-octyl-(–D-glucopyranoside; octyl (–D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, cationic polymers, cationic biopolymers, cationic polysaccharides, cationic cellulosics, cationic alginates, cationic phospholipids, cationic nonpolymeric compounds, poly-n-methylpyridinium, anthryul pyridinium chloride, cationic phospholipids, chitosan, polylysine, polyvinylimidazole, polybrene, polymethylmethacrylate trimethylammoniumbromide bromide, hexyldesyltrimethylammonium bromide, polyvinylpyrrolidone-2-dimethylaminoethyl methacrylate dimethyl sulfate, cationic lipids, sulfonium, phosphonium, quarternary ammonium compounds, stearyltrimethylammonium chloride, benzyl-di(2-chloroethyl) ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium bromide, $C_{12-15}$dimethyl hydroxyethyl ammonium chloride, $Cl_{12-15}$dimethyl hydroxyethyl ammonium bromide, coconut dimethyl hydroxyethyl ammonium chloride, coconut dimethyl hydroxyethyl ammonium bromide, myristyl trimethyl ammonium methyl sulfate, lauryl dimethyl benzyl ammonium chloride, lauryl dimethyl benzyl ammonium bromide, lauryl dimethyl $(ethenoxy)_4$ ammonium chloride, lauryl dimethyl $(ethenoxy)_4$ ammonium bromide, N-alkyl $(C_{12-18})$dimethylbenzyl ammonium chloride, N-alkyl $(C_{14-18})$dimethyl-benzyl ammonium chloride, N-tetradecylidmethylbenzyl ammonium chloride monohydrate, dimethyl didecyl ammonium chloride, N-alkyl and $(C_{12-14})$ dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl$(C_{12-14})$ dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride, dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, POLYQUAT, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, MIRAPOL, ALKAQUAT, alkyl pyridinium salts, amines, alkylamines, dialkylamines, alkanolamines, polyethylenepolyamines, N,N-dialkylaminoalkyl acrylates, vinyl pyridine, amine salts, lauryl amine acetate, stearyl amine acetate, alkylpyridinium salt, alkylimidazolium salt, amine oxides, imide azolinium salts, protonated quaternary acrylamides, methylated quaternary polymers, and cationic guar.

Thus, in some embodiments, the invention provides a pharmaceutical composition of an anticonvulsant agent comprising solid particles of the agent coated with one or more surface modifiers, wherein the particles have an average effective particle size of less than about 50 nm to less than about 1000 nm. In some embodiments, the surface modifier is selected from the group consisting of: anionic surfactants, cationic surfactants, zwitterionic surfactants, nonionic surfactants, surface active biological modifiers, and combinations thereof. In some embodiments, the anionic surfactant is selected from the group consisting of: alkyl sulfonates, alkyl phosphates, triethanolamine stearate, sodium lauryl sulfate, sodium dodecylsulfate, alkyl polyoxyethylene sulfates, sodium alginate, dioctyl sodium sulfosuccinate, sodium carboxymethylcellulose, and calcium carboxymethylcellulose. In some embodiments, the cationic surfactant is selected from the group consisting of quaternary ammonium compounds, benzalkonium chloride, dimethylaminoethanecarbamoyl cholesterol, alkyl pyridinium halides, n-octylamine and oleylamine. In some embodiments, the anionic surfactant is a natural or synthetic phospholipid. In some embodiments, the cationic surfactant is a natural or synthetic phospholipid. In some embodiments, the zwitterionic surfactant is a phospholipid, and wherein the phospholipid is natural or synthetic. In some embodiments, the nonionic surfactant is selected from the group consisting of: polyoxyethylene fatty alcohol ethers, polyoxyethylene sorbitan fatty acid esters, polyoxyethylene fatty acid esters, sorbitan esters, glycerol monostearate, polyethylene glycols, polypropylene glycols, cetyl alcohol, cetostearyl alcohol, aryl alkyl polyether alcohols, polyoxyethylene-polyoxypropylene copolymers, poloxamines, methylcellulose, hydroxycellulose, hydroxy propylcellulose, hydroxy propylmethylcellulose, noncrystalline cellulose, polysaccharides, starch, starch derivatives, hydroxyethylstarch, polyvinyl alcohol, and polyvinylpyrrolidone. In some embodiments, the surface active biological modifier is selected from the group consisting of proteins, polysaccharides, and combinations thereof. In some embodiments, the polysaccharide is selected from the group consisting of starches, heparin and chitosans. In some embodiments, the protein is selected from the group consisting of albumin and casein. In some embodiments, the surface modifier comprises a copolymer of oxyethylene and oxypropylene. In some embodiments, the copolymer of oxyethylene and oxypropylene is a block copolymerize, the anticonvulsant agent is a tricyclic anticonvulsant agent. In some embodiments, the tricyclic anticonvulsant agent is carbamazepine, diazepam, lorazepam, midazolam or clonazepam. In some embodiments, the anticonvulsant agent is a phenyltriazine. In some embodiments, the anticonvulsant agent is lamotrigine. In some embodiments, the antidementia agent alprazolam. In some embodiments, the anticonvulsant is the antidementia agent risperidone. In some embodiments, the anticonvulsant is the antidementia agent sertraline.

Pharmaceutically Acceptable Salts

Benzodiazepines have the generally basic structure:

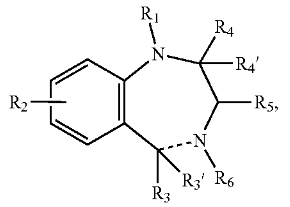

wherein $R_1$-$R_5$ are substituents. In particular embodiments, $R_1$ is an optionally substituted alkyl or forms a ring with $R_4$, $R_2$ is a halogen (e.g. Cl, Br), $R_3$ is optionally substituted aryl (e.g. 2-Chloro or 2-Fluorophenyl), $R_5$ is H or OH, $R_4$ and $R_4$' together form a carbonyl (C═O) with the carbon to which they are attached or $R_4$ and $R_1$ form an optionally substituted heterocyclic ring with the diazepine ring atoms to which they are respectively attached; $R_3$' and $R_6$ together form a double bond or may be combined to form an optionally substituted heterocyclic ring along with the diazepine ring atoms to which they are respectively attached. Such basic compounds may form acid addition salts with pharmaceutically acceptable acids, such as pharmaceutically acceptable mineral acids and pharmaceutically acceptable organic acids.

Pharmaceutically acceptable mineral acids include HCl, $H_2SO_4$, $H_2SO_3$, $H_3PO_4$, $H_3PO_3$, etc. Pharmaceutically acceptable organic acids include acetic acid, benzoic acid, tartaric acid, citric acid, oxalic acid, maleic acid, malonic acid, etc. Thus, in some embodiments, the pharmaceutically acceptable acid may be selected from the group consisting of: 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acidascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acidfumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, benzenesulfonic acid (besylic acid), naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p) and undecylenic acid. Other pharmaceutically acceptable acids may be pharmaceutically acceptable acidic (anionic) polymers or pharmaceutically acceptable amphoteric polymers. One skilled in the art will recognize that other basic active pharmaceutical ingredients may be combined with the foregoing acids to produce acid addition salts. Likewise the person skilled in the art will recognize that in some embodiments it may be advantageous that some or all of the added acid be an active pharmaceutical ingredient in its own right.

In some embodiments, the invention provides nanoparticulate nasal compositions comprising one or more acidic pharmaceutically active ingredients. It is considered well within the ordinary skill in the art to determine which of the compounds set for the above are acidic. Such compounds may be prepared as base addition salts, e.g. by the addition of one or more mineral bases (e.g. NaOH, KOH, $NaHCO_3$, $Na_2CO_3$, $NH_3$) or organic bases. It is considered within the skill in the art to choose a pharmaceutically acceptable base.

Known benzodiazepine compounds have anxiolytic, anticonvulsant, sedative and/or skeletal muscle relaxant effect. The term "anticonvulsant" includes treatment of seizures, protection against seizure, reduction or amelioration of the intensity of seizure, reduction or amelioration of the frequency of seizure, and/or prevention of the occurrence or re-occurrence of seizure. In this regard, treatment of seizure includes cessation of an ongoing seizure, reduction in the severity of an ongoing seizure, reduction in the duration of an ongoing seizure. Protection against seizure includes forestalling an oncoming seizure.

The term "seizure" includes commonly recognized types of seizures, including absence seizures, myoclonic seizures, clonic seizures, tonic seizures, tonic-clonic seizures, and atonic seizures. Often seizures, particularly severe tonic or tonic-clonic seizures, will be presaged by one or more aura that will be familiar to the patient or those familiar with the patient. Each patient will generally experience a different type of aura, which is unique to the patient; however auras may be classified as audible, visual, olfactory or tactile sensations that usually, or at least often, precedes a patient's experiencing a seizure. (Not all patients who suffer seizures experience aura; however aura are not uncommon amongst those who suffer the worst type of seizures, especially tonic-clonic seizures.) In some embodiments of the invention, the method includes prompt administration of a nasal preparation of a benzodiazepine drug according to the invention during a period when a patient is experiencing an aura. In some embodiments, such intra-aural administration of benzodiazepine drug by the intra-nasal route will prevent onset of the seizure or may at least ameliorate the effects—e.g. intensity, duration or both—of the seizure. In other embodiments, a patient who has a history of seizure may administer the intranasal drug periodically, and in particular at periodic intervals, to prevent the onset of seizures, to lessen the frequency of seizures, to reduce the severity of seizures, or to provide a combined reduction in severity and frequency of seizures. Thus, in the context of this invention, prevention of seizure refers to a temporary forestalling of the onset of seizure, either with or without the benefit of a warning aura. Treatment of seizure refers to the reduction of seizure intensity, duration or both.

Modes of Administration

Medicaments comprising a pharmaceutical particulate composition having a multimodal particle size distribution can be administered by various modes of delivery, including nasal and pulmonary modes of delivery. In some embodiments, the invention provides methods of using a pharmaceutical particulate composition for nasal delivery of a medicament comprising particulates having a multimodal particle size distribution. In some embodiments, some embodiments, the invention provides methods of using a pharmaceutical particulate composition for pulmonary delivery of a medicament comprising particulates having a multimodal particle size distribution.

Nasal Administration

In some embodiments, there are provided nasal drug dosages. Nasal dosages according to the invention can be administered as a nasal spray or nasal drop, although presently preferred embodiments are nasal sprays. Nasal sprays may be liquid or solid nasal sprays. The nasal sprays may be aerosol or non-aerosol nasal sprays. There are three currently preferred types of nasal delivery system: 1) aerosolized metered dose pumps, 2) manual metered dose pumps, and 3) metered dose spray-producing squeeze bottles. Each of these is effective in providing for the rapid absorption of medicinal compounds into the blood stream. In some embodiments, e.g. in the case of an unconscious patient experiencing a seizure, the aerosolized metered dose pump connected to a close fitting plastic mask covering the nose and mouth (such as is commonly used to administer oxygen) can be an especially effective delivery system. However, in other embodiments, one of the other two methods may be equally effective.

The term aerosol may refer to a suspension or dispersion of either liquid droplets or solid powder in air. In this context, liquid droplets may be formed from solutions, suspensions and dispersions of drug in a liquid medium, such as water or a non-aqueous medium. The liquid medium may also contain one or more diluents, excipients, enhancers or additional active pharmaceutical ingredients. Where the aerosol is a suspension of liquid in air, it is possible, and in some embodiments of the invention preferred, that the liquid contain particles of a drug compound that are insoluble or slightly soluble in the liquid. It is also possible for the drug to be fully soluble in the liquid.

Solid powder includes solid particulates comprising solid drug and optionally one or more non-liquid diluents, excipients, additional solid active ingredients, etc.

An aerosol according to the invention may be insufflated using a suitable mechanical apparatus. In some embodiments, the apparatus may include a reservoir and sprayer, which is a device adapted to expel the pharmaceutical dose in the form of a spray. A number of doses of the drug to be administered may be contained within the reservoir, optionally in a liquid solution or suspension or in a solid particulate formulation, such as a solid particulate mixture.

In some embodiments, the apparatus is a pump sprayer that includes a metering pump. In some embodiments, the apparatus includes a pressurized spray device, in which the sprayer includes a metering valve and the pharmaceutical composition further comprises a pharmaceutically acceptable propellant. Exemplary propellants include one or mixture of chlorofluorocarbons, such as dichlorodifluoromethane, as well as the currently preferred hydrofluorocarbons, such as 1,1,1,2-tetrafluoroethane (HFC-134a) and 1,1,1,2,3,3,3-heptafluoropropane (HFC-227). Suitable pressurized spray devices are well known and will be familiar to those of skill in the art.

In some embodiments, powders can be administered using a nasal insufflator. In some embodiments, powders may be contained within a capsule, which is inserted into an insufflation device. The capsule is punctured by a needle, which makes apertures at the top and bottom of the capsule. Air or other pharmaceutically acceptable propellant is then sent through the needle to blow out powder particles. In some embodiments, pharmaceutically acceptable propellants include ethyl chloride, butane, propane, dichlorodifluoromethane, dichlorotetrafluoroethane, and trichloromonofluoromethane.

Many benzodiazepines, including diazepam, are so slightly soluble in water that a therapeutically effective amount cannot be dissolved in a volume of aqueous solvent that is amenable to nasal insufflation as an aerosol or non-aerosol spray. It is considered that the volume of insufflate that is suitable for nasal administration is in the range of about 25 to about 250 μl per nostril, preferably about 50 to about 150 μl per nostril, and particularly about 50 to about 100 μl per nostril. The solid or liquid particles may be suspended in an air stream by the action of a micronizing pump, a stream of aerosolizing inert gas, etc.

Thus, in some embodiments, the invention provides aerosols comprising aqueous suspensions or dispersions of drug particles in a liquid medium. The aqueous suspension or dispersion of the invention is suspended or dispersed in air to form an aerosol. It is this aerosol that is insufflated or inhaled through the nose. The droplets or particles are deposited on the surface of the nasal mucosa, where the drug particles suspended in the aerosol particles are absorbed across the mucosal epithelium and into the blood stream.

In some embodiments, the invention provides aerosols comprising dry solid particulates, which are suspended or dispersed in air.

Metered-dose spray pumps for aqueous formulations, pMDIs, and DPIs for nasal delivery are available from, for example, Valois of America or Pfeiffer of America.

A propellant driven inhaler (pMDI) releases a metered dose of drug upon each actuation. The medicine is formulated as a suspension or solution of a drug substance in a suitable propellant such as a halogenated hydrocarbon.

Dry powder inhalers (DPIs), which involve deaggregation and aerosolization of dry powders, normally rely upon a burst of inspired air that is drawn through the unit to deliver a drug dosage. Such devices are known in the art.

Pulmonary Administration

Pulmonary drug delivery requires aerosolization of a solid or liquid and delivery of the aerosol to the lungs via the mouth and throat. Particles that have aerodynamic diameters greater than about 5 μm tend to impact surfaces within the oropharyngeal cavity, and to not reach the lung. Though such particles may ultimately be absorbed, ingestion generally results in slower bioabsorption of the medicament than is available through the pulmonary route. It is generally accepted that 5 μm is the cutoff for pulmonary availability. Indeed, the portion of particles in the aerosol that are smaller than 5 μm is referred to as the respirable dose. (The dose actually deposited in the lungs is referred to as the deposited dose). Particles having diameters of about 2 μm to about 5 μm are generally small enough to reach the upper- to mid-pulmonary region (conducting airways), but are too large to reach the alveolae. Particles having diameters of about 0.5 μm to about 2 μm are considered small enough to reach the alveolae. Particles having diameters smaller than about 0.5 microns can also be deposited in the alveolar region by sedimentation, although very small particles may be exhaled.

In some embodiments, the absorption of particles from the upper- and mid-pulmonary region occurs at a different rate than absorption via the alveolae. In some embodiments, the larger particles deposited in the upper regions of the lung take longer to dissolve in mucosal fluid, and thus take longer to cross the pulmonary mucosa and epithelium. Accordingly, in some embodiments of the invention, a bimodal rate of absorption can be obtained by providing a multimodal distribution of particulates, with at least one mode occurring between about 0.5 μm and about 2 μm and at least one mode occurring between about 2 μm and about 5 μm. In some embodiments, the first mode occurs within the range of about 0.7 μm to about 1.7 μm; and the second mode occurs within the range of about 2.2 μm to about 4.0 μm. In such embodiments, it is considered that one population of particles will be absorbed at a faster rate and will produce a first maximum plasma blood concentration $Cmax_1$ at time $Tmax_1$, while the other population of particles will be absorbed more slowly, and will cause a second maximum plasma blood concentration $Cmax_2$ (which may appear in a graph of medicament plasma blood concentration verus time as a second peak or as a "shoulder" on the blood plasma concentration curve) at time $Tmax_2$ ($Tmax_2 > Tmax_1$). It is considered that such a bimodal distribution of particles will preserve the benefits of each population of particles separately—fast onset of action due to rapid attainment of an effective blood plasma concentration of the medicament from the first population of particles and long duration of effect due to later absorption of the second population of particles.

It is also possible to formulate a trimodal pulmonary medicament, wherein one population of particles has a particle size distribution characterized by a mode greater than about 5 μm. As discussed above, such particles will generally impact the oropharyngeal surfaces and be absorbed through the oropharyngeal mucosa or swallowed. It is considered that a trimodal pulmonary medicament having a first population of particles having a particle size distribution mode in the range of about 0.5 μm to about 2 μm, a second population of particles having a particle size distribution mode in the range of about 2 μm to about 5 μm, and a third population of particles having a particle size distribution mode of greater than about 5 μm, will exhibit a first blood plasma concentration maximum ($Cmax_1$) at time $Tmax_1$, a second blood plasma concentration maximum ($Cmax_2$), which may be visualized as a separate peak or as a shoulder on the blood plasma concentration versus time curve, at time $Tmax_2$ ($Tmax_2>Tmax_1$), and a third blood plasma concentration maximum ($Cmax_3$), which may be visualized as a separate peak or may appear as a shoulder on the first or second peak, at time $Tmax_3$ ($Tmax_3>Tmax_2$). In some embodiments, $Cmax_3$ may be attributable to gastrointestinal absorption, oropharyngeal absorption, or a combination of oropharyngeal and gastrointestinal absorption, of the medicament. The amount of medicament in each population of particles can be adjusted through suitable means, as discussed in more detail herein, to ensure that the fastest-absorbed population of particles will provide rapid attainment of an effective blood plasma concentration of the medicament (e.g. within about 1 to about 30 minutes, especially about 1 to about 10 minutes), while the later-absorbed population of particles will continue to provide effective blood plasma concentrations of the medicament over a prolonged period of (e.g. for about 1 to about 30 hr, especially about 2 to about 24 hours, about 4 to about 24 hours, about 4 to about 12 hours or about 4 to about 8 hours.) Where absorption of medicament from one population of particles is characterized by significant first pass effects, a higher relative amount of the population of particles is used in order to compensate for liver metabolism.

In some embodiments, the pulmonary aerosol may be characterized by a bimodal particle size distribution, with a first mode being between about 0.5 μm and about 5 μm and a second mode being above about 5 μm. In some embodiments, the first mode occurs between about 0.5 μm and about 2 μm. In some embodiments, the first mode occurs between about 2 μm and about 5 μm. In some embodiments, the first mode is between about 1.0 μm and about 4.0 μm. It is considered that the first population of particles will be absorbed in the lung and will enter the blood stream at a faster rate than the second population of particles, having a particle size distribution with a mode greater than about 5 μm, which will be absorbed via the oropharyngeal mucosa, the gastrointestinal system, or both. Thus, the first population of particles will produce a first maximum plasma blood concentration $Cmax_1$ at time $Tmax_1$, while the second population of particles will be absorbed more slowly, and will cause a second maximum plasma blood concentration $Cmax_2$ (which may appear in a graph of medicament plasma blood concentration verus time as a second peak or as a "shoulder" on the blood plasma concentration curve) at time $Tmax_2$ ($Tmax_2>Tmax_1$). It is considered that such a bimodal distribution of particles will preserve the benefits of each population of particles separately—fast onset of action due to rapid attainment of an effective blood plasma concentration of the medicament through pulmonary absorption of the first population of particles and long duration of effect due to slower absorption of the second population of particles via oropharyngeal and/or gastrointestinal absorption.

The person skilled in the art will recognize the need to adjust the relative proportion of a population of particles that is absorbed primarily through the gastrointestinal tract when the medicament is subject to so-called first pass effects. First pass effects generally occur when a drug is absorbed from the gastrointestinal tract, and are generally avoided when the drug is absorbed from the mucosa of the nasal cavities, lungs, and/or oropharyngeal cavity. Absorption of a drug from the gastrointestinal (GI) tract leads to first-pass metabolism, as the portal vein carries GI blood directly to the liver, where many drugs are metabolized. Liver metabolism thus lowers the effective oral bioavailability of many drugs—even many drugs that are otherwise well-absorbed from the GI tract. In some embodiments, such first pass effects are avoided by delivering particles to the lung and minimizing the delivery of drug particles to the oropharyngeal mucosa. In other embodiments, especially where a population of particles comprises a medicament that is quickly metabolized by the liver, and where gastrointestinal absorption is contemplated as a desired route for e.g. longer-term absorption of drug, it is essential to compensate for the first pass effects by adjusting upward the relative proportion of the population of particles having an average particle size of greater than about 5 μm. Of course, where long-term absorption can be obtained by pulmonary absorption, e.g. in the mid- to upper-level lung (particle sizes of about 2.0 μm to about 5.0 μm), in some embodiments it will suffice to increase the proportion of particles having particle sizes in the 2.0 μm to 5.0 μm particle size range, thereby enhancing longer term absorption of the medicament from these particles, while minimizing GI absorption, thereby achieving longer term absorption while minimizing the bioavailability-reducing first pass effects.

Particles of medicament may be administered to the lungs as dry powder aerosols or liquid aerosols. Dry powder aerosols are generally administered to the lungs with dry powder inhaler (DPI) inhalation devices. Dry powder inhalers can include breath actuated dry powder inhalers, such as are described in U.S. Pat. No. 7,434,579. Metered-dose inhalers contain medicament suspended in a propellant, a mixture of propellants, or a mixture of solvents, propellants, and/or other excipients in compact pressurized aerosol dispensers. An MDI product may discharge up to several hundred metered doses of medicament. Each actuation may contain from a few micrograms (mcg) up to milligrams (mg) of the active ingredients delivered in a volume typically between 25 and 100 microliters. In some embodiments, an MDI will contain suitable proportions of a first population of particles, a second population of particles and optionally a third population of particles, each population of particles having a distinct particle size mode.

Another type of liquid aerosol dispersion device is nebulizer, which uses a jet, a vibrating mesh or other means to aerolsolize a suspension containing particles of medicament. In some embodiments, a nebulizer is used to prepare an aerosol containing suitable proportions of a first population of particles, a second population of particles and optionally a third population of particles, each population of particles having a distinct particle size mode.

Preparation of Benzodiazepine Particulate Compositions

Processes for preparing the particles used in the present invention can be accomplished through numerous techniques known to those skilled in the art. A representative, but non-exhaustive, discussion of techniques for preparing particle dispersions of pharmaceutical compositions follows.

In some embodiments, the preparation of small particle dispersions employs energy addition techniques, including adding pharmaceutically active compound to a suitable vehicle, such as water or aqueous solution containing one or more of the surfactants set forth herein, or other pharmaceutically acceptable liquid in which the pharmaceutical compound is relatively insoluble, to form a first suspension. Energy is added to the first suspension to form a particle dispersion, which is physically more stable than the first suspension. Energy is added by mechanical grinding (e.g., pearl milling, ball milling, hammer milling, fluid energy milling, jet milling, or wet grinding). Some suitable methods are described in U.S. Pat. No. 5,145,684, which is incorporated herein by reference.

In some embodiments, such methods further include subjecting the first suspension to high shear conditions, including cavitation, shearing or impact forces utilizing a microfluidizer. In some embodiments, the methods include adding energy to the first suspension using a piston gap homogenizer or counter current flow homogenizer such as those disclosed in U.S. Pat. No. 5,091,188, which is incorporated herein by reference. Suitable piston gap homogenizers are commercially available under the product name EMULSIFLEX by Avestin, and French Pressure Cells sold by Spectronic Instruments. Suitable microfluidizers are available from Microfluidics Corp.

In some embodiments, addition of energy can also be accomplished using sonication techniques. The step of sonicating can be carried out with any suitable sonication device such as the Branson Model S-450A or Cole-Parmer 500/750 Watt Model. Such devices are well known in the industry. In some embodiments, the sonication device may have a sonication horn or probe that is inserted into the first suspension to emit sonic energy into the solution. The sonicating device, in a preferred form of the invention, is operated at a frequency of from about 1 kHz to about 90 kHz and more preferably from about 20 kHz to about 40 kHz or any range or combination of ranges therein. The probe sizes can vary and preferably is in distinct sizes such as ½ inch or ¼ inch or the like.

In some preferred embodiments, the dispersion of small particles will be sterilized prior to use. Sterilization can be accomplished by heat sterilization, gamma irradiation, filtration (either directly as a dispersion having particle sizes under 200 nm, or by sterile filtration of the solutions used in the precipitation process, prior to forming the solid dispersion), and by application of very high pressure (greater than 2000 atmospheres), or by a combination of high pressure and elevated temperature.

Small particle dispersions can also be prepared by precipitation techniques. In some embodiments, the small particle dispersions are formed by a microprecipitation method, which includes: (i) dissolving the organic compound in a water-miscible first solvent; (ii) preparing a solution of polymer and an amphiphile in an aqueous second solvent and in which second solvent the organic compound is substantially insoluble whereby a polymer/amphiphile complex is formed; and (iii) mixing the solutions from steps (i) and (ii) so as to cause precipitation of an aggregate of the organic compound and the polymer/amphiphile complex.

In some embodiments, the precipitation process is one described in U.S. Pat. No. 6,607,784 and co-pending and commonly assigned U.S. Ser. Nos. 09/874,499; 09/874,637; 10/021,692, which are incorporated herein by reference. In some embodiments, such methods comprise: (1) dissolving an organic compound in a water miscible first organic solvent to create a first solution; (2) mixing the first solution with a second solvent or water to precipitate the organic compound to create a first suspension; and (3) adding energy to the first suspension in the form of high-shear mixing or heat to provide a dispersion of small particles. In some embodiments, the first organic solvent is removed from the mixture by any suitable means such as centrifugation or filtration methods. In some embodiments, the continuous phase of the dispersion can be optionally replaced by another continuous phase by removing the first continuous phase using methods such as centrifugation and filtration, adding a second continuous phase and subsequently re-dispersing the solid material in the second continuous phase. One or more optional surface modifiers set forth herein can be added to the first organic solvent or the second aqueous solution.

In some embodiments, particulates according to the invention are formed by an emulsion precipitation technique, including: (1) providing a multiphase system having an organic phase and an aqueous phase, the organic phase having a pharmaceutically active compound therein; and (2) sonicating the system to evaporate a portion of the organic phase to cause precipitation of the compound in the aqueous phase to form a dispersion of small particles. The step of providing a multiphase system includes the steps of: (1) mixing a water immiscible solvent with the pharmaceutically active compound to define an organic solution, (2) preparing an aqueous based solution with one or more surface active compounds, and (3) mixing the organic solution with the aqueous solution to form the multiphase system. The step of mixing the organic phase and the aqueous phase can include the use of piston gap homogenizers, colloidal mills, high speed stirring equipment, extrusion equipment, manual agitation or shaking equipment, microfluidizer, or other equipment or techniques for providing high shear conditions. The crude emulsion will have oil droplets in the water of a size of approximately less than 1 μm in diameter. The crude emulsion is sonicated to define a microemulsion and eventually to provide a dispersion of small particles.

In some embodiments, a dispersion of small particles may include: (1) providing a crude dispersion of a multiphase system having an organic phase and an aqueous phase, the organic phase having a pharmaceutical compound therein; (2) providing energy to the crude dispersion to form a fine dispersion; (3) freezing the fine dispersion; and (4) lyophilizing the fine dispersion to obtain small particles of the pharmaceutical compound. The small particles can be sterilized by the techniques set forth herein or the small particles can be reconstituted in an aqueous medium and sterilized.

In some embodiments, a multiphase system is provided by: (1) mixing a water immiscible solvent with the pharmaceutically effective compound to define an organic solution; (2) preparing an aqueous based solution with one or more surface active compounds; and (3) mixing the organic solution with the aqueous solution to form the multiphase system. The step of mixing the organic phase and the aqueous phase may include the use of piston gap homogenizers, colloidal mills, high speed stirring equipment, extrusion equipment, manual agitation or shaking equipment, microfluidizer, or other equipment or techniques for providing high shear conditions.

In some embodiments, small particle dispersions can be prepared using solvent anti-solvent precipitation as described in U.S. Pat. No. 5,118,528 and U.S. Pat. No. 5,100,591, each of which is incorporated herein by reference. In some embodiments, the process includes: (1) preparing a liquid phase of a biologically active substance in a solvent or a mixture of solvents to which may be added one or more surfactants; (2) preparing a second liquid phase of a non-solvent or a mixture of non-solvents, the non-solvent is miscible with the solvent or mixture of solvents for the substance; (3) adding together the solutions of (1) and (2) with stirring; and (4) removing of unwanted solvents to produce a dispersion of small particles. These methods are distinguished from those described under the above section, "Microprecipitation Methods", in that they do not provide for a last step of adding energy to the suspension in the form of high-shear mixing or heat.

In some embodiments, small particle dispersions can be formed using phase inversion precipitation as disclosed in U.S. Pat. No. 6,235,224, 6,143,211 and U.S. Pre-Grant Publication No. 2001/0042932, each of which is incorporated herein by reference. Phase inversion is a term used to describe the physical phenomena by which a polymer dissolved in a continuous phase solvent system inverts into a solid macromolecular network in which the polymer is the continuous phase. One method to induce phase inversion is by the addition of a non-solvent to the continuous phase. The polymer undergoes a transition from a single phase to an unstable two phase mixture: polymer rich and polymer poor fractions. Micellar droplets of non-solvent in the polymer rich phase serve as nucleation sites and become coated with polymer. The '224 patent discloses that phase inversion of polymer solutions under certain conditions can bring about spontaneous formation of discrete microparticles, including nanoparticles. The '224 patent discloses dissolving or dispersing a polymer in a solvent. A pharmaceutical agent is also dissolved or dispersed in the solvent. For the crystal seeding step to be effective in this process it is desirable the agent is dissolved in the solvent. The polymer, the agent and the solvent together form a mixture having a continuous phase, wherein the solvent is the continuous phase. The mixture is then introduced into at least tenfold excess of a miscible non-solvent to cause the spontaneous formation of the microencapsulated microparticles of the agent having an average particle size of between 10 nm and 10 μm. The particle size is influenced by the solvent: non-solvent volume ratio, polymer concentration, the viscosity of the polymer-solvent solution, the molecular weight of the polymer, and the characteristics of the solvent-non-solvent pair.

In some embodiments, small particle dispersions can be formed by pH shift precipitation techniques. In some embodiments, such processes include dissolving a drug in a solution having a pH in which the drug is soluble, followed by changing the pH to a point where the drug is no-longer soluble. The pH can be acidic or basic, depending on the particular pharmaceutical compound. The solution may then be neutralized to form a dispersion of small particles. One suitable pH shifting precipitation process is disclosed in U.S. Pat. No. 5,665,331, which is incorporated herein by reference. The process includes the step of dissolving of the pharmaceutical agent together with a crystal growth modifier (CGM) in an alkaline solution and then neutralizing the solution with an acid in the presence of suitable surface-modifying surface-active agent or agents to form a small particle dispersion of the pharmaceutical agent. The precipitation step can be followed by steps of diafiltration clean-up of the dispersion and then adjusting the concentration of the dispersion to a desired level.

Other examples of pH shifting precipitation methods are disclosed in U.S. Pat. Nos. 5,716,642; 5,662,883; 5,560,932; and 4,608,278, which are incorporated herein by reference and are made a part hereof.

In some embodiments, infusion precipitation techniques are used to form small particle dispersions as described in U.S. Pat. Nos. 4,997,454 and 4,826,689, which are incorporated herein by reference. First, a suitable solid compound is dissolved in a suitable organic solvent to form a solvent mixture. Then, a precipitating non-solvent miscible with the organic solvent is infused into the solvent mixture at a temperature between about −10° C. and about 100° C. and at an infusion rate of from about 0.01 ml per minute to about 1000 ml per minute per volume of 50 ml to produce a suspension of precipitated non-aggregated solid particles of the compound with a substantially uniform mean diameter of less than 10 μm. Agitation (e.g., by stirring) of the solution being infused with the precipitating non-solvent is preferred. The non-solvent may contain a surfactant to stabilize the particles against aggregation. The particles are then separated from the solvent. Depending on the solid compound and the desired particle size, the parameters of temperature, ratio of non-solvent to solvent, infusion rate, stir rate, and volume can be varied according to the invention. The particle size is proportional to the ratio of non-solvent: solvent volumes and the temperature of infusion and is inversely proportional to the infusion rate and the stirring rate. The precipitating non-solvent may be aqueous or non-aqueous, depending upon the relative solubility of the compound and the desired suspending vehicle.

In some embodiments, temperature shift precipitation techniques may also be used to form small particle dispersions. This technique is disclosed in U.S. Pat. No. 5,188,837, which is incorporated herein by reference. In some embodiments, lipospheres are prepared by the steps of: (1) melting or dissolving a substance such as a drug to be delivered in a molten vehicle to form a liquid of the substance to be delivered; (2) adding a phospholipid along with an aqueous medium to the melted substance or vehicle at a temperature higher than the melting temperature of the substance or vehicle; (3) mixing the suspension at a temperature above the melting temperature of the vehicle until a homogenous fine preparation is obtained; and then (4) rapidly cooling the preparation to room temperature or below.

In some embodiments, the invention makes use of solvent evaporation precipitation techniques, as described in U.S. Pat. No. 4,973,465, which is incorporated herein by reference. In some embodiments, microcrystals are prepared by: (1) providing a solution of a pharmaceutical composition and a phospholipid dissolved in a common organic solvent or combination of solvents; (2) evaporating the solvent or solvents; and (3) suspending the film obtained by evaporation of the solvent or solvents in an aqueous solution by vigorous stirring to form a dispersion of small particles. The solvent can be removed by evaporating a sufficient quantity of the solvent to cause precipitation of the compound. The solvent can also be removed by other well known techniques such as applying a vacuum to the solution or blowing nitrogen over the solution.

In some embodiments, reaction precipitation is employed. In some embodiments, reaction precipitation includes dissolving the pharmaceutical compound, and optionally other excipients, into a suitable solvent to form a solution. The compound may be added in an amount at or below the saturation point of the compound in the solvent. The compound or any of the excipients is precipitated from solution by reacting with a chemical agent or by modification in response to adding energy such as heat or UV light or the like such that the modified compound has a lower solubility in the solvent and precipitates from the solution to form a small particle dispersion. Precipitation of excipient provides a solid matrix into which the drug is sorbed.

In some embodiments, a suitable technique for precipitating is by compressed fluid precipitation. In some embodiments, a suitable method is described in WO 97/14407, which is incorporated herein by reference. The method includes the steps of dissolving a water-insoluble drug in a solvent to form a solution. The solution is then sprayed into a compressed fluid, which can be a gas, liquid or supercritical fluid. The addition of the compressed fluid to a solution of a solute in a solvent causes the solute to attain or approach supersaturated state and to precipitate out as fine particles. The compressed fluid acts as an anti-solvent which lowers the cohesive energy density of the solvent in which the drug is dissolved. In some embodiments, the drug can be dissolved in the compressed fluid which is then sprayed into an aqueous phase. The rapid expansion of the compressed fluid reduces the solvent power of the fluid, which in turn causes the solute to precipitate out as small particles in the aqueous phase. In this case, the compressed fluid acts as a solvent. In order to stabilize the particles against aggregation, a surface modifier, such as a surfactant, may be employed within certain embodiments of the invention. In some embodiments, a suitable technique for precipitating by compressed fluid is one wherein the active ingredient is mixed with water, one or more solvents, or a combination thereof, and the resulting mixture sprayed at or below the surface of a cryogenic fluid. Frozen particles are thereby provided. Materials for encapsulating the solid particles may also be added so that frozen particles are generated wherein the encapsulating agent surrounds the active agent.

In some embodiments, methods according to the invention include protein microsphere precipitation. Microspheres or microparticles utilized in this invention can also be produced from a process involving mixing or dissolving macromolecules such as proteins with a water soluble polymer. In some embodiments, a suitable method is disclosed in U.S. Pat. Nos. 5,849,884, 5,981,719, 6,090,925, 6,268,053, 6,458,387, which are incorporated herein by reference. In some embodiments, microspheres may be prepared by mixing a macromolecule in solution with a polymer or a mixture of polymers in solution at a pH near the isoelectric point of the macromolecule. The mixture is incubated in the presence of an energy source, such as heat, radiation, or ionization, for a predetermined amount of time. The resulting microspheres can be removed from any unincorporated components present in the solution by physical separation methods.

In some embodiments, other processes for preparing particles of pharmaceutical compositions (i.e. organic compound) used in the present invention can be separated into four general categories. Each of the categories of processes share the steps of: (1) dissolving an organic compound in a water miscible first solvent to create a first solution, (2) mixing the first solution with a second solvent of water to precipitate the organic compound to create a pre-suspension, and (3) adding energy to the first suspension in the form of high-shear mixing or heat, or a combination of both, to provide a stable form of the organic compound having the desired size ranges defined above. The mixing steps and the energy adding step can be carried out in consecutive steps or simultaneously.

Some categories of processes are distinguished based upon the physical properties of the organic compound as determined through x-ray diffraction studies, differential scanning calorimetry (DSC) studies, or other suitable study conducted prior to the energy-addition step and after the energy-addition step. In the first process category, prior to the energy-addition step the organic compound in the first suspension takes an amorphous form, a semi-crystalline form or a supercooled liquid form and has an average effective particle size. After the energy-addition step the organic compound is in a crystalline form having an average effective particle size essentially the same or less than that of the first suspension.

In another process category, prior to the energy-addition step the organic compound is in a crystalline form and has an average effective particle size. After the energy-addition step the organic compound is in a crystalline form having essentially the same average effective particle size as prior to the energy-addition step but the crystals after the energy-addition step are less likely to aggregate or form large crystals. The reduced tendency of the organic compound to aggregate or form large crystals is observed by laser dynamic light scattering and light microscopy.

In another process category, prior to the energy-addition step, the organic compound is in a crystalline form that is friable and has an average effective particle size. After the energy-addition step the organic compound is in a crystalline form having an average effective particle size smaller than the crystals of the pre-suspension. By taking the steps necessary to place the organic compound in a crystalline form that is friable, the subsequent energy-addition step can be carried out more quickly and efficiently when compared to an organic compound in a less friable crystalline morphology.

In another process category, the first solution and second solvent are simultaneously subjected to the energy-addition step. Thus, the physical properties of the organic compound before and after the energy addition step were not measured. The energy-addition step can be carried out in any fashion wherein the first suspension or the first solution and second solvent are exposed to cavitation, shearing or impact forces. In some embodiments, the energy-addition step is an annealing step. Annealing is defined in this invention as the process of converting matter that is thermodynamically unstable into a more stable form by single or repeated application of energy (direct heat or mechanical stress), followed by thermal relaxation. This lowering of energy may be achieved by conversion of the solid form from a less ordered to a more ordered lattice structure. Alternatively, this stabilization may occur by a reordering of the surfactant molecules at the solid-liquid interface.

It should be understood that the process conditions such as choice of surfactants or combination of surfactants, amount of surfactant used, temperature of reaction, rate of mixing of solutions, rate of precipitation and the like can be selected to allow for any drug to be processed under any one of the categories discussed in the following paragraphs.

The foregoing process categories, can be further divided into two subcategories: Methods A and B.

In some embodiments, the first solvent according to the following processes is a solvent or mixture of solvents in which the organic compound of interest is relatively soluble and which is miscible with the second solvent. Such solvents include, but are not limited to water-miscible protic compounds, in which a hydrogen atom in the molecule is bound to an electronegative atom such as oxygen, nitrogen, or other Group VA, VIA and VII A in the Periodic Table of elements. Examples of such solvents include, but are not limited to, alcohols, amines (primary or secondary), oximes, hydroxamic acids, carboxylic acids, sulfonic acids, phosphonic acids, phosphoric acids, amides and ureas.

Other examples of the first solvent also include aprotic organic solvents. Some of these aprotic solvents can form hydrogen bonds with water, but can only act as proton acceptors because they lack effective proton donating groups. One class of aprotic solvents is a dipolar aprotic solvent, as defined by the International Union of Pure and Applied Chemistry (IUPAC Compendium of Chemical Terminology, 2nd Ed., 1997): [0071] A solvent with a comparatively high relative permittivity (or dielectric constant), greater than ca. 15, and a sizable permanent dipole moment, that cannot donate suitably labile hydrogen atoms to form strong hydrogen bonds, e.g. dimethyl sulfoxide.

In some embodiments, dipolar aprotic solvents can be selected from the group consisting of: amides (fully substituted, with nitrogen lacking attached hydrogen atoms), ureas (fully substituted, with no hydrogen atoms attached to nitrogen), ethers, cyclic ethers, nitriles, ketones, sulfones, sulfoxides, fully substituted phosphates, phosphonate esters, phosphoramides, nitro compounds, and the like. Dimethylsulfoxide (DMSO), N-methyl-2-pyrrolidinone (NMP), 2-pyrrolidinone, 1,3-dimethylimidazolidinone (DMI), dimethylacetamide (DMA), dimethylformamide (DMF), dioxane, acetone, tetrahydrofuran (THF), tetramethylenesulfone (sulfolane), acetonitrile, and hexamethylphosphoramide (HMPA), nitromethane, among others, are members of this class.

In some embodiments, solvents may also be chosen that are generally water-immiscible, but have sufficient water solubility at low volumes (less than 10%) to act as a water-miscible first solvent at these reduced volumes. Examples include aromatic hydrocarbons, alkenes, alkanes, and halogenated aromatics, halogenated alkenes and halogenated alkanes. Aromatics include, but are not limited to, benzene (substituted or unsubstituted), and monocyclic or polycyclic arenes. Examples of substituted benzenes include, but are not limited to, xylenes (ortho, meta, or para), and toluene. Examples of alkanes include but are not limited to hexane, neopentane, heptane, isooctane, and cyclohexane. Examples of halogenated aromatics include, but are not restricted to, chlorobenzene, bromobenzene, and chlorotoluene. Examples of halogenated alkanes and alkenes include, but are not restricted to, trichloroethane, methylene chloride, ethylenedichloride (EDC), and the like.

In some embodiments, solvent classes include but are not limited to: N-methyl-2-pyrrolidinone (also called N-methyl-2-pyrrolidone), 2-pyrrolidinone (also called 2-pyrrolidone), 1,3-dimethyl-2-imidazolidinone (DMI), dimethylsulfoxide, dimethylacetamide, acetic acid, lactic acid, methanol, ethanol, isopropanol, 3-pentanol, n-propanol, benzyl alcohol, glycerol, butylene glycol (butanediol), ethylene glycol, propylene glycol, mono- and diacylated monoglycerides (such as glyceryl caprylate), dimethyl isosorbide, acetone, dimethylsulfone, dimethylformamide, 1,4-dioxane, tetramethylenesulfone (sulfolane), acetonitrile, nitromethane, tetramethylurea, hexamethylphosphoramide (HMPA), tetrahydrofuran (THF), dioxane, diethylether, tert-butylmethyl ether (TBME), aromatic hydrocarbons, alkenes, alkanes, halogenated aromatics, halogenated alkenes, halogenated alkanes, xylene, toluene, benzene, substituted benzene, ethyl acetate, methyl acetate, butyl acetate, chlorobenzene, bromobenzene, chlorotoluene, trichloroethane, methylene chloride, ethylenedichloride (EDC), hexane, neopentane, heptane, isooctane, cyclohexane, polyethylene glycol (PEG, for example, PEG-4, PEG-8, PEG-9, PEG-12, PEG-14, PEG-16, PEG-120, PEG-75, PEG-150), polyethylene glycol esters (examples such as PEG-4 dilaurate, PEG-20 dilaurate, PEG-6 isostearate, PEG-8 palmitostearate, PEG-150 palmitostearate), polyethylene glycol sorbitans (such as PEG-20 sorbitan isostearate), polyethylene glycol monoalkyl ethers (examples such as PEG-3 dimethyl ether, PEG-4 dimethyl ether), polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate, and glycofurol (tetrahydrofurfuryl alcohol polyethylene glycol ether). A preferred first solvent is N-methyl-2-pyrrolidinone. In some embodiments, another preferred first solvent is lactic acid.

In some embodiments, the second solvent is an aqueous solvent. This aqueous solvent may be water by itself. This solvent may also contain buffers, salts, surfactant(s), water-soluble polymers, and combinations of these excipients.

In Method A, the organic compound ("drug") is first dissolved in the first solvent to create a first solution. The organic compound can be added from about 0.1% (w/v) to about 50% (w/v) depending on the solubility of the organic compound in the first solvent. Heating of the concentrate from about 30° C. to about 100° C. may be necessary to ensure total dissolution of the compound in the first solvent.

A second aqueous solvent is provided with one or more optional surface modifiers such as an anionic surfactant, a cationic surfactant, a zwitterionic surfactant, a nonionic surfactant or a biologically surface active molecule added thereto. Suitable anionic surfactants include but are not limited to alkyl sulfonates, alkyl phosphates, alkyl phosphonates, potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inosine, phosphatidylinositol, diphosphatidylglycerol, phosphatidylserine, phosphatidic acid and their salts, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.).

Zwitterionic surfactants are electrically neutral but possess local positive and negative charges within the same molecule. Suitable zwitterionic surfactants include but are not limited to zwitterionic phospholipids. Suitable phospholipids include phosphatidylcholine, phosphatidylethanolamine, diacyl-glycero-phosphoethanolamine (such as dimyristoyl-glycero-phosphoethanolamine (DMPE), dipalmitoyl-glycero-phosphoethanolamine (DPPE), distearoyl-glycero-phosphoethanolamine (DSPE), and dioleolyl-glycero-phosphoethanolamine (DOPE)). Mixtures of phospholipids that include anionic and zwitterionic phospholipids may be employed in this invention. Such mixtures include but are not limited to lysophospholipids, egg or soybean phospholipid or any combination thereof. The phospholipid, whether anionic, zwitterionic or a mixture of phospholipids, may be salted or desalted, hydrogenated or partially hydrogenated or natural semi-synthetic or synthetic. The phospholipid may also be conjugated with a water-soluble or hydrophilic polymer to specifically target the delivery to macrophages in the present invention. However, conjugated phospholipids may be used to target other cells or tissue in other applications. A preferred polymer is polyethylene glycol (PEG), which is also known as the monomethoxy polyethyleneglycol (mPEG). The molecule weights of the PEG can vary, for example, from 200 to 50,000. Some commonly used PEG's that are commercially available include PEG 350, PEG 550, PEG 750, PEG 1000, PEG 2000, PEG 3000, and PEG 5000. The phospholipid or the PEG-phospholipid conjugate may also incorporate a functional group which can covalently attach to a ligand including but not limited to proteins, peptides, carbohydrates, glycoproteins, antibodies, or pharmaceutically active agents. These functional groups may conjugate with the ligands through, for example, amide bond formation, disulfide or thioether formation, or biotin/streptavidin binding. Examples of the ligand-binding functional groups include but are not limited to hexanoylamine, dodecanylamine, 1,12-dodecanedicarboxylate, thioethanol, 4-(p-maleimidophenyl)butyramide (MPB), 4-(p-maleimidomethyl)cyclohexane-carboxamide (MCC), 3-(2-pyridyldithio)propionate (PDP), succinate, glutarate, dodecanoate, and biotin.

In some embodiments, suitable cationic surfactants may include, but are not limited to, natural phospholipids, synthetic phospholipids, quaternary ammonium compounds, benzalkonium chloride, cetyltrimethylammonium bromide, chitosans, lauryldimethylbenzylammonium chloride, acyl carnitine hydrochlorides, dimethyldioctadecylammomium bromide (DDAB), dioleyoltrimethylammonium propane (DOTAP), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, or long-chain alkyl amines such as, for example, n-octylamine and oleylamine.

In some embodiments, suitable nonionic surfactants include: glyceryl esters, polyoxyethylene fatty alcohol ethers (Macrogol and Brij), polyoxyethylene sorbitan fatty acid esters (Polysorbates), polyoxyethylene fatty acid esters (Myrj), sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxamers), poloxamines, methylcellulose, hydroxymethylcellulose, hydroxypropylcellulose, hydroxypropylmethylcellulose, noncrystalline cellulose, polysaccharides including starch and starch derivatives such as hydroxyethylstarch (HES), polyvinyl alcohol, and polyvinylpyrrolidone. In a preferred form, the nonionic surfactant is a polyoxyethylene and polyoxypropylene copolymer and preferably a block copolymer of propylene glycol and ethylene glycol. Such polymers are sold under the tradename POLOXAMER also sometimes referred to as PLURONIC®, and sold by several suppliers including Spectrum Chemical and Ruger. Among polyoxyethylene fatty acid esters is included those having short alkyl chains. One example of such a surfactant is SOLUTOL® HS 15, polyethylene-660-hydroxystearate, manufactured by BASF Aktiengesellschaft. Surface-active biological molecules include such molecules as albumin, casein, hirudin or other appropriate proteins. Polysaccharide biologics are also included, and consist of but are not limited to, starches, heparins, and chitosans. Other suitable surfactants include any amino acids such as leucine, alanine, valine, isoleucine, lysine, aspartic acid, glutamic acid, methionine, phenylalanine, or any derivatives of these amino acids such as, for example, amide or ester derivatives and polypeptides formed from these amino acids.

In some embodiments, it may also be desirable to add a pH adjusting agent to the second solvent. Suitable pH adjusting agents include, but are not limited to, hydrochloric acid, sulfuric acid, phosphoric acid, monocarboxylic acids (such as, for example, acetic acid and lactic acid), dicarboxylic acids (such as, for example, succinic acid), tricarboxylic acids (such as, for example, citric acid), THAM (tris(hydroxymethyl)aminomethane), meglumine (N-methylglucosamine), sodium hydroxide, and amino acids such as glycine, arginine, lysine, alanine, histidine and leucine. The second solvent should have a pH within the range of from about 3 to about 11. The aqueous medium may additionally include an osmotic pressure adjusting agent, such as but not limited to glycerin, a monosaccharide such as dextrose, a disaccharide such as sucrose, a trisaccharide such as raffinose, and sugar alcohols such as mannitol, xylitol and sorbitol.

Method B differs from Method A in the following respects: The first difference is a surfactant or combination of surfactants is added to the first solution. The surfactants may be selected from the groups of anionic, nonionic, cationic surfactants, and surface-active biological modifiers set forth above.

U.S. Pat. No. 5,780,062 discloses a process for preparing small particles of an organic compound by first dissolving the compound in a suitable water-miscible first solvent. A second solution is prepared by dissolving a polymer and an amphiphile in aqueous solvent. The first solution is then added to the second solution to form a precipitate that consists of the organic compound and a polymer-amphiphile complex. The '062 patent does not disclose utilizing the energy-addition step of this process in Methods A and B. Lack of stability is typically evidenced by rapid aggregation and particle growth. In some instances, amorphous particles recrystallize as large crystals. Adding energy to the pre-suspension in the manner disclosed above typically affords particles that show decreased rates of particle aggregation and growth, as well as the absence of recrystallization upon product storage.

In some embodiments, the invention provides multimodal (polymodal) mixtures of particulates for nasal administration. In some embodiments, such a multimodal mixture is a bimodal mixture in a suitable carrier, such as an aqueous carrier or a non-aqueous carrier (e.g. a non-aqueous propellant) as described herein. In general, a multimodal mixture comprises two or more populations of particles having distinct mean particle diameters. In addition to differing in mean particle size, the two or more populations of particles may differ in terms of the active pharmaceutical ingredient or ingredients in each, the presence or absence of one or more surface active agents (surfactants) on one or other of the populations of particles, etc. In some embodiments, the two or more populations of particles are formed separately and then mixed together, optionally in the presence of a suitable carrier, in appropriate proportions. In some embodiments, the multimodal mixture is a bimodal mixture comprising about 1 to 50% of a first population of particles and about 50 to about 99% of the second population of particles, wherein the percentages refer to the percent by weight of the one population of particles in relation to the total weight of all particles prior to mixing the two populations of particles together. In some embodiments, the multimodal mixture comprises about 2 to about 48% of the first population of particles and about 52 to about 98% of the second population of particles. In some particular embodiments, the multimodal mixture comprises about 5 to about 45% of the first population of particles and about 55 to about 95% of the second population of particles.

A mixture of two or more different sized particles results in modified pharmacokinetic properties as compared to a monomodal composition, as the smaller sized particles generally are absorbed across the nasal mucosal at a more rapid rate, while the larger sized particles tend to be absorbed more slowly. Thus, mixture comprising two or more populations of particles will tend to exhibit a plasma concentration curve for the active pharmaceutical ingredient having a shape characteristic of modified release: either a multimodal plasma concentration curve, a plasma concentration curve having a single mode (local maximum concentration on the concentration curve) and one or more shoulders (leading, trailing or both) or a single mode and a more pronounced tail. In comparison to a composition comprising a population of particles having as single particle diameter mode, a multimodal composition may have a lower peak concentration (Cmax). In some embodiments, the time required to reach Cmax (Tmax) may be prolonged, as Cmax may not be achieved until after the second population of particles begins to contribute significantly to the plasma concentration. In some embodiments, a first Cmax (Cmax1) may be obtained in a relatively short period of time (Tmax1), and a second, distinct Cmax (Cmax2), may be obtained at a later time (Tmax2). Such distinctly bimodal release curves may have the benefit of providing a first "burst" of activity (especially anticonvulsant activity), and a later, more gradual release of active pharmaceutical ingredient for maintenance purposes (e.g. prevention of relapse into convulsion after the "burst" has begun to dissipate.) Thus, in some embodiments, the invention provides a first bolus of active ingredient, e.g. for the purposes of terminating or palliating the effects of a convulsion, and a longer period during which an effective concentration of the active pharmaceutical ingredient remains in the plasma. In some embodiments, the concentration of active pharmaceutical ingredient provided by the initial bolus is sufficient to terminate a convulsion or reduce the duration, severity or both of the convulsion. In some embodiments, the effective concentration present in the plasma after the initial bolus is a prophylactic dose of the active pharmaceutical ingredient. It is to be understood that prophylaxis is intended to mean reduction in the likelihood that another convulsion will occur, or if one does occur, that it will be of shorter duration, lesser severity or both, than if the patient were not treated.

In some embodiments, the invention provides extended release of active pharmaceutical ingredient as compared to a monomodal composition, especially one comprising only smaller diameter particles (e.g. less than about 1000 nm).

In some embodiments, two or more active pharmaceutical ingredients may be combined in a single formulation. In some embodiments, the first population of particles may comprise a first active pharmaceutical ingredient and the second population of particles a second active pharmaceutical ingredient. In some embodiments, the first population of particles may comprise a first active pharmaceutical ingredient and a second active pharmaceutical ingredient, and the second population of particles may comprise a second active pharmaceutical ingredient, and optionally either the first active pharmaceutical ingredient, a third active pharmaceutical ingredient or a combination thereof. In such cases, it is considered that at least two distinct plasma concentration curves will be obtained—one for the first active pharmaceutical ingredient, one for the second active pharmaceutical ingredient and optionally (where present), a third active pharmaceutical ingredient. It is furthermore considered that each distinct plasma concentration curve, considered by itself, may appear to be a normal monomodal plasma concentration curve. (Such would especially be the case in a bimodal mixture in which the first population of particles contained a first active pharmaceutical ingredient only and the second population of particles contained a second active pharmaceutical ingredient only.) However, in such cases, it is considered that overlaying the two or more concentration curves (or summing them) would produce one of the characteristic curves above—i.e. pure bimodal, monomodal with a shoulder or monomodal with a pronounced tail. It is also considered that one or more of the plasma concentration curves may itself be of one of the characteristic shapes for a multimodal mixture of particles. (Such may be the case in a bimodal mixture in which both of the populations of particles comprises a the same active pharmaceutical ingredient.) It is considered that overlaying the two or more concentration curves (or summing them) would produce one of the characteristic curves above—i.e. pure bimodal, monomodal with a shoulder or monomodal with a pronounced tail.

The two or more populations of particles may also differ from each other regarding coatings applied to the particles. In some embodiments, one population of particles may be uncoated and one or more additional populations may be coated with one or more coatings comprising enhancers, surface active agents, or both. In some embodiments, one population of particles may be coated with one type of coating and one or more additional populations of particles may be coated with a different type of coating. In some embodiments, for example, a small population of particles (e.g. about 25 to about 500 nm in diameter) may be coated uncoated, while a second, larger population of particles (e.g. about 1000 to about 10,000 nm) may be coated with an enhancer, a surface active agent that aids in adherence of the particles to the mucosa, or both. In some embodiments, the smaller population of particles (e.g. about 25 to about 500 nm in diameter) may be coated with a thin layer of enhancer and the second, larger population of particles (e.g. about 1000 to about 10,000 nm) may be coated with a layer of enhancer overlayed with a layer of surface active agent or with a layer of enhancer combined with surface active agent. The person skilled in the art will recognize that other combinations are possible. For example, in some embodiments both smaller (e.g. about 25 to 500 nm diameter) particles and larger (e.g. about 1000 to about 10,000 nm) particles may be coated with enhancer, surface active agent or both.

EXAMPLES

The invention will now be illustrated with reference to the following illustrative, non-limiting examples.

Example 1

Compositions comprising diazepam, lorazepam and/or midazolam (or pharmaceutically acceptable salts thereof) are prepared. The compositions are bimodal, comprising a first population of particles having a mean particle diameter of about 100 nm to about 300 nm and a second population of particles having a mean particle diameter of about 2500 to about 3500 nm (about 2.5 to about 3.5 μm). The first population of particles is prepared as described herein. The second population is then prepared as described herein. The two populations of particles are then combined in the weight proportions indicated in the Table below, mixed with a suitable delivery vehicle and dispensed into a suitable container for nasal installation. Compositions according this example are set forth in the following table.

TABLE

| Pop. 1 Active Pharmaceutical Ingredient | Pop. 1 Mean Particle Diameter (nm) | Pop. 1 Percent weight of total particles | Pop. 2 Active Pharmaceutical Ingredient | Pop. 2 Mean Particle Diameter (μm) | Pop. 2 Percent weight of total particles | Carrier |
|---|---|---|---|---|---|---|
| Diazepam | 100 nm | 50 | Diazepam | 2.5 | 50 | Saline |
| Diazepam | 100 nm | 45 | Diazepam | 2.5 | 55 | Saline |
| Lorazepam | 100 nm | 50 | Lorazepam | 2.5 | 50 | Saline |
| Lorazepam | 100 nm | 45 | Lorazepam | 2.5 | 55 | Saline |
| Midazolam | 100 nm | 50 | Midazolam | 2.5 | 50 | Saline |
| Midazolam | 100 nm | 45 | Midazolam | 2.5 | 55 | Saline |
| Diazepam | 100 nm | 50 | Diazepam | 3.5 | 50 | Saline |
| Diazepam | 100 nm | 45 | Diazepam | 3.5 | 55 | Saline |
| Lorazepam | 100 nm | 50 | Lorazepam | 3.5 | 50 | Saline |
| Lorazepam | 100 nm | 45 | Lorazepam | 3.5 | 55 | Saline |
| Midazolam | 100 nm | 50 | Midazolam | 3.5 | 50 | Saline |

TABLE-continued

| Pop. 1 Active Pharmaceutical Ingredient | Pop. 1 Mean Particle Diameter (nm) | Pop. 1 Percent weight of total particles | Pop. 2 Active Pharmaceutical Ingredient | Pop. 2 Mean Particle Diameter (μm) | Pop. 2 Percent weight of total particles | Carrier |
|---|---|---|---|---|---|---|
| Midazolam | 100 nm | 45 | Midazolam | 3.5 | 55 | Saline |
| Diazepam | 300 nm | 50 | Diazepam | 2.5 | 50 | Saline |
| Diazepam | 300 nm | 45 | Diazepam | 2.5 | 55 | Saline |
| Lorazepam | 300 nm | 50 | Lorazepam | 2.5 | 50 | Saline |
| Lorazepam | 300 nm | 45 | Lorazepam | 2.5 | 55 | Saline |
| Midazolam | 300 nm | 50 | Midazolam | 2.5 | 50 | Saline |
| Midazolam | 300 nm | 45 | Midazolam | 2.5 | 55 | Saline |
| Diazepam | 300 nm | 50 | Diazepam | 3.5 | 50 | Saline |
| Diazepam | 300 nm | 45 | Diazepam | 3.5 | 55 | Saline |
| Lorazepam | 300 nm | 50 | Lorazepam | 3.5 | 50 | Saline |
| Lorazepam | 300 nm | 45 | Lorazepam | 3.5 | 55 | Saline |
| Midazolam | 300 nm | 50 | Midazolam | 3.5 | 50 | Saline |
| Midazolam | 300 nm | 45 | Midazolam | 3.5 | 55 | Saline |
| Midazolam | 100 nm | 50 | Diazepam | 3.5 | 50 | Saline |
| Diazepam | 100 nm | 15 | Diazepam | 2.5 | 25 | Saline |
| Diazepam | 100 nm | 50 | Lorazepam | 2.5 | 50 | Saline |
| Midazolam | 100 nm | 45 | Lorazepam | 2.5 | 55 | Saline |
| Lorazepam | 100 nm | 50 | Midazolam | 2.5 | 50 | Saline |
| Midazolam | 100 nm | 30 | Diazepam | 2.5 | 70 | Saline |
| Diazepam | 100 nm | 50 | Lorazepam | 3.5 | 50 | Saline |
| Diazepam | 100 nm | 45 | Diazepam | 3 | 55 | Saline |
| Lorazepam | 100 nm | 50 | Lorazepam | 3.5 | 50 | Saline |
| Lorazepam | 100 nm | 45 | Midazolam | 3.5 | 55 | Saline |
| Midazolam | 100 nm | 50 | Midazolam | 3.5 | 50 | Saline |
| Midazolam | 100 nm | 45 | Diazepam | 3.5 | 55 | Saline |
| Diazepam | 300 nm | 50 | Diazepam | 2.5 | 50 | HFC |
| Diazepam | 300 nm | 45 | Midazolam | 2.5 | 55 | HC |
| Lorazepam | 300 nm | 50 | Midazolam | 2.5 | 50 | HFC |
| Lorazepam | 300 nm | 45 | Lorazepam | 2.5 | 55 | HC |
| Midazolam | 300 nm | 20 | Lorazepam | 2.5 | 80 | HFC |
| Midazolam | 300 nm | 45 | Diazepam | 2.5 | 55 | HC |
| Diazepam | 300 nm | 50 | Diazepam | 3.5 | 50 | Saline |
| Diazepam | 300 nm | 45 | Diazepam | 3.5 | 55 | Saline |
| Lorazepam | 300 nm | 50 | Lorazepam | 3.5 | 50 | Saline |
| Lorazepam | 300 nm | 45 | Lorazepam | 3.5 | 55 | Saline |
| Midazolam | 300 nm | 50 | Midazolam | 3.5 | 50 | Saline |
| Midazolam | 300 nm | 45 | Midazolam | 3.5 | 55 | Saline |

Saline: 0.9% NaCl, optionally pH adjusted to 6 to 7.5 with NaOH or $H_2SO_4$
HFC: Hydrofluorocarbon propellant
HC: Hydrocarbon propellant

Example 2

Compositions comprising diazepam, lorazepam and/or midazolam (or pharmaceutically acceptable salts thereof) are prepared. The compositions are bimodal, comprising a first population of particles having a mean particle diameter of about 100 nm and a second population of particles having a mean particle diameter of about 3000 nm (about 3 μm). The first population of particles is prepared as described herein. The second population is then prepared as described herein. The two populations of particles are then combined in the weight proportions indicated below, mixed with a suitable delivery vehicle and dispensed into a suitable container for nasal installation. Compositions according this example are set forth in the following table.

TABLE

| Composition No. | Pop. 1 Active Pharmaceutical Ingredient | Pop. 1 Percent weight of total particles | Pop. 2 Active Pharmaceutical Ingredient | Pop. 2 Percent weight of total particles | Carrier |
|---|---|---|---|---|---|
| 1 | Diazepam | 50 | Diazepam | 50 | Saline |
| 2 | Diazepam | 45 | Diazepam | 55 | Saline |
| 3 | Lorazepam | 50 | Lorazepam | 50 | Saline |
| 4 | Lorazepam | 45 | Lorazepam | 55 | Saline |
| 5 | Midazolam | 50 | Midazolam | 50 | Saline |
| 6 | Midazolam | 45 | Midazolam | 55 | Saline |
| 7 | Diazepam | 50 | Diazepam | 50 | HFC |
| 8 | Diazepam | 45 | Diazepam | 55 | HC |
| 9 | Lorazepam | 50 | Lorazepam | 50 | HC |
| 10 | Lorazepam | 45 | Lorazepam | 55 | HFC |
| 11 | Midazolam | 50 | Midazolam | 50 | HFC |
| 12 | Midazolam | 15 | Midazolam | 85 | HFC |
| 13 | Diazepam | 15 | Diazepam | 85 | Saline |
| 14 | Diazepam | 85 | Diazepam | 15 | Saline |
| 15 | Lorazepam | 15 | Lorazepam | 85 | Saline |
| 16 | Lorazepam | 75 | Lorazepam | 25 | Saline |
| 17 | Midazolam | 60 | Midazolam | 40 | Saline |
| 18 | Midazolam | 25 | Midazolam | 75 | Saline |
| 19 | Diazepam | 15 | Midazolam | 85 | Saline |
| 20 | Diazepam | 15 | Diazepam | 85 | HFC |
| 21 | Lorazepam | 15 | Lorazepam | 85 | HFC |
| 22 | Lorazepam | 45 | Lorazepam | 55 | HC |
| 23 | Midazolam | 50 | Diazepam | 50 | Saline |
| 24 | Midazolam | 45 | Lorazepam | 55 | Saline |
| 25 | Midazolam | 80 | Lorazepam | 20 | Saline |

TABLE-continued

| Composition No. | Pop. 1 Active Pharmaceutical Ingredient | Pop. 1 Percent weight of total particles | Pop. 2 Active Pharmaceutical Ingredient | Pop. 2 Percent weight of total particles | Carrier |
|---|---|---|---|---|---|
| 26 | Midazolam | 15 | Diazepam | 75 | Saline |
| 27 | Diazepam | 50 | Lorazepam | 50 | Saline |
| 28 | Midazolam | 45 | Lorazepam | 55 | HFC |
| 29 | Lorazepam | 50 | Midazolam | 50 | Saline |
| 30 | Midazolam | 30 | Diazepam | 70 | Saline |
| 31 | Diazepam | 50 | Lorazepam | 50 | HFC |
| 32 | Diazepam | 45 | Midazolam | 55 | Saline |
| 33 | Lorazepam | 20 | Midazolam | 80 | HC |
| 34 | Lorazepam | 45 | Midazolam | 55 | Saline |
| 35 | Midazolam | 35 | Midazolam | 65 | Saline |
| 36 | Midazolam | 65 | Diazepam | 35 | Saline |
| 37 | Diazepam | 50 | Diazepam | 50 | HC |
| 38 | Diazepam | 45 | Midazolam | 55 | HC |
| 39 | Lorazepam | 50 | Midazolam | 50 | HFC |
| 40 | Lorazepam | 20 | Lorazepam | 80 | HC |
| 41 | Midazolam | 20 | Lorazepam | 80 | HFC |
| 42 | Midazolam | 45 | Diazepam | 55 | HC |
| 43 | Diazepam | 50 | Lorazepam | 50 | Saline |
| 44 | Diazepam | 45 | Lorazepam | 55 | Saline |
| 45 | Lorazepam | 20 | Lorazepam | 80 | Saline |
| 46 | Lorazepam | 45 | Lorazepam | 55 | Saline |
| 47 | Midazolam | 50 | Midazolam | 50 | Saline |
| 48 | Midazolam | 45 | Midazolam | 55 | Saline |

Saline: 0.9% NaCl, optionally pH adjusted to 6 to 7.5 with NaOH or $H_2SO_4$
HFC: Hydrofluorocarbon propellant
HC: Hydrocarbon propellant While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A bimodal particulate composition for nasal administration of benzodiazepine particulates having an effective average particle size greater than 2000 nm and a bimodal particle size distribution, comprising a first population of particles having a first effective average particle size and a second population of particles having a second effective average particle size, wherein the first effective average particle size is at least 1.5 times that of the second effective average particle size.

2. The bimodal particulate composition of claim 1, wherein the benzodiazepine comprises at least one member selected from the group consisting of: alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, lorazepam, mexazolam, prazepam, quazepam, triazolam, temazepam, loprazolam, and pharmaceutically acceptable salts and combinations thereof.

3. The bimodal particulate composition of claim 1, wherein the second population of particles has an average size in the range of 25 to 7000 nm and the first population of particles has an average size in the range of 500 to 10,000 nm.

4. The bimodal particulate composition of claim 1, wherein the difference between the average particle size of the first and second populations is greater than 100 nm.

5. The bimodal particulate composition of claim 1, wherein the difference between the average particle size of the first and second particle populations is greater than 10% of the average particle size of the second population of particles.

6. The bimodal particulate composition of claim 1, wherein the composition is a suspension of particles in a liquid carrier or diluent.

7. The pharmaceutical bimodal particulate composition of claim 1, comprising a first population of particles and a second populations of particles, wherein the second population of particles has a particle size distribution having a node between 0.5 μm and 5.0 μM and the first population of particles has a particle size distribution having a node greater than 5.0 μm.

8. The composition of claim 1, wherein the composition further comprises at least one member of the group consisting n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside and octyl β-D-thioglucopyranoside.

9. A method of using a bimodal particulate composition of claim 1, wherein the bimodal particulate composition is administered to at least one nostril.

10. The method of claim 9, wherein the bimodal particulate composition comprises an amount of benzodiazepine effective for acute treatment of seizure, reduction in the frequency of seizure and/or reduction in severity of seizure.

11. A pharmaceutical particulate composition for nasal delivery of benzodiazepine comprising benzodiazepine particulates having an effective average particle size greater than 2000 nm and a bimodal particle size distribution.

12. The pharmaceutical particulate composition of claim 11, wherein the medicament comprises at least one benzodiazepine selected from the group consisting of alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, lorazepam, mexazolam, prazepam, quazepam, triazolam, temazepam, loprazolam, and pharmaceutically acceptable salts and combinations thereof.

13. The pharmaceutical particulate composition of claim 11, wherein the composition is a suspension of particles in a liquid.

14. The pharmaceutical particulate composition of claim 13, wherein the composition is a non-aqueous dispersion or suspension of nanoparticulate benzodiazepine particles in a liquid.

15. The pharmaceutical particulate composition of claim 11, comprising a first population of particles and a second populations of particles, wherein the second population of particles has a particle size distribution having a node between 0.5 μm and 5.0 μm and the first population of particles has a particle size distribution having a node greater than 5.0 μm.

16. The composition of claim 11, wherein the composition further comprises at least one member of the group consisting n-decyl β-D-glucopyranoside; n-decyl β-D-maltopyranoside; n-dodecyl β-D-glucopyranoside; n-dodecyl β-D-maltoside; heptanoyl-N-methylgiucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside and octyl β-D-thioglucopyranoside.

17. A method of using a pharmaceutical particulate composition of claim 11, wherein the medicament is administered to at least one nostril.

18. An aerosol composition of an aqueous suspension or dispersion of nanoparticulate benzodiazepine particles, wherein droplets of the aerosol have a mass median aerodynamic diameter (MMAD) less than or equal to 1000 μm and the nanoparticulate benzodiazepine particles have a bimodal particle size distribution and an effective average particle size of greater than 2000 nm.

19. The aerosol composition of claim 18, wherein the benzodiazepine particles comprise at least one benzodiazepine selected from the group consisting of: alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, lorazepam, mexazolam, prazepam, quazepam, triazolam, temazepam, loprazolam, and pharmaceutically acceptable salts and combinations thereof.

20. The composition of claim 18, wherein the composition further comprises at least one member of the group consisting n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside and octyl β-D-thioglucopyranoside.

21. A method of using an aerosol composition of claim 19, wherein the aerosol composition is administered to at least one nostril.

22. The method of claim 21, wherein the aerosol composition comprises an amount of benzodiazepine effective for acute treatment of seizure, reduction in the frequency of seizure and or reduction in severity of seizure.

23. A method of using an aerosol composition of claim 19, wherein the composition is administered with a pulmonary delivery device.

24. The method of using an aerosol composition of claim 23, wherein the pulmonary delivery device is selected from a nebulizer, a dry powder inhaler and a metered dose inhaler.

* * * * *